US012576133B2

(12) United States Patent
McComb et al.

(10) Patent No.: US 12,576,133 B2
(45) Date of Patent: Mar. 17, 2026

(54) ANTIGEN-BINDING AGENTS THAT SPECIFICALLY BIND EPIDERMAL GROWTH FACTOR RECEPTOR VARIANT III

(71) Applicant: NATIONAL RESEARCH COUNCIL OF CANADA, Ottawa (CA)

(72) Inventors: Scott McComb, Ottawa (CA); Risini Dhammika Weeratna, Ottawa (CA); Maria Jaramillo, Beaconsfield (CA); Anne Marcil, Pierrefonds (CA); Traian Sulea, Kirkland (CA); Cunle Wu, Montreal (CA); Darin Bloemberg, Ottawa (CA)

(73) Assignee: National Research Council of Canada, Ottawa (CA)

( * ) Notice: Subject to any disclaimer, the term of this patent is extended or adjusted under 35 U.S.C. 154(b) by 1146 days.

(21) Appl. No.: 17/441,706

(22) PCT Filed: Mar. 23, 2020

(86) PCT No.: PCT/CA2020/050378
§ 371 (c)(1),
(2) Date: Sep. 22, 2021

(87) PCT Pub. No.: WO2020/191486
PCT Pub. Date: Oct. 1, 2020

(65) Prior Publication Data
US 2022/0323495 A1     Oct. 13, 2022

Related U.S. Application Data

(60) Provisional application No. 62/824,391, filed on Mar. 27, 2019.

(51) Int. Cl.
| | |
|---|---|
| *A61K 38/17* | (2006.01) |
| *A61K 40/11* | (2025.01) |
| *A61K 40/15* | (2025.01) |
| *A61K 40/31* | (2025.01) |
| *A61K 40/42* | (2025.01) |
| *A61P 35/00* | (2006.01) |
| *C07K 14/705* | (2006.01) |
| *C07K 14/725* | (2006.01) |
| *C07K 14/735* | (2006.01) |
| *C07K 16/28* | (2006.01) |
| *A61K 38/00* | (2006.01) |

(52) U.S. Cl.
CPC .......... *A61K 38/1774* (2013.01); *A61K 40/11* (2025.01); *A61K 40/15* (2025.01); *A61K 40/31* (2025.01); *A61K 40/4204* (2025.01); *A61K 40/4211* (2025.01); *A61P 35/00* (2018.01); *C07K 14/705* (2013.01); *C07K 14/7051* (2013.01); *C07K 14/70535* (2013.01); *C07K 14/70596* (2013.01); *C07K 16/2863* (2013.01); *A61K 38/00* (2013.01); *A61K 2239/31*

(2023.05); *A61K 2239/38* (2023.05); *C07K 2317/24* (2013.01); *C07K 2317/31* (2013.01); *C07K 2317/56* (2013.01); *C07K 2317/565* (2013.01); *C07K 2317/567* (2013.01); *C07K 2317/622* (2013.01)

(58) Field of Classification Search
None
See application file for complete search history.

(56) References Cited

U.S. PATENT DOCUMENTS

| | | | |
|---|---|---|---|
| 7,736,644 | B2 | 6/2010 | Weber et al. |
| 2016/0069900 | A1 | 3/2016 | Ayanoglu |

FOREIGN PATENT DOCUMENTS

| | | |
|---|---|---|
| WO | WO2014075697 A1 | 5/2014 |
| WO | WO2018136626 A1 | 7/2018 |
| WO | WO2018/191748 A1 | 10/2018 |

OTHER PUBLICATIONS

Bloemberg, Darin et al, "A High-Throughput Method for Characterizing Novel Chimeric Antigen Receptors in Jurkat Cells", Molecular Therapy-Methods & Clinical Development; vol. 16, Mar. 1, 2020, pp. 238-254.
Abhinandan and Martin, Analysis and Imrpvements to Kabat and Structurally Correct Numbering of Antibody Variable Domains, Mol Immunol., 45(14):3832-9, (2008).
Andris-Widhopf, J., et al. Generation of human scFv antibody libraries: PCR amplification and assembly of light- and heavy-chain coding sequences. Cold Spring Harbor protocols, 2011(9).
Bird R.E. et al. "Single-Chain Antigen-Binding Proteins" Science 242:423-426 (1988).

(Continued)

*Primary Examiner* — Joanne Hama
*Assistant Examiner* — Estella M. Gustilo
(74) *Attorney, Agent, or Firm* — Gail C. Silver

(57) ABSTRACT

The present disclosure relates to antigen-binding agents that specifically bind to epidermal growth factor receptor variant III (EGFRvIII). Antigen-binding agents of the present disclosure include antibodies and antigen-binding fragments thereof, chimeric antigen receptors (CARs) and bi-specific T-cell engagers (BiTE!), bispecific killer cell engagers (BiKEs) and trispecific killer cell engagers (TrikEs). Nucleic acid molecules and vectors expressing antibodies, antigen-binding fragments. CARs, BiTEs, BiKEs or TrikEs are also encompassed by the present disclosure. Immune cells engineered to express CARs, BiTEs, BiKEs or TrikEs may be used to specifically recognize and kill cells expressing EGFRvIII.

23 Claims, 22 Drawing Sheets
Specification includes a Sequence Listing.

(56)　　　　References Cited

OTHER PUBLICATIONS

Chojnacki, S. et al., "Programmatic Access to Bioinformatics Tools from EMBL-EBI Update: 2017" Nucl Acid Res. 45 (W1): W550-553 (2017).

Chothia C, Lesk AM. Canonical structures for the hypervariable regions of immunoglobulins. J Mol Biol. Aug. 20;196 (4):901-17 (1987).

Feldhaus MJ et al., "Flow-Cytometric Isolation of Human Antibodies from a Nonimmune *Saccharomyces cerevisiae* Surface Display Library", Nat Biotechnol. Feb. 21(2):163-70 (2003).

Gacerez, A.T. et al., «How Chimeric Antigen Receptor Design Affects Adoptive T Cell Therapy, J Cell Physiol. 231 (12):2590-2598 (2016).

Gan H.K., Anna N. Cvrljevic, Terrance G. Johns. The epidermal growth factor receptor variant III (EGFRvIII): where wild things are altered. FEBS Journal 280;5350-5370 (2013).

Gong et al; « Characterization of a Human Cell Line (NK-92) with Phenotypical and Functional Characteristics of Activated Natural Killer Cells, Leukemia, 8(4) :652-658 (1994).

Hamblett K.J, et al., "AMG 595, an Anti-EGFRvIII Antibody-Drug Conjugate, Induces Potent Antitumor Acrivity against EGFRvIII-Expresssing Glioblastoma", Molecular Cancer Therapeutics, vol. 14(7), pp. 1614-1624, (2015).

Huston et al. «Protein Engineering of Antibody Binding Sites : Recovery of Specific Activity in an Anti-Digoxin Single-Chain Fv Analogue Produced in *Escherichia coli*, Proc. Natl. Acad. Sci. USA 85:5879-5883 (1988).

Jones PT, Dear PH, Foote J, Neuberger MS, Winter G., "Replacing the Complementarity-Determining Regions in a Human Antibody with those from a Mouse", Nature 321, 522-525 (1986).

Johnson G, Wu TT. The Kabat database and a bioinformatics example. Methods Mol Biol., 248:11-25 (2004).

Kabat EA, Wu TT. Identical V region amino acid sequences and segments of sequences in antibodies of different specificities. Relative contributions of VH and VL genes, minigenes, and complementarity-determining regions to binding of antibody-combining sites. J Immunol., 147:1709-19 (1991).

Kuan, C-T. et al., « EGFR mutant receptor vill as a molecular target in cancer therapy. Endocrine-Related Cancer, vol. 8, No. 2, pp. 83-96 (2001).

Lefranc, M.-P., "The IMGT Unique Numbering for Immunoglobulins, T-Cell Receptors, and Ig-Like Domains" The Immunologist, 7, 132-136 (1999).

Mendelsohn J, Prewett M, Rockwell P, Goldstein Ni. Ccr 20th anniversary commentary: a chimeric antibody, C225, inhibits EGFR activation and tumor growth. Clin Cancer Res. 21(2):227-9 (2015).

Queen C, Schneider WP, Selick HE, Payne PW, Landolfi NF, Duncan JF, Avdalovic NM, Levitt M, Junghans RP, Waldmann Ta. "A Humanized Antibody that Binds to the Interleukin 2 Receptor", Proc Natl Acad Sci USA 86, 10029-10033 (1989).

Reilly, E.B. et al., « Characterization of ABT-806, a Humanized Tumor-Specific Anti-EGFR Monoclonal Antibody, Molecular Cancer Therapeutics, vol. 14, No. 5, pp. 1141-1145 (2015).

Riechmann L, Clark M, Waldmann H, Winter G. "Reshaping human Antibodies for Therapy", Nature 332, 323-327 (1988).

Sadelain, M. et al. "The Basic Principles of Chimeric Antigen Receptor Design", Cancer Discovery, 3(4):388-98, (2013).

Sblattero & Bradbury, 2000, "Exploiting Recombination in Single Bacteria to Make Large Phage Antibody Libraries" Nature Biotechnology, 18(1):75-80, (2000).

Schaefer, J. V, et al. Construction of scFv Fragments from Hybridoma or Spleen Cells by PCR Assembly. (R. Kontermann & S. Dübel, Eds.), (2010).

Tatusova, T., Thomas L. Madden, "Blast 2 sequences—a new tool for comparing protein and nucleotide sequences", FEMS Microbiol Lett. 174:247-250 (1999).

Tempest PR, Bremmer P, Lambert M, Taylor G, Furze JM, Carr FJ, Harris Wj., R. "Reshaping a Human Monoclonal Antibody to Inhibit Human Respiratory Syncytial Virus Infection in vivo", Biotechnology 9, 266-271 (1991).

Tsurushita N, Hinton, RP, Kumar S., Design of humanized antibodies: From anti-Tac to Zenapax. Methods 36, 69-83 (2005).

Wang, X et al., "Clinical Manufacturing of Car T Cells: Foundation of a Promising Therapy", Molecular Therapy—Oncolytics, 3:16015, (2016).

Ward et al., "Binding Activities of a Repertoire of Single Immunoglobulin Variable Domains Secreted from *Escherichia coli*", Nature 341:544-546, (1989).

Zhang, C. et al., "Engineering CAR-T Cells" Biomarker Research, 5 :22 (2017).

Concetta Quintareli et al.: "Choise of costimulatory domains and of cytokines determines CAR T-cell activity in neuroblastoma", Oncolmmunology, vol. 7, No. 6, Mar. 15, 2018, p. e1433518, XP055594669, DOI: 10.1080/2162402X.2018.1433518.

EPO Communication pursuant to Article 94(3) dated Jan. 31, 2025.

Fig. 1A: 5B7
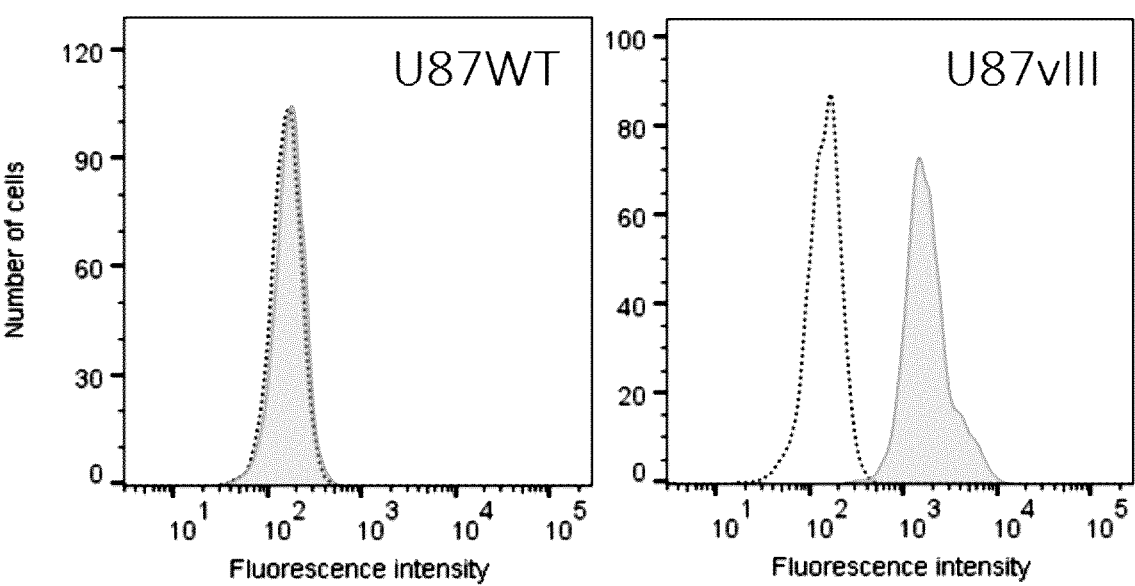
Fig. 1B: 3D12
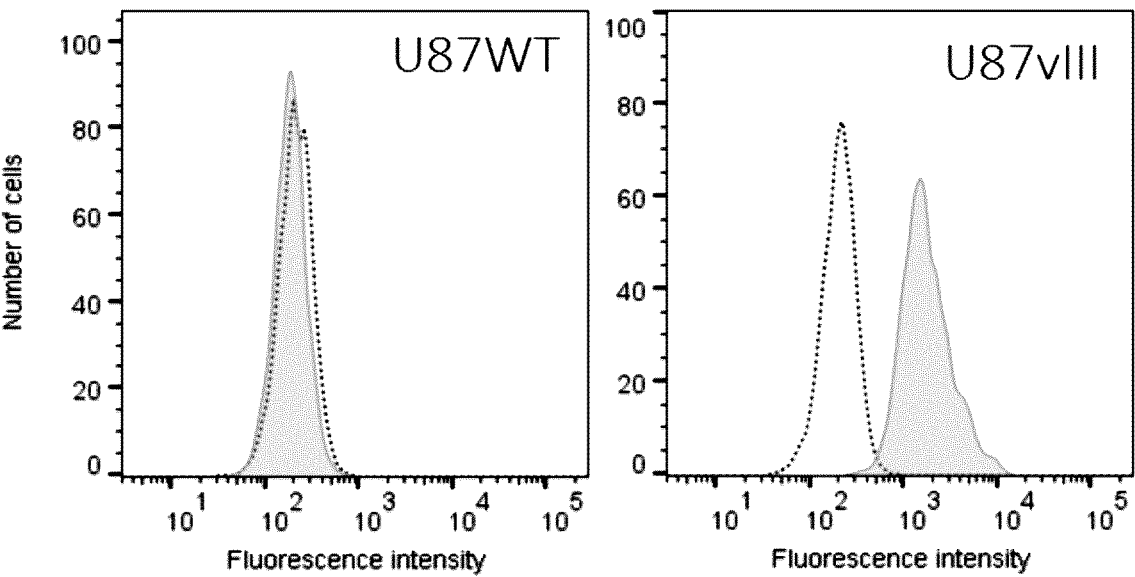
Figure 1 A and B

Fig. 1C: 1D2
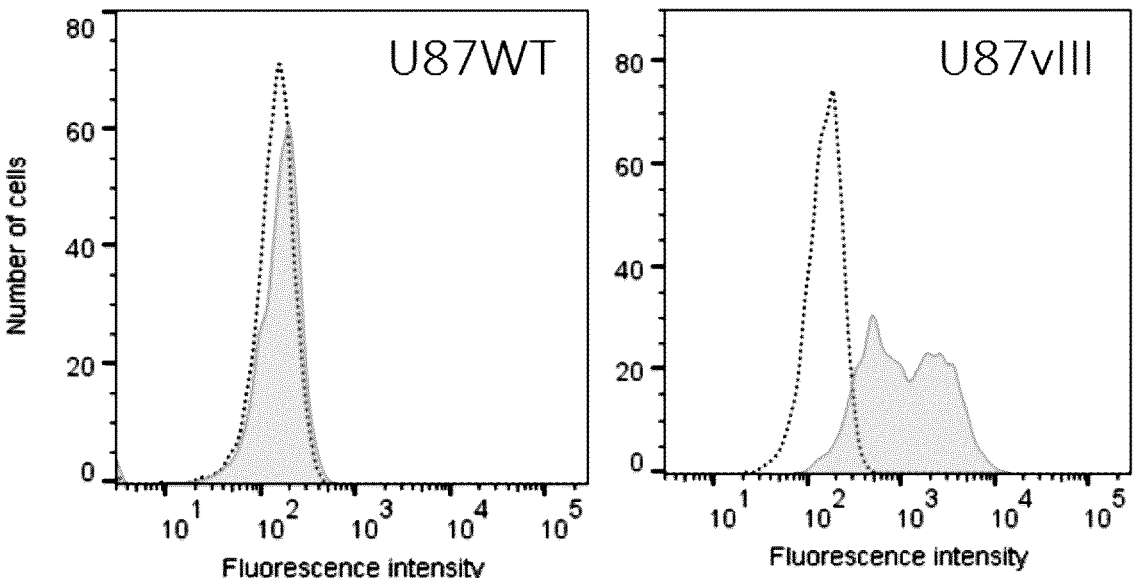
Fig. 1D: 225
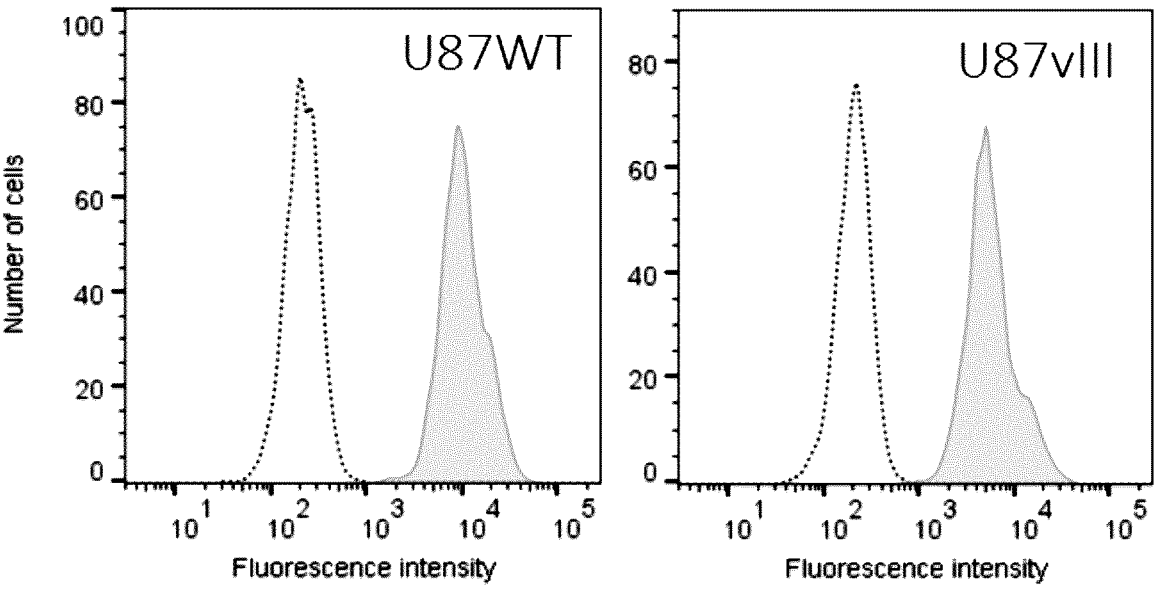

Fig. 1E: 13.1.2 (mIgG2a)
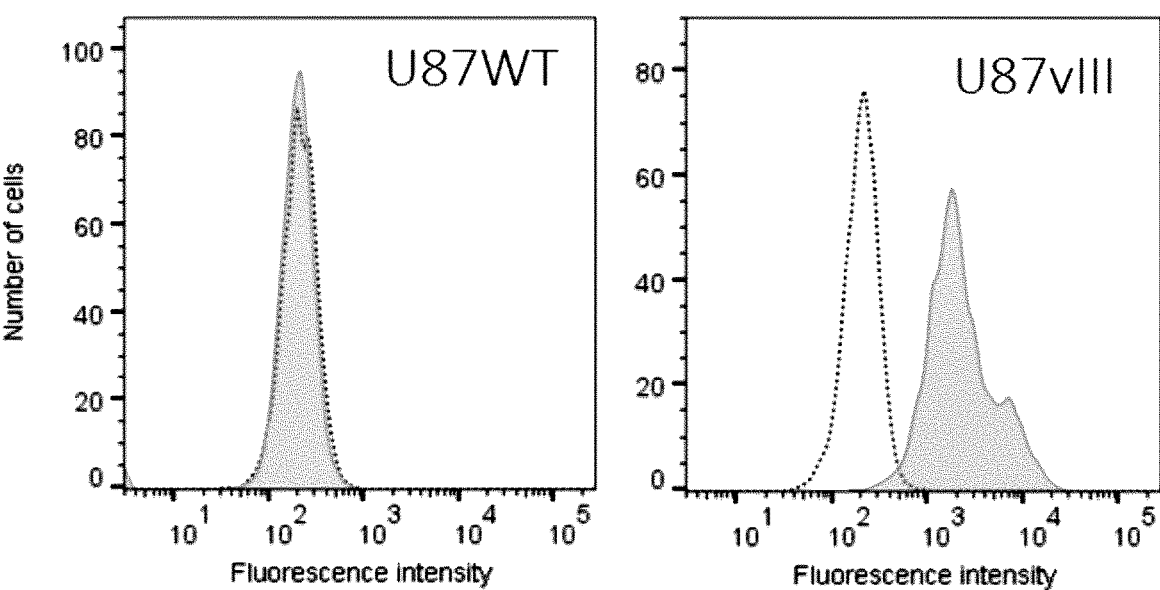

```
EGFR WT   (SEQ ID NO: 2)    1   LEEKKVCQGTSNKLTQLGTFEDHFLSLQRMFNNCEVVLGNLEITYVQRNYDLSFLKTIQE    60
EGFRvIII  (SEQ ID NO: 91)   1   LEEKK-------------------------------------------------------     5

EGFR WT   (SEQ ID NO: 2)   61   VAGYVLIALNTVERIPLENLQIIRGNMYYENSYALAVLSNYDANKTGLKELPMRNLQEIL   120
EGFRvIII  (SEQ ID NO: 91)   5   -----------------------------------------------------------

EGFR WT   (SEQ ID NO: 2)  121   HGAVRFSNMPALCNVESIQWRDIVSSDFLSNMSMDFQNHLGSCQKCDPSCPNGSCWGAGE   180
EGFRvIII  (SEQ ID NO: 91)   5   -----------------------------------------------------------

EGFR WT   (SEQ ID NO: 2)  181   ENCQKLTKIICAQQCSGRCRGKSPSDCCHNQCAAGCTGPRESDCLVCRKFRDEATCKDTC   240
EGFRvIII  (SEQ ID NO: 91)   5   -----------------------------------------------------------

EGFR WT   (SEQ ID NO: 2)  241   PPLMLYNPTTYQMDVNPEGKYSFGATCVKKCPRNYVVTDHGSCVRACGADSYEMEEDGVR   300
EGFRvIII  (SEQ ID NO: 91)   5   ------------------------GNYVVTDHGSCVRACGADSYEMEEDGVR           33

EGFR WT   (SEQ ID NO: 2)  301   KCKKCEGPCRKVCNGIGIGEFKDSLSINATNIKHFKNCTSISGDLHILPVAFRGDSFTHT   360
EGFRvIII  (SEQ ID NO: 91)  34   KCKKCEGPCRKVCNGIGIGEFKDSLSINATNIKHFKNCTSISGDLHILPVAFRGDSFTHT    93

EGFR WT   (SEQ ID NO: 2)  361   PPLDPQELDILKTVKEITGFLLIQAWPENRTDLHAFENLEIIRGRTKQHGQFSLAVVSLN   420
EGFRvIII  (SEQ ID NO: 91)  94   PPLDPQELDILKTVKEITGFLLIQAWPENRTDLHAFENLEIIRGRTKQHGQFSLAVVSLN   153

EGFR WT   (SEQ ID NO: 2)  421   ITSLGLRSLKEISDGDVIISGNKNLCYANTINWKKLFGTSGQKTKIISNRGENSCKATGQ   480
EGFRvIII  (SEQ ID NO: 91)  94   ITSLGLRSLKEISDGDVIISGNKNLCYANTINWKKLFGTSGQKTKIISNRGENSCKATGQ   213

EGFR WT   (SEQ ID NO: 2)  481   VCHALCSPEGCWGPEPRDCVSCRNVSRGRECVDKCNLLEGEPREFVENSECIQCHPECLP   540
EGFRvIII  (SEQ ID NO: 91) 154   VCHALCSPEGCWGPEPRDCVSCRNVSRGRECVDKCNLLEGEPREFVENSECIQCHPECLP   273

EGFR WT   (SEQ ID NO: 2)  541   QAMNITCTGRGPDNCIQCAHYIDGPHCVKTCPAGVMGENNTLVWKYADAGHVCHLCHPNC   600
EGFRvIII  (SEQ ID NO: 91) 214   QAMNITCTGRGPDNCIQCAHYIDGPHCVKTCPAGVMGENNTLVWKYADAGHVCHLCHPNC   333

EGFR WT   (SEQ ID NO: 2)  541   TYGCTGPGLEGCPTNGPKIPS   621
EGFRvIII  (SEQ ID NO: 91) 214   TYGCTGPGLEGCPTNGPKIPS   354
```

Figure 2

| Clone | EGFR fragment | 5B7 | 3D12 | 1D2 | hFc-13.1.2 | a-EGFR 225 |
|---|---|---|---|---|---|---|
| 2R-1 | vIII_(1-62) | ++ | nt | + | +++ | nt |
| 2R-2 | vIII_(1-49) | ++ | +++ | + | +++ | nt |
| 2R-3 | vIII_(1-33) | +/- | - | + | +++ | nt |
| 2R-4 | vIII_(1-18) | - | - | + | +++ | nt |
| 2R-5 | vIII_(19-76) | nt | nt | nt | - | nt |
| 2R-6 | vIII_(19-62) | nt | nt | nt | - | nt |
| 2R-7 | vIII_(19-49) | - | nt | - | - | nt |
| 2R-8 | vIII_(19-33) | nt | nt | nt | - | nt |
| 2R-9 | vIII_(58-76) | nt | nt | nt | - | nt |
| 2R-10 | vIII_(43-76) | nt | nt | nt | - | nt |
| 2R-11 | vIII_(43-62) | nt | nt | nt | - | nt |
| 3R-2 | vIII_(28-49) | - | nt | - | nt | nt |
| 3R-3 | vIII_(33-49) | - | nt | - | nt | nt |
| 3R-4 | vIII_(36-49) | - | nt | - | nt | nt |
| 3R-5 | vIII_(19-45) | - | - | - | nt | nt |
| 3R-6 | vIII_(28-45) | - | nt | - | nt | nt |
| 3R-7 | vIII_(33-45) | - | nt | - | nt | nt |
| 3R-8 | vIII_(36-45) | - | - | - | nt | nt |
| 3R-9 | vIII_(19-37) | - | - | - | nt | nt |
| 3R-10 | vIII_(28-37) | - | nt | - | nt | nt |

Figure 3A

| Clone | EGFR fragment | 5B7 | 3D12 | 1D2 | hFc-13.1.2 | a-EGFR 225 |
|-------|---------------|-----|------|-----|------------|------------|
| 4R-2 | vIII_(1-45) | ++ | nt | + | +++ | nt |
| 4R-3 | vIII_(1-37) | ++ | ++ | + | +++ | nt |
| 4R-4 | vIII_(3-49) | ++ | nt | - | - | nt |
| 4R-5 | vIII_(3-45) | ++ | nt | - | - | nt |
| 4R-6 | vIII_(3-37) | ++ | +++ | - | - | nt |
| 4R-7 | vIII_(6-49) | ++ | nt | - | - | nt |
| 4R-8 | vIII_(6-45) | ++ | nt | - | - | nt |
| 4R-9 | vIII_(6-37) | ++ | nt | - | - | nt |
| 4R-10 | vIII_(10-49) | ++ | nt | - | - | nt |
| 4R-11 | vIII_(10-45) | ++ | nt | - | - | nt |
| 4R-12 | vIII_(10-37) | ++ | nt | - | - | nt |
| 4R-13 | vIII_(15-49) | ++ | nt | - | - | nt |
| 4R-14 | vIII_(15-45) | ++ | nt | - | - | nt |
| 4R-15 | vIII_(15-37) | ++ | ++ | - | - | nt |
| 1R-3 | vIII_(1-76) | ++ | +++ | + | +++ | - |
| 1R-5 | vIII_(43-456) | - | - | - | - | ++ |
| YF-3 | wt (266-482) | +/- | nt | - | - | nt |
| YF-5 | wt (1-623) | - | nt | - | - | nt |

Figure 3B (SEQ ID NO: 30)

QIQLVQSGPELKKPGETVMISCKASGYSFTNYGMNWVKQAPEKDLKWMGWINTYTGESRYVDEFKGRFAF

——————— 5B7 heavy chain ———————

SLETSVSIVYLKINNLKNEDMATYFCARGPNFDVWGTGTTVTVSSAKTTAPSVYPLAPGSLGGTGGSGGG

——————→   * *

GSGGGGSDVVMTQTPLTLSVTIGQPASISCKSSQSLLDSDGKTYLNWLLQRPGQSPKRLIYLVSKLDSGV

——————— 5B7 light chain ———————

——————→

PDRFTGSGSGTDFTLKISRVEAEDLGVYYCWQGTHFPQTFGGGTKLEIKRADAAPTVSIFPPSSKLGVIS

NSVMYFSSVPVLQKVNSTTTKPVLRTPSPVHPTGTSQPRPEDCRPRGSVKGTGLDFA

——————— Mouse CD8 hinge ———————→

Legend: * = restriction site; double underline = Linker

Figure 4

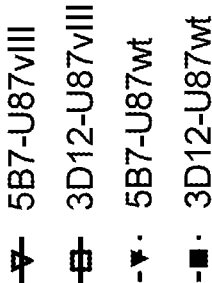
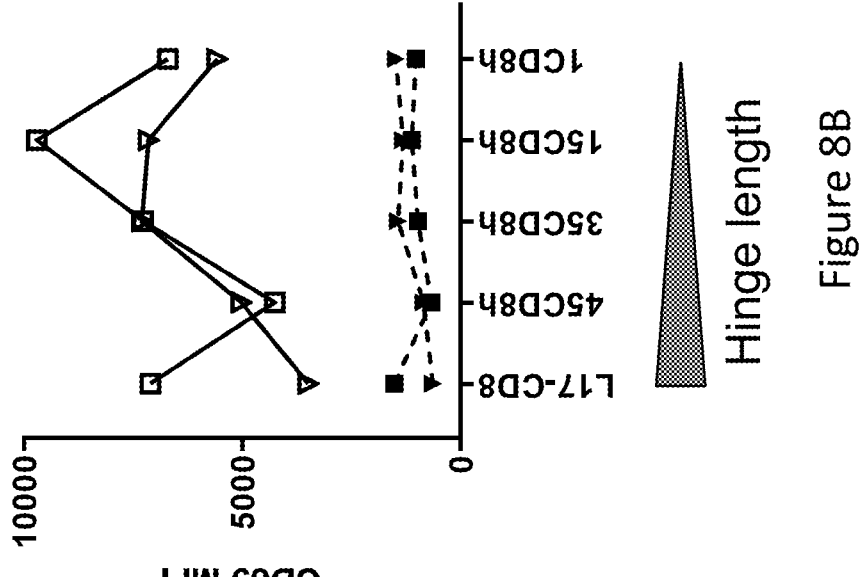
Figure 8B

Figure 10A:
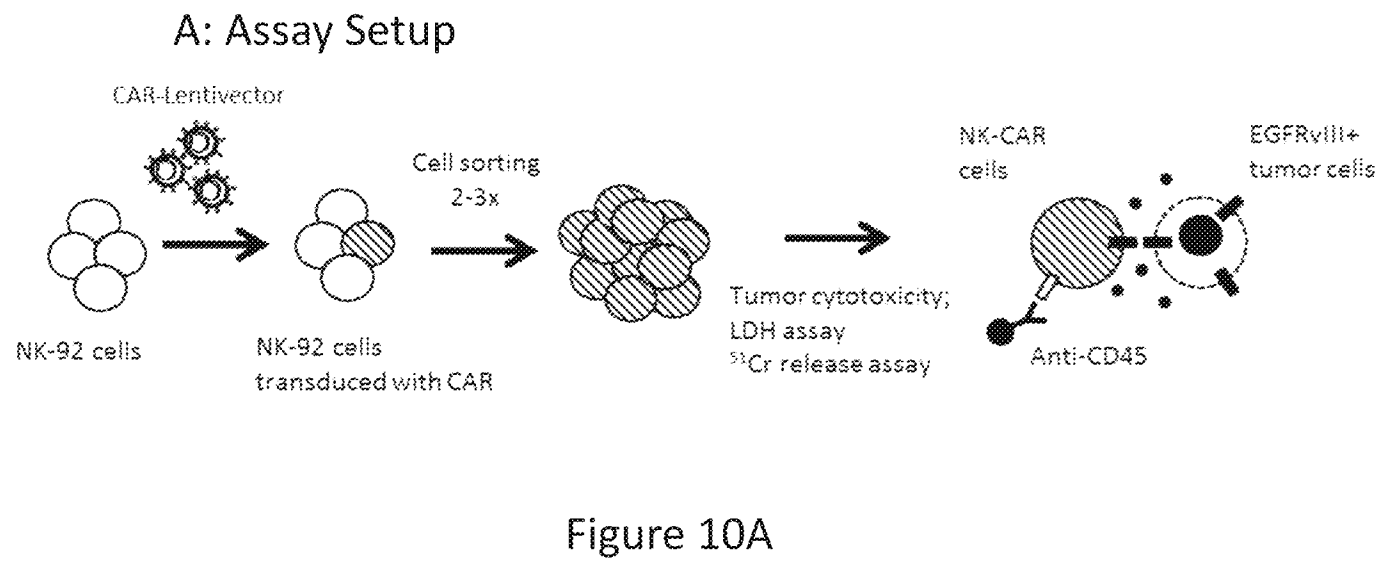

A: Assay Setup

NK-92 cells

CAR-Lentivector

NK-92 cells transduced with CAR

Cell sorting 2-3x

Tumor cytotoxicity, LDH assay, ⁵¹Cr release assay

NK-CAR cells

Anti-CD45

EGFRvIII+ tumor cells

ANTIGEN-BINDING AGENTS THAT SPECIFICALLY BIND EPIDERMAL GROWTH FACTOR RECEPTOR VARIANT III

PRIORITY CLAIM

This patent application is a national stage filing under 35 U.S.C. § 371 of international application No. PCT/CA2020/050378 filed on Mar. 23, 2020, which claimed priority to U.S. provisional application No. 62/824,391 filed on Mar. 27, 2019, the entire contents of which is incorporated herein by reference.

SEQUENCE LISTING

The Sequence Listing submitted as an ASCII text file via EFS-Web, entitled "2018-082-03_SL_07Aug2025_ST25.txt", created on Aug. 7, 2025, and of 107,408 bytes in size, is incorporated herein by reference.

TECHNICAL FIELD

The present disclosure relates to antigen-binding agents that specifically bind to epidermal growth factor receptor variant III (EGFRvIII). Antigen-binding agents of the present disclosure include antibodies and antigen-binding fragments thereof, for use in immunotherapeutic modalities including but not limited to chimeric antigen receptors (CARs), bi-specific T-cell engagers (BiTE™), bispecific killer cell engagers (BiKEs) and trispecific killer cell engagers (TrikEs). Nucleic acid molecules and vectors expressing antibodies, antigen-binding fragments, CARs, BiTEs, BiKEs or TriKEs are also encompassed by the present disclosure. Immune cells engineered to express CARs, BiTEs, BiKEs or TriKEs may be used to specifically recognize and kill cells expressing EGFRvIII.

BACKGROUND

EGFRvIII is a well-known tumor-specific mutation of epidermal growth factor receptor (EGFR) that consists of an in-frame deletion of exons 2-7 near the amino terminus of the extracellular domain that removes 267 amino acids from the extracellular domain encompassing the ligand binding domain. This deletion mutant is amplified and highly expressed in 25-64% of high-grade gliomas especially in glioblastoma multiforme (GBM). This genetic alteration has also been detected in a subset of carcinomas of the breast as well as in head and neck squamous-cell carcinoma (HN-SCC) using multiple complementary techniques (reviewed in Gan H. K., et al 2013). Numerous studies show that normal tissues are devoid of EGFRvIII, thus making this an ideal cell-surface tumor target amenable to immunotherapy. Clinical evaluation of EGFRvIII targeted immunotherapy including monoclonal antibodies, vaccines and chimeric antigen receptor (CAR)-T cells have/are been conducted with no reports of serious adverse effects; however, none have been approved for therapeutic applications.

CAR-T therapies have revolutionized cancer therapy approaches with phenomenal cure rates (50-90%) in patients with previously incurable aggressive forms of B cell leukemia leading to the regulatory approval of two CD19 targeted CAR-T products for the treatment of B cell malignancies. Despite these high cure rates in liquid tumors, success of CAR therapy in solid tumors have been limited up to date. This is due to a multitude of reasons including the lack of appropriate tumor specific antigens leading to on-target but off-tumor toxicity and tumor mediated barriers that prevent adequate penetration of CAR-modified immune cells and immune suppressive factors in the tumor microenvironment that negatively impact the functionality of CAR modified immune cells. Thus, the development of new CAR therapies to target solid tumors is an area of active investigation. With the tumor specific expression of EGFRvIII which is not present on normal healthy tissues; specific targeting of tumors by immune cells would provide great therapeutic potential with good safety margin for cancers expressing EGFRvIII. Targeting EGFRvIII using novel CAR-T therapies has shown some promise in clinical trials, but none have yet been approved for clinical application. In the present application, monoclonal antibodies that specifically bind to EGFRvIII and not the wild-type EGFR protein have been used to generate chimeric antigen receptor-T (CAR-T) or -NK (CAR-NK) cells to target human cancers that express EGFRvIII including but not limited to GBM, breast, head & neck or oral cancers.

SUMMARY

The present disclosure relates to antigen-binding agents that specifically bind to EGFRvIII and to nucleic acids encoding same.

More particularly, the present disclosure provides antibodies or antigen-binding fragments that specifically bind to EGFRvIII, as well as chimeric antigen receptors (CARs), bispecific T-cell engagers (BiTE™), bispecific killer cell engagers (BiKEs) and trispecific killer cell engagers (TrikEs) that comprise an antigen-binding domain of such antibodies. Antibodies, antigen-binding fragments and CARs are particularly encompassed by the present disclosure.

In accordance with the present disclosure, the antigen-binding domain may comprise complementarity determining regions of an antibody or antigen-binding fragment that specifically binds to EGFRvIII. More particularly, the antigen-binding domain may comprise the heavy chain and light chain variable regions of an antibody or antigen-binding fragment that specifically binds to EGFRvIII. The antigen-binding domain may be in the form of a single chain variable fragment (scFv).

The anti-EGFRvIII antibodies and antigen-binding fragments thereof of the present disclosure may be selected for their lack of binding to wild type EGFR. Moreover, the anti-EGFRvIII antibodies and antigen-binding fragments thereof of the present disclosure may be selected for their lack of internalization in cancer cells. The anti-EGFRvIII antibodies and antigen-binding fragments thereof of the present disclosure may specifically bind to native or denatured EGFRvIII or to an epitope present in both native and denatured EGFRvIII (e.g., linear epitope).

The anti-EGFRvIII antibodies or antigen-binding fragments of the present disclosure may be used as diagnostics and/or therapeutics.

The general structure of the chimeric antigen receptors of the present disclosure is composed of an antigen-binding domain of anti-EGFRvIII antibody, an optional spacer, a transmembrane domain, an optional costimulatory domain and an intracellular signaling domain.

The antigen-binding domain of CARs is generally composed of an antibody's heavy chain and light chain variable regions connected via a linker and forming a single chain (e.g., scFv). The linker may be any linker that allows for the VL and VH chain to form a functional antigen-binding region.

BiTE, BiKE and TriKE molecules may comprise an antigen-binding domain (e.g. scFv) that specifically binds to EGFRvIII and another domain (scFv) that binds to specific immune cells including but not limited to a T-cell specific molecule (e.g., CD3) and NK-cell surface molecules (e.g. CD16). These generally comprise multiple scFvs connected in tandem by flexible linkers.

The antigen-binding domain of CARs or other biologics including and not limited to BiTEs, BiKEs and TriKEs may comprise for example, complementarity determining regions (CDRs) of the antibody heavy chain. The antigen-binding domain may comprise, for example, at least two CDRs of the antibody heavy chain (including for example, at least CDRH3). The antigen-binding domain may more particularly comprise three CDRs of antibody heavy chain. Moreover, the antigen-binding domain may comprise or also comprise CDRs of the antibody light chain. The antigen-binding domain may comprise, for example, at least two CDRs of the antibody light chain. More specifically, the antigen-binding domain may comprise at least three CDRs of the antibody light chain.

A particular aspect of the present disclosure relates to antigen-binding agents (antibodies, CARs, BiTEs, BiKEs, TriKEs and the like) which comprise an antigen-binding domain having three CDRs of the light chain and three CDRs of the heavy chain of the antibody and nucleic acids encoding same. Antibodies, antigen binding fragments, CARs, BiTEs, BiKEs, or TriKEs of the present disclosure may be used in the treatment of cancer.

The present disclosure also relates to cells expressing the antigen-binding agents of the present disclosure and their use in the treatment of cancer.

Exemplary embodiments of antigen-binding agents of the present disclosure include those that bind to a peptide comprising or consisting of amino acid residues 1-76 of human EGFRvIII ectodomain (SEQ ID NO:69), to a peptide comprising or consisting of amino acid residues 3-37 of human EGFRvIII ectodomain (SEQ ID NO:70), and/or to a peptide comprising or consisting of amino acid residues 1-18 of human EGFRvIII ectodomain (SEQ ID NO:71).

More particularly, the present disclosure encompasses antigen-binding agents that bind to a peptide comprising or consisting of amino acid residues 15-37 of human EGFRvIII ectodomain (SEQ ID NO:5).

The antigen-binding agents of the present disclosure may bind to an epitope comprising amino acid residues Cys20 and/or Cys35 in SEQ ID NO:5. More particularly, the anti-EGFRvIII antibody or antigen-binding fragment thereof may bind to an epitope comprising amino acid residues Arg18, Cys20, Gly21 and Cys35 in SEQ ID NO:5.

Particularly, encompassed by the present disclosure, are antigen-binding agents that bind to an epitope comprising amino acid residues Arg18, Cys20, Gly21, Tyr25, Glu26, Glu29, Gly31, Arg33 and Cys35 in SEQ ID NO:5 or to an epitope comprising amino acid residues Val17, Arg18, Cys20, Gly21, Asp23 and Cys35 in SEQ ID NO:5.

The antigen-binding agents of the present disclosure include for example, those that bind EGFRvIII (SEQ ID NO:4) and/or a peptide comprising an EGFRvIII fragment consisting of the amino acid sequence set forth in SEQ ID NO:5 but that are not able to significantly bind a peptide comprising or consisting of the amino acid sequence SCAR-ACGADSYEMEEDGVRKCKK (SEQ ID NO: 50) or SCVRACGAASYEMEEDGVRKCKK (SEQ ID NO:54).

The antigen-binding agents of the present disclosure also include for example those that bind EGFRvIII and/or a peptide comprising an EGFRvIII fragment consisting of the amino acid sequence set forth in SEQ ID NO:5 but that are not able to significantly bind a peptide comprising or consisting of the amino acid sequence SCVRACGADSAE-MEEDGVRKCKK (SEQ ID NO:56), SCVRACGADSYAMEEDGVRKCKK (SEQ ID NO:57) or SCVRACGADSYEMEEDAVRKCKK (SEQ ID NO:62).

The antigen-binding agents (e.g., antibody or antigen-binding fragment thereof, CARs and BiTEs, BiKEs, TriKEs) of the present disclosure may comprise, for example,
   a CDRL1 comprising or consisting of SEQ ID NO:7, a CDRL2 comprising or consisting of SEQ ID NO:8, a CDRL3 comprising or consisting of SEQ ID NO:9, a CDRH1 comprising or consisting of SEQ ID NO: 11, a CDRH2 comprising or consisting of SEQ ID NO: 12 and a CDRH3 comprising or consisting of SEQ ID NO:13;
   a CDRL1 comprising or consisting of SEQ ID NO:15, a CDRL2 comprising or consisting of in SEQ ID NO:16, a CDRL3 comprising or consisting of SEQ ID NO:17, a CDRH1 comprising or consisting of SEQ ID NO: 19, a CDRH2 comprising or consisting of SEQ ID NO: 20 and a CDRH3 comprising or consisting of SEQ ID NO:21, or;
   a CDRL1 comprising or consisting of SEQ ID NO:23, a CDRL2 comprising or consisting of SEQ ID NO:24, a CDRL3 comprising or consisting of SEQ ID NO:25, a CDRH1 comprising or consisting of SEQ ID NO:27, a CDRH2 comprising or consisting of SEQ ID NO: 28 and a CDRH3 comprising or consisting of SEQ ID NO:29.

In an additional aspect, the present disclosure relates to a composition or pharmaceutical composition comprising the antigen-binding agents (e.g., antibody or antigen-binding fragment thereof) of the present disclosure and a pharmaceutically acceptable carrier.

Yet another aspect of the present disclosure relates to isolated cells capable of expressing, assembling and/or secreting the antibody or antigen-binding fragment thereof.

The present disclosure also encompasses nucleic acids and vectors encoding and/or expressing antigen-binding agents (e.g., anti-EGFRvIII antibodies or antigen-binding fragments thereof, CARs, BiTEs, BiKEs, TriKEs and the like) of the present disclosure.

Since antibodies or antigen-binding fragments thereof are composed of two distinct chains, the nucleic acid sequence encoding the light chain or light chain variable region and the nucleic acid sequence encoding the heavy chain or heavy chain variable region may be provided on the same or on separate nucleic acid molecules or vectors.

For immunotherapy purposes, nucleic acids encoding CARs or BiTES, BiKEs, TriKEs or purified protein therapeutic forms of these entities are introduced into immune cells of a patient. The present disclosure therefore particularly relates to nucleic acid molecules encoding or capable of expressing CARs or BiTES, BiKEs, TriKEs. For immunotherapy purposes, BiTES, BiKEs or TriKEs may also be delivered to patients in the form of purified protein.

In a specific and non-limiting example, the isolated nucleic acid molecule of the present disclosure may encode a CAR, BiTE, BiKE or TriKE having an antigen-binding domain comprising CDRs comprising or consisting essentially of the amino acid sequence set forth in SEQ ID NO:7, SEQ ID NO:8, SEQ ID NO:9, SEQ ID NO: 11, SEQ ID NO: 12 or SEQ ID NO: 13.

In another specific and non-limiting example, the isolated nucleic acid molecule of the present disclosure may encode a CAR, BiTE, BiKE or TriKE having an antigen-binding domain comprising complementarity determining regions comprising or consisting essentially of the amino acid sequence set forth in SEQ ID NO: 15, SEQ ID NO: 16, SEQ ID NO: 17, SEQ ID NO: 19, SEQ ID NO:20 or SEQ ID NO:21.

In yet another specific and non-limiting example, the isolated nucleic acid molecule of the present disclosure may encode a CAR, BiTE, BiKE or TriKE having an antigen-binding domain comprising complementarity determining regions comprising or consisting essentially of the amino acid sequence set forth in SEQ ID NO:23, SEQ ID NO:24, SEQ ID NO:25, SEQ ID NO:27, SEQ ID NO:28 or SEQ ID NO:29.

In accordance with the present disclosure, the antigen-binding domain of the CARs, BiTEs, BiKEs or TriKEs may be in the form of a single chain variable fragment (scFv).

The scFv may have a structure defined by the formula VH-linker-VL or VH-[L]-VL. Alternatively, the scFv may have a structure defined by the formula VL-linker-VH or VL-[L]-VH. The term "VL" refers to the light chain variable region or to a portion thereof, the term "VH" refers to the heavy chain variable region or to a portion thereof and "L" refers to any linker that allows for the linking of the VL and VH to form a single polypeptide chain that allows for the interaction of the VL and VH to form an active antigen-binding region. In a non-limiting example, the linker may be, for example 5-50 amino acids or 10-25 amino acid residues and may comprise any linking sequence known to one of skill in the present art (including longer or shorter linker). An exemplary embodiment of a linker is provided in SEQ ID NO:47.

Exemplary embodiments of scFvs having the formula VH-linker-VL are provided in SEQ ID NOs: 73, 76 and 79. More particular embodiments of scFvs having the formula VH-linker-VL are provided in SEQ ID NOs: 72, 75 and 78. Additional embodiments of scFvs having the formula VH-linker-VL are provided in SEQ ID NOs: 44, 45 and 46.

In order to minimize immune reactions against non-human sequences, antibodies, antigen-binding fragments, CARs, BiTEs, BiKEs or TriKEs may comprise human or humanized framework amino acid sequences.

CARs of the present disclosure therefore comprise an antigen-binding domain of an anti-EGFRvIII antibody, a spacer (i.e., a hinge) and a transmembrane domain for proper anchoring at the cell membrane. CARs may also comprise at least one intracellular signaling domain for activation of particular immune pathways. The chimeric antigen receptor may also comprise at least one costimulatory domain helping in the activation process.

In an exemplary embodiment, the isolated nucleic acid molecule may encode an anti-EGFRvIII antibody or antigen-binding fragment, CAR, BiTE, BiKE or TriKE that may comprise an amino acid sequence at least 80% identical to the amino acid sequence of the heavy chain variable region set forth in SEQ ID NO: 10 and/or an amino acid sequence at least 80% identical to the amino acid sequence of the light chain variable region set forth in SEQ ID NO:6.

The isolated nucleic acid molecule may encode, for example, a CAR that may comprise an amino acid sequence at least 80% identical to the amino acid sequence set forth in SEQ ID NO: 30, SEQ ID NO: 32 or SEQ ID NO:74. The isolated nucleic acid molecule may comprise, for example, a nucleic acid sequence that encodes an amino acid encoded by the nucleic acid sequence set forth in SEQ ID NO:31.

In another exemplary embodiment, the isolated nucleic acid molecule may encode an anti-EGFRvIII antibody or antigen-binding fragment, CAR, BiTE, BiKE or TriKE that may comprise an amino acid sequence at least 80% identical to the amino acid sequence of the heavy chain variable region set forth in SEQ ID NO: 18 and/or an amino acid sequence at least 80% identical to the amino acid sequence of the light chain variable region set forth in SEQ ID NO: 14.

The isolated nucleic acid molecule may encode, for example, a chimeric antigen receptor that may comprise an amino acid sequence at least 80% identical to the amino acid sequence set forth in SEQ ID NO:33, SEQ ID NO:34 or as set forth in SEQ ID NO:77.

In yet another exemplary embodiment, the isolated nucleic acid molecule may encode an anti-EGFRvIII antibody or antigen-binding fragment, CAR, BiTE, BiKE or TriKE that may comprise an amino acid sequence at least 80% identical to the amino acid sequence of the heavy chain variable region set forth in SEQ ID NO:26 and/or an amino acid sequence at least 80% identical to the amino acid sequence of the light chain variable region set forth in SEQ ID NO:22.

The isolated nucleic acid molecule may encode, for example, a CAR that may comprise an amino acid sequence at least 80% identical to the amino acid sequence set forth in SEQ ID NO: 35, SEQ ID NO:36 or as set forth in SEQ ID NO:80.

Particular aspects of the present disclosure relate to isolated nucleic acid molecules encoding a CAR that may comprise:

an antigen-binding domain of an antibody that specifically binds to epidermal growth factor receptor variant III (EGFRvIII), wherein the antigen-binding domain comprises:

a CDRL1 comprising or consisting essentially of the amino acid sequence set forth in SEQ ID NO:7, a CDRL2 comprising or consisting essentially of the amino acid sequence set forth in SEQ ID NO:8, a CDRL3 comprising or consisting essentially of the amino acid sequence set forth in SEQ ID NO:9, a CDRH1 comprising or consisting essentially of the amino acid sequence set forth in SEQ ID NO:11, a CDRH2 comprising or consisting essentially of the amino acid sequence set forth in SEQ ID NO: 12 and a CDRH3 comprising or consisting essentially of the amino acid sequence set forth in SEQ ID NO:13;

a CDRL1 comprising or consisting essentially of the amino acid sequence set forth in SEQ ID NO:15, a CDRL2 comprising or consisting essentially of the amino acid sequence set forth in SEQ ID NO: 16, a CDRL3 comprising or consisting essentially of the amino acid sequence set forth in SEQ ID NO:17, a CDRH1 comprising or consisting essentially of the amino acid sequence set forth in SEQ ID NO: 19, a CDRH2 comprising or consisting essentially of the amino acid sequence set forth in SEQ ID NO: 20 and a CDRH3 comprising or consisting essentially of the amino acid sequence set forth in SEQ ID NO:21, or;

a CDRL1 comprising or consisting essentially of the amino acid sequence set forth in SEQ ID NO:23, a CDRL2 comprising or consisting essentially of the amino acid sequence set forth in SEQ ID NO:24, a CDRL3 comprising or consisting essentially of the amino acid sequence set forth in SEQ ID NO:25, a CDRH1 comprising or consisting essentially of the amino acid sequence set forth in SEQ ID NO:27, a CDRH2 comprising or consisting essentially of the amino acid sequence set forth in SEQ ID NO: 28 and
a CDRH3 comprising or consisting essentially of the
amino acid sequence set forth in SEQ ID NO:29;
optionally a spacer;
a transmembrane domain;
optionally at least one costimulatory domain, and;
at least one intracellular signaling domain.

Nucleic acids encoding CARs comprising at least one
intracellular signaling domain are particularly contemplated.

The intracellular signaling domain may be, for example
and without limitation, from CD3 zeta, CD3 gamma, CD3
delta, CD3 epsilon, common FcR gamma (FCERIG), FcR
beta (Fc Epsilon Rib), CD79a, CD79b, Fcgamma Rlla,
DAP10, or DAP12.

In accordance with the present disclosure, the CAR
encoded by the nucleic acid molecule of the present disclosure
may comprise at least one costimulatory domain.

The costimulatory domain may be, for example and
without limitation, from CD28, CD27, 4-1BB, OX40, CD7,
B7-1 (CD80), B7-2 (CD86), CD30, CD40, PD-1, ICOS,
lymphocyte function-associated antigen-1 (LFA-1), CD2,
LIGHT, NKG2C, B7-H3, a ligand that specifically binds
with CD83, CDS, ICAM-1, GITR, BAFFR, HVEM
(LIGHTR), SLAMF7, NKp80 (KLRF1), CD160, CD19,
CD4, CD8alpha, CD8beta, IL2R beta, IL2R gamma, IL7R
alpha, ITGA4, VLA1, CD49a, ITGA4, IA4, CD49D,
ITGA6, VLA-6, CD49f, ITGAD, CD1d, ITGAE, CD103,
ITGAL, CD11a, LFA-1, ITGAM, CD11b, ITGAX, CD11c,
ITGB1, CD29, ITGB2, CD18, LFA-1, ITGB7, TNFR2,
TRANCE/RANKL, DNAM1 (CD226), SLAMF4 (CD244,
2B4), CD84, CD96 (Tactile), CEACAM1, CRTAM, Ly9
(CD229), CD160 (BY55), PSGL1, CD100 (SEMA4D),
CD69, SLAMF6 (NTB-A, Ly108), SLAM (SLAMF1,
CD150, IPO-3), BLAME (SLAMF8), SELPLG (CD162),
LTBR, LAT, GADS, SLP-76, PAG/Cbp, NKp44, NKp30,
NKp46, and NKG2D or a combination thereof.

In accordance with the present disclosure, the nucleic acid
molecule may be operably linked to a promoter allowing
expression of the CAR in immune cells. Promoters that are
active or specific to T-cells or natural killer (NK) cells are
particularly contemplated.

The nucleic acid molecules of the present disclosure may
be cloned into a vector. In accordance with the present
disclosure the vector may be a viral vector, such as, for
example, lentiviral vectors, retroviral vector, adenoviral
vectors, adeno-associated viral vectors and the like.

In an additional aspect, the present disclosure relates to an
isolated cell transformed with the nucleic acid molecule or
with the vector disclosed herein.

In yet an additional aspect, the present disclosure relates
to an isolated host cell expressing the anti-EGFRvIII antibody
or antigen-binding fragment thereof, the CAR disclosed
herein or comprising the nucleic acid molecule, or the
vector disclosed herein.

In accordance with the present disclosure, the isolated
host cell or isolated cell population comprise immune cells.
The immune cells may be for example and without limitation,
T-cells, NK cells or combination thereof. The isolated
host cell or isolated cell population may be of human origin.

The CAR of the present disclosure is expressed at the
surface of the host cells. The CAR of the present disclosure
may recognize and bind to EGFRvIII expressed at the
surface of cancer cells. The cancer cells targeted by the
isolated cell population may comprise solid tumors.

In accordance with the present disclosure, the isolated cell
population may comprise T-cells, Natural Killer (NK) cells,
cytotoxic T-cells, regulatory T-cells, and combinations
thereof.

More particularly, the isolated cell population may comprise
T-cells such as CD4+ T-cells, CD8+ T-cells or a
combination thereof.

Alternatively, the isolated cell population may comprise
NK cells or any immune cell capable of expressing the
chimeric antigen receptor.

The isolated cell population of the present disclosure may
be engineered to express another (a second) chimeric antigen
receptor having affinity for another (a second) antigen of
the same target or of a different target.

In another aspect, the present disclosure relates to a
pharmaceutical composition that comprises the isolated cell
population disclosed herein and a pharmaceutically acceptable
carrier or excipient.

In accordance with the present disclosure, the pharmaceutical
composition may be used for treating a solid tumor
using a population of T-cells and/or NK cells engineered to
express the chimeric antigen receptor of the present disclosure.

In yet another aspect, the present disclosure relates to a
method of treating a subject having a cancer associated with
EGFRvIII expression. The method may comprise, for
example, administering the anti-EGFRvIII antibody or antigen-binding
fragment thereof of the present disclosure to the
subject. Alternatively, the method may comprise administering
an isolated cell population engineered to express
CARs to the subject. The antibody or isolated cell population
may be administered in the form of pharmaceutical
compositions.

In an exemplary embodiment, the isolated cell population
may be autologous to the subject. In another exemplary
embodiment, the isolated cell population may be allogenic
(from an allogenic donor) with respect to the receiving
subject.

In accordance with the present disclosure, the cancer
treated by the method of the present disclosure comprises a
solid tumor.

Treatment of gliomas, such as for example glioblastoma
multiforme is particularly contemplated.

In another exemplary embodiment, the method of the
present disclosure provides treatment of carcinoma, such as
for example and without limitation, breast carcinoma, head
and neck carcinoma or oral carcinoma.

In a further aspect, the present disclosure relates to a kit
comprising at least one antibody or antigen-binding fragment,
nucleic acid molecule or vector of the present disclosure.
Kits that comprise the pharmaceutical composition or
the isolated cell population disclosed herein are also encompassed
by the present disclosure. The kit may further comprise
written instructions for using said isolated cell population
for the treatment of a subject having a neoplasm.

In an exemplary embodiment of the disclosure, kits that
are used for producing an antibody or antigen-binding
fragment thereof may comprise a first vial containing a
nucleic acid or vector encoding a light chain or light chain
variable region and a second vial containing a nucleic acid
or vector encoding a heavy chain or heavy chain variable
region.

Kits comprising nucleic acid molecules encoding CARs
of the present disclosure are particularly contemplated.

A further aspect of the present disclosure relates to a
method of making the antibody or antigen-binding fragment
thereof of the present disclosure. The method may comprise culturing a cell comprising nucleic acids encoding the antibody or antigen-binding fragment so that the antibody or antigen-binding fragment thereof is produced. The method may also involve conjugating the antibody or antigen-binding fragment thereof with a cargo molecule.

Another aspect of the present disclosure relates to a method of manufacturing CAR-expressing cell population. The method may comprise introducing the isolated nucleic acid molecule or the vector disclosed herein into a cell. The isolated nucleic acid molecule may integrate into the genome of the cell.

The nucleic acid molecule or the vector disclosed herein may be introduced into immune cells. The immune cells are then grown ex vivo and transfused to a patient. Upon activation, the transduced immune cells may recognize and kill tumor cells expressing EGFRvIII.

Immune cells of human origin may be used to generate the CAR-expressing cell population of the present disclosure. The immune cells may comprise T-cells, Natural Killer cells, cytotoxic T-cells, regulatory T-cells, and combinations thereof. Particularly contemplated are T-cells (CD4+ T-cells, CD8+ T-cells or a combination thereof) or NK cells.

The CAR-expressing cell population may be isolated and/or substantially purified.

BRIEF DESCRIPTION OF THE DRAWINGS

FIG. 1A-1E: represents histograms obtained using flow cytometry on supernatants of selected hybridomas on U87MG cell lines overexpressing wild type human EGFR (U87WT) or EGFRvIII (U87vIII) as indicated.

FIG. 2: is an alignment between the amino acid sequence of the extracellular domains of wild-type human EGFR (EGFR WT, SEQ ID NO: 2) and EGFRvIII (SEQ ID NO: 91).

FIGS. 3A and 3B: show the results of anti-hEGFRvIII mAbs binding properties to various fragments of the EGFRvIII and WT protein cells displayed on yeast cells (+++ represents 95%+/−5% positive yeast cells which is characterized by positive antibody binding with high affinity; ++ represents 70%+/−20% positive yeast cells which is characterized by positive antibody binding with medium affinity; + represents 30%+/−20% positive yeast cells which is characterized by positive antibody binding with low affinity; (+) represents 5-9% positive yeast cells which is characterized by positive antibody binding with very low affinity; +/− represents less than 5% positive yeast cells which is characterized by ambiguous antibody binding, − represents 0% positive yeast cells which is characterized by no binding; nt=not tested FIG. 4: Schematic illustrating the synthetic assembly and sequence of the 5B7 antigen-binding domain and mouse CD8 hinge (SEQ ID NO: 30) for insertion in CAR vector with the heavy chain portion (underlined), amino acids corresponding to a restriction site (*), linker (double underlined), the light chain portion (underlined).

FIG. 8B: Graph illustrating screening of CAR functionality with EGFRvIII-specific CAR constructs containing hinge elements of varying amino acid length (screening hinge truncations in EGFRvIII-CAR). Jurkat cells electroporated with various CAR constructs which contained hinge elements ranging from very long, L17-CD8h which contains the entire human CD8 hinge domain and an extended glycine linker, to very short, 1CD8h which contains a single C-terminal amino acid from the human CD8-hinge sequence. Jurkat-cells transiently expressing these various CAR constructs were exposed to target cells with (U87-vIII) or without (U87-MG) specific target expression. Target-induced activation of each CAR construct was assessed by examining the level of CD69 expression in CAR-expressing (GFP+) cells using human CD69-specific antibody staining and flow cytometry.

DETAILED DESCRIPTION

Figure 5A:
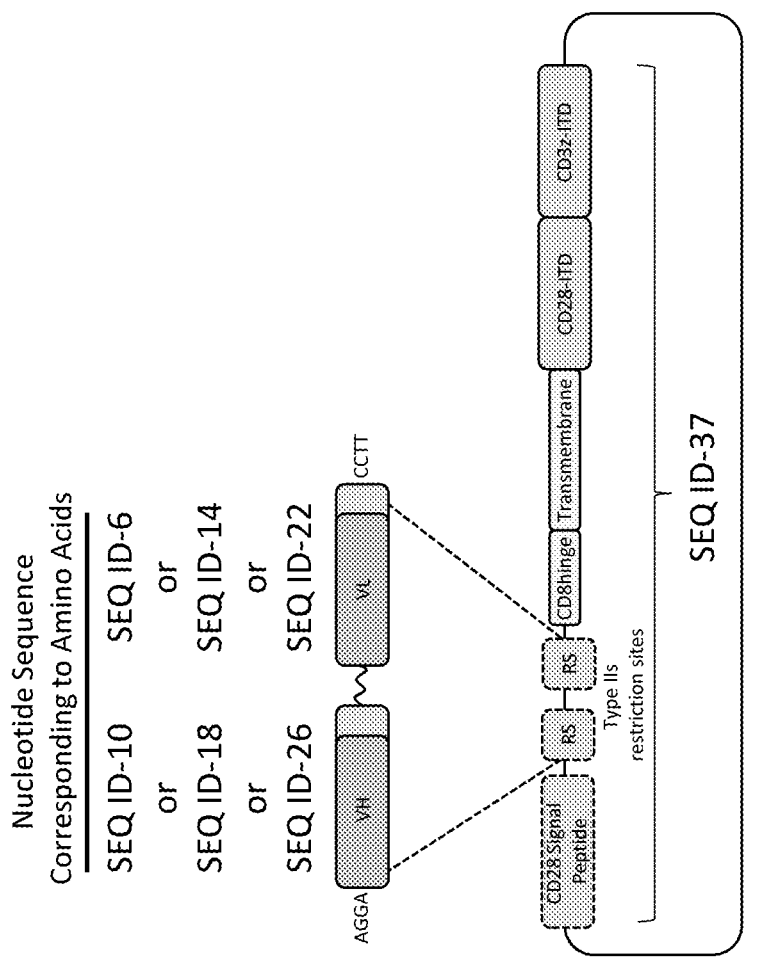
FIG. 5A: Schematic illustrating different elements and DNA sequences of the modular CAR vector (SEQ ID NO:37), representing an example of CAR cloning strategy.

As used herein the term "EGFRvIII" or "vIII" refers to epidermal growth factor receptor variant III.

As used herein the term "EGFR" refers to human epidermal growth factor receptor. The term "wt EGFR", "WT EGFR", "EGFR WT" or "EGFR wt" are used interchangeably and refers to wild-type EGFR.

The use of the terms "a" and "an" and "the" and similar referents in the context of describing the disclosure (especially in the context of the claims) are to be construed to cover both the singular and the plural, unless otherwise indicated herein or clearly contradicted by context.

Unless specifically stated or obvious from context, as used herein the term "or" is understood to be inclusive and covers both "or" and "and".

The term "and/or" where used herein is to be taken as specific disclosure of each of the specified features or components with or without the other.

The terms "comprising", "having", "including", and "containing" are to be construed as open-ended terms (i.e., meaning "including, but not limited to") unless otherwise noted. The term "consisting of" is to be construed as close-ended. The term "consisting essentially of" when used in the context of CDR sequences means that the CDR sequence may be slightly (e.g., +/−1 or 2 aa) longer or shorter.

As used herein the term "native" with respect to a protein such as EGFRvIII or EGFR refers to the natural conformation of the protein and includes proteins that are properly folded and/or functional.

As used herein the term "denatured" with respect to a protein such EGFRvIII or EGFR refers to a protein that has lost its natural conformation and may entail for example, a loss in the tertiary and secondary structure.

As used herein, the term "antibody" encompasses monoclonal antibody, polyclonal antibody, humanized antibody, chimeric antibody, human antibody, domain antibody, multispecific antibody (e.g., bispecific antibodies such as for example a bi-specific T-cell engager) etc. The term "antibody" encompasses molecules that have a format similar to those occurring in nature (e.g., human IgGs, etc.).

As used herein the term "not able to significantly bind a peptide" means that the binding is between 0% and 15% of that observed for the non-mutated EGFRvIII peptide (SEQ ID NO:5).

As used herein the term "antigen-binding domain" refers to the domain of an antibody or of an antigen-binding fragment which allows specific binding to an antigen.

The antigen-binding domain of the present disclosure may comprise for example, at least one complementarity determining region of the antibody heavy chain. In accordance with the present disclosure, the antigen-binding domain may comprise at least two complementarity determining regions of the antibody heavy chain. Further in accordance with the present disclosure, the antigen-binding domain may comprise three complementarity determining regions of antibody heavy chain. The antigen-binding domain may comprise or also comprise at least one complementarity determining region of the antibody light chain. In accordance with the present disclosure, the antigen-binding domain may comprise at least two complementarity determining regions of the antibody light chain. Further in accordance with the present disclosure, the antigen-binding domain may comprise at least three complementarity determining regions of the antibody light chain. The antigen-binding domain may comprise three complementarity determining regions of the light chain and three complementarity determining regions of the heavy chain of the antibody.

An exemplary embodiment of a molecule comprising an antigen-binding domain is an antibody or an antigen-binding fragment thereof.

Another exemplary embodiment of a molecule comprising an antigen-binding domain is a chimeric antigen receptor.

Yet another exemplary embodiment of a molecule comprising an antigen-binding domain is a bi-specific T-cell engager.

Yet a further exemplary embodiment of a molecule comprising an antigen-binding domain is a bispecific killer cell engager.

Another exemplary embodiment of a molecule comprising an antigen-binding domain is a trispecific killer cell engager.

A further exemplary embodiment of a molecule comprising an antigen-binding domain is an antigen-binding fragment such as for example a single chain Fv. In accordance with the present disclosure, the single chain Fv comprises for example, the heavy chain variable region and the light chain variable region of an antibody that specifically binds to EGFRvIII. The heavy chain variable region and the light chain variable region of the antibody may be connected by a linker.

Linker sequences include for example, an amino acid sequence of at least 5 amino acids. Multimers of the pentapeptide $G_4S$ (SEQ ID NO: 88) (e.g., (Gly$_4$Ser), where n is a positive integer of 1 or more) are often used in the engineering of scFvs. Those include for example, a 15-mer $(G_4S)_3$ (SEQ ID NO: 89) found in some of the first scFv fragments (Huston et al., 1988), an 18-mer GGSSRSSSSGGGGSGGGG (SEQ ID NO: 87) (Andris-Widhopf et al., 2011) and the 20-mer $(G_4S)_4$ (SEQ ID NO: 90) (Schaefer et al., 2010). Many other sequences have been proposed, including sequences with added functionalities, e.g. an epitope tag or an encoding sequence containing a Cre-Lox recombination site (Sblattero & Bradbury, 2000) or sequences improving scFv properties, often in the context of particular antibody sequences. The linker of the present disclosure may have the sequence GGGSGGGGSGGGGS (SEQ ID NO:47).

Chimeric Antigen Receptors

The present disclosure relates to chimeric antigen receptors that specifically bind to EGFRvIII and nucleic acid encoding same. The chimeric antigen receptors of the present disclosure comprise an antigen-binding domain of an antibody that specifically binds to EGFRvIII.

The basic structure of chimeric antigen receptors has been described in the literature (e.g., Gacerez, A. T. et al., J Cell Physiol. 231(12): 2590-2598 (2016), Sadelain, M. et al. Cancer Discovery, 3(4): 388-98, (2013), Zhang, C. et al., Biomarker Research, 5:22 (2017)).

Chimeric antigen receptors have an extracellular region (or ectodomain) which comprises an antigen-binding domain and an intracellular region (or endodomain) which comprises the transmembrane domain and the intracytoplasmic domain which comprise intracellular signaling domains of immune response pathways or immune effector function (e.g., cytolytic activity, helper activity including secretion of cytokines).

The general structure of the chimeric antigen receptors of the present disclosure is composed of an antigen-binding domain, a transmembrane domain, an optional costimulatory domain and an intracellular signaling domain.

The antigen-binding domain is generally composed of an antibody's heavy chain variable region and light chain variable region connected via a linker and forming, for example, a single chain (e.g., scFv). The antibody used to generate the CAR construct is selected for its ability to specifically bind to epidermal growth factor receptor variant III (EGFRvIII) while not binding to wild-type EGFR.

The heavy chain variable region may be at the N-terminus of the polypeptide chain, followed by the linker and the light chain variable region. Alternatively, the light chain variable region may be at the N-terminus of the polypeptide chain, followed by the linker and the heavy chain variable region. In some instances, the single chain Fv may also comprises portions of the constant region.

Chimeric antigen receptors may also comprise a hinge region or spacer which connects the antigen-binding domain and the transmembrane domain. The spacer may allow a better presentation of the antigen-binding domain at the surface of the cell.

In accordance with the present disclosure, the spacer may be optional. Alternatively, the spacer may comprise for example, between 1 to 200 amino acid residues, typically between 10 to 100 amino acid residues and more typically between 25 to 50 amino acid residues. The spacer may originate from a human protein.

In accordance with the present disclosure, the spacer or hinge region may be, for example and without limitation a CD8 hinge (e.g., mouse, human CD8) or an IgG hinge (a human immunoglobulin hinge) or combination thereof.

An exemplary embodiment of a linker and hinge combination is provided in SEQ ID NO:81 where the hinge portion is from human CD8.

The transmembrane domain allows the extracellular region of the CAR to be anchored at the cell membrane. The transmembrane domain may be natural or synthetic and usually comprises hydrophobic amino acid residues. The transmembrane domain may be obtained from any naturally occurring protein having a transmembrane domain. The transmembrane domain is particularly selected for its ability to signal to the intracellular domain that the antigen-binding domain has bound to its target.

Exemplary embodiments of transmembrane domains include, for example and without limitation, the alpha, beta or CD3zeta chain of the T-cell receptor complex, CD28, CD27, CD3 epsilon, CD45, CD4, CD5, CD8, CD9, CD16, CD22, CD33, CD37, CD64, CD80, CD86, CD134, CD137, CD154.

In some embodiments, the transmembrane domain may include at least the transmembrane region(s) of, e.g., KIRDS2, OX40, CD2, CD27, LFA-1 (CD 11a, CD18), ICOS (CD278), 4-1BB (CD137). GITR, CD40, BAFFR, HVEM (LIGHTR), SLAMF7, NKp80 (KLRF1). NKp44, NKp30, NKp46, CD 160, CD 19, IL2R beta, IL2R gamma, IL7R a, ITGA1, VLA1, CD49a, ITGA4, IA4, CD49D, ITGA6, VLA-6, CD49f, ITGAD, CD1d, ITGAE, CD103, ITGAL, CD11a, LFA-1, ITGAM, CD11b, ITGAX, CD11c, ITGB 1, CD29, ITGB2, CD18, LFA-1, ITGB7, TNFR2, DNAM1 (CD226). SLAMF4 (CD244, 2B4), CD84, CD96 (Tactile). CEACAM1, CRT AM, Ly9 (CD229), CD160 (BY55). PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKG2D, NKG2C.

A particular embodiment of transmembrane domain is the transmembrane domain of CD28.

In accordance with the present disclosure, the chimeric antigen receptors may comprise one or more intracellular signaling domain derived from CD3 zeta, CD3 gamma, CD3 delta, CD3 epsilon, common FcR gamma (FCERIG), FcR beta (Fc Epsilon Rib), CD79a, CD79b, Fcgamma Rlla, DAP10, or DAP12.

Chimeric antigen receptors may also optionally comprise at least one costimulatory domain.

In accordance with the present disclosure, the costimulatory domain may be, for example, from CD28, CD27, 4-1BB, OX40, CD7, B7-1 (CD80), B7-2 (CD86), CD30, CD40, PD-1, ICOS, lymphocyte function-associated antigen-1 (LFA-1), CD2, LIGHT, NKG2C, B7-H3, a ligand that specifically binds with CD83, CDS, ICAM-1, GITR, BAFFR, HVEM (LIGHTR), SLAMF7, NKp80 (KLRF1), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD1d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, IPO-3), BLAME (SLAMF8), SELPLG (CD162), LTBR, LAT, GADS, SLP-76, PAG/Cbp, NKp44, NKp30, NKp46, and NKG2D or a combination thereof.

In order to be targeted to the secretory pathway, the chimeric antigen receptor may also comprise a signal peptide such as, for example, a signal peptide of CD28 or any other signal peptide suitable for immune cells. The signal peptide is cleaved (cleavable).

The antigen-binding fragments of the present disclosure may comprise human or humanized framework amino acid sequences.

Antibodies or Antigen-Binding Fragments

Typically, an antibody is constituted from the pairing of two light chains and two heavy chains. Different antibody isotypes exist, including IgA, IgD, IgE, IgG and IgM. Human IgGs are further divided into four distinct subgroups namely; IgG1, IgG2, IgG3 and IgG4. Therapeutic antibodies are generally developed as IgG1 or IgG2.

In an exemplary embodiment, the antibody or antigen-binding fragment of the present disclosure may comprise, for example, a human IgG1 constant region. In another exemplary embodiment, the antibody or antigen-binding fragment of the present disclosure may comprise, for example, a human IgG2 constant region.

The light chain and heavy chain of human antibody IgG isotypes each comprise a variable region having 3 hypervariable regions named complementarity determining regions (CDRs). The light chain CDRs are identified herein as CDRL1 or L1, CDRL2 or L2 and CDRL3 or L3. The heavy chain CDRs are identified herein as CDRH1 or H1, CDRH2 or H2 and CDRH3 or H3. Complementarity determining regions are flanked by framework regions (FR) in the order: FR1-CDR1-FR2-CDR2-FR3-CDR3-FR4. CDRs may be identified using for example, the Kabat and Chotia definitions (Kabat, J. Immunol. 1991, Chotia and Lesk 1987). However, others (Abhinandan and Martin, 2008) have used modified approaches based loosely on Kabat and Chotia resulting in the delineation of shorter CDRs. Lefranc also discloses the IMGT numbering scheme for CDRs (Lefranc, M.-P., The Immunologist, 7, 132-136 (1999)).

The overall binding affinity of the antibody or antigen-binding fragment thereof is often dictated by the sequence of the CDRs. The framework regions may also play a role in the proper positioning and alignment in three dimensions of the CDRs for optimal antigen-binding.

As used herein an "antigen-binding fragment" refers to a fragment of an antibody that may be obtained by enzymatic digestion of an antibody, by recombinant DNA technology and the like. Antigen-binding fragments thereof of the present disclosure encompass molecules having an antigen-binding domain comprising amino acid residues that confer specific binding to an antigen (e.g., one or more CDRs).

Examples of antigen-binding fragments encompassed by the present disclosure include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody (e.g. scFv), (v) a dAb fragment (Ward et al., (1989) Nature 341:544-546), which consists of a $V_H$ domain; and (vi) an isolated complementarity determining region (CDR), e.g., $V_H$ CDR3.

Although the two domains of the Fv fragment, $V_L$ and $V_H$, are coded for by separate genes, they can be joined, using recombinant methods, by a synthetic linker that enables them to be made as a single polypeptide chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883).

Single chain antibodies (e.g., single domain), diabody, minibody, nanobody and the like are encompassed within the term "antigen-binding fragment". These antibody fragments are obtained using conventional techniques known to those with skill in the art, and the fragments are screened for activity in the same manner as for intact antibodies.

Particular embodiments of antigen-binding fragments may include for example, a scFv, a Fab, a Fab' or a (Fab')$_2$.

The term "humanized antibody" encompasses fully humanized (i.e., frameworks are 100% humanized) and partially humanized sequences (e.g., at least one variable region contains one or more amino acids from a human antibody, while other amino acids are amino acids of a non-human parent antibody). Typically, a "humanized antibody or antigen-binding fragment" contains CDRs of a non-human parent antibody (e.g., mouse, rat, rabbit, non-human primate, etc.) and frameworks that are identical to those of a natural human antibody or of a human antibody consensus. In such instance, those "humanized antibodies or antigen-binding fragments" are characterized as fully humanized. A "humanized antibody or antigen-binding fragment" may also contain one or more amino acid substitutions that have no correspondence to those of the human antibody or human antibody consensus. Such substitutions include, for example, back-mutations (e.g., re-introduction of non-human amino acids) that may preserve the antibody characteristics (e.g., affinity, specificity etc.). Such substitutions are usually in the framework region. A "humanized antibody or antigen-binding fragment" usually also comprise a constant region (Fc) or a portion thereof which is typically that of a human antibody. Typically, the constant region of a "humanized antibody or antigen-binding fragment" is identical to that of a human antibody. A humanized antibody may be obtained by CDR grafting (Tsurushita et al, 2005; Jones et al, 1986; Tempest et al, 1991; Riechmann et al, 1988; Queen et al, 1989). Such antibody is considered as fully humanized.

The term "chimeric antibody" refers to an antibody having a constant region from an origin distinct from that of the parent antibody. The term "chimeric antibody" encompasses antibodies having a human constant region. Typically, a "chimeric antibody" is composed of variable regions originating from a mouse antibody and of human constant regions.

The term "hybrid antibody" refers to an antibody comprising one of its heavy or light chain variable region (its heavy or light chain) from a certain type of antibody (e.g., humanized) while the other of the heavy or light chain variable region (the heavy or light chain) is from another type (e.g., murine, chimeric).

Antibodies and/or antigen-binding fragments of the present disclosure may originate, for example, from a mouse, a rat or any other mammal or from other sources such as through recombinant DNA technologies. Antibodies or antigen-binding fragment of the present disclosure may include for example, a synthetic antibody, a non-naturally occurring antibody, an antibody obtained following immunization of a non-human mammal etc.

Antibodies or antigen-binding fragments thereof of the present disclosure may be isolated and/or substantially purified.

Variants

The present disclosure also encompasses variants of the antigen-binding agents described herein. Variant of the present disclosure include those having a variation in their amino acid sequence, e.g., in one or more CDRs, in one or more framework regions and/or in the constant region. Variant included in the present disclosure are those having, for example, similar or improved binding affinity in comparison with an original antigen-binding agent.

Exemplary variants encompassed by the present disclosure are those which may comprise an insertion, a deletion or an amino acid substitution (conservative or non-conservative). These variants may have at least one amino acid residue in its amino acid sequence removed and a different residue inserted in its place.

More particularly, variants encompassed by the present disclosure include those having a light chain variable region and/or a heavy chain variable region having at least 80% sequence identity with the light chain variable region and/or a heavy chain variable region of the antibodies or antigen-binding fragments, CARs, BiTEs, BiKEs or TriKEs disclosed herein. The CDRs of the variants of the present disclosure may be identical to those of the antibodies or antigen-binding fragments, CARs, BiTEs, BiKEs or TriKEs disclosed herein.

Also encompassed by the present disclosure are variants having CDRs amino acid residues that are identical and framework regions that are at least 80% sequence identical to those of the antigen-binding domain, antibody or antigen-binding fragment disclosed herein.

Conservative substitutions may be made by exchanging an amino acid residue (of a CDR, variable chain, framework region or constant region, etc.) from one of the groups listed below (group 1 to 6) for another amino acid of the same group.

Other exemplary embodiments of conservative substitutions are shown in Table A.

(group 1) hydrophobic: norleucine, methionine (Met), Alanine (Ala), Valine (Val), Leucine (Leu), Isoleucine (Ile)

(group 2) neutral hydrophilic: Cysteine (Cys), Serine (Ser), Threonine (Thr)

(group 3) acidic: Aspartic acid (Asp), Glutamic acid (Glu)

(group 4) basic: Asparagine (Asn), Glutamine (Gln), Histidine (His), Lysine (Lys), Arginine (Arg)

(group 5) residues that influence chain orientation: Glycine (Gly), Proline (Pro); and (group 6) aromatic: Tryptophan (Trp), Tyrosine (Tyr), Phenylalanine (Phe)

Non-conservative substitutions will entail exchanging a member of one of these groups for another.

TABLE A

| Amino acid substitution | | |
|---|---|---|
| Original residue | Exemplary substitution | Conservative substitution |
| Ala (A) | Val, Leu, Ile | Val |
| Arg (R) | Lys, Gln, Asn | Lys |
| Asn (N) | Gln, His, Lys, Arg, Asp | Gln |
| Asp (D) | Glu, Asn | Glu |
| Cys (C) | Ser, Ala | Ser |
| Gln (Q) | Asn; Glu | Asn |
| Glu (E) | Asp, Gln | Asp |
| Gly (G) | Ala | Ala |
| His (H) | Asn, Gln, Lys, Arg, | Arg |
| Ile (I) | Leu, Val, Met, Ala, Phe, norleucine | Leu |
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Leu, Val, Ile, Ala, Tyr | Tyr |
| Pro (P) | Ala | Ala |
| Ser (S) | Thr | Thr |
| Thr (T) | Ser | Ser |
| Trp (W) | Tyr, Phe | Tyr |
| Tyr (Y) | Trp, Phe, Thr, Ser | Phe |
| Val (V) | Ile, Leu, Met, Phe, Ala, norleucine | Leu |

Percent identity is indicative of amino acids which are identical in comparison with the original peptide and which may occupy the same or similar position. Percent similarity will be indicative of amino acids which are identical and those which are replaced with conservative amino acid substitution in comparison with the original peptide at the same or similar position.

Generally, the degree of similarity and identity between variable chains has been determined herein using the Blast2 sequence program (Tatiana A. Tatusova, Thomas L. Madden (1999), "Blast 2 sequences—a new tool for comparing protein and nucleotide sequences", FEMS Microbiol Lett. 174:247-250) using default settings, i.e., blastp program, BLOSUM62 matrix (open gap 11 and extension gap penalty 1; gapx dropoff 50, expect 10.0, word size 3) and activated filters.

Variants of the present disclosure therefore comprise those which may have at least 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity with an original sequence or a portion of an original sequence.

Nucleic Acids, Vectors and Cells

As used herein, the term "nucleic acid' refers to RNA, DNA, cDNA and the like.

The present disclosure encompasses nucleic acids capable of encoding any of the CDRs, light chain variable regions, heavy chain variable regions, light chains, heavy chains, scFvs antibodies or antigen-binding fragments, CARs, BiTEs, BiKEs or TriKEs or variants described herein.

Nucleic acid molecules encoding CARs, BiTEs, BiKEs or TriKEs are introduced into immune cells where they are expressed. Nucleic acids encoding CARs, BiTEs, BiKEs or TriKEs may be delivered by transduction systems such as for example, using viral systems (from lentiviruses, adenoviruses, adeno-associated viruses, etc.) or non-viral systems (e.g., transposon). Exemplary system involving transposons includes the Sleeping Beauty transposon system and the piggyBac transposon system. Gene editing system may also be used including, without limitation, the CRISPR/cas system, the Zinc finger nuclease system, the Transcription Activator-Like Effector Nucleases (TALENs) system. Nucleic acids (e.g., RNA or DNA) may be delivered by other means such as by liposomes, naked DNA, polymers, electroporation etc.

Due to the inherent degeneracy of the genetic code, other nucleic acid sequences that encode the same amino acid sequence may be produced and used to express the antibody or antigen-binding fragments thereof of the present disclosure. The nucleotide sequences may be engineered using methods generally known in the art in order to alter the nucleotide sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth.

In yet another aspect, the present disclosure relates to a vector or vectors comprising the nucleic acids described herein.

In accordance with the present disclosure, the vector or vectors may be an expression vector(s).

Further in accordance with the present disclosure, the vector may be a viral vector. Exemplary embodiments of viral vectors include lentiviral vectors, adenoviral vectors or adeno-associated viral vectors.

The expression vector usually contains the elements for transcriptional and translational control of the inserted coding sequence in a particular host. These elements may include regulatory sequences, such as enhancers, constitutive and inducible promoters, and 5' and 3' un-translated regions. Exemplary embodiments of promoter used to drive CAR construct expression in T cells includes the EF1a promoter. Other exemplary embodiments of promoters include constitutively active viral promoters such as for example, the immediate early cytomegalovirus (CMV) promoter, simian virus 40 (SV40) early promoter, mouse mammary tumor virus (MMTV) promoter, human immunodeficiency virus (HIV) long terminal repeat (LTR), Rous sarcoma virus (RSV) promoter.

Methods that are well known to those skilled in the art may be used to construct such expression vectors. These methods include in vitro recombinant DNA techniques, synthetic techniques, and in vivo genetic recombination.

In order to make the antibodies or antigen-binding fragments of the present disclosure, a vector or a set of vectors expressing the light chain and heavy chain are introduced into a cell.

The present disclosure encompasses vectors or a set of vectors where the light chain variable region and the heavy chain variable region of the antibody or antigen-binding fragment thereof are encoded by the same nucleic acid molecule (e.g., same vector) or by separate nucleic acid molecules (e.g., separate vectors).

In another aspect the present disclosure relates to an isolated cell which may comprise the nucleic acids, vectors, antibodies or antigen-binding fragment, CARs, BiTEs, BiKEs or TriKEs described herein.

Yet another aspect of the present disclosure relates to an isolated host cell which expresses the antibody or antigen-binding fragment, CAR, BiTE, BiKE or TriKE of the present disclosure. The isolated host cell for CAR, BiTE, BiKEs or TriKE expression may be an immune cell such as for example and without limitation, T cells, Natural Killer (NK) cells, cytotoxic T cells, or regulatory T cells.

The present disclosure also relates to a cell population engineered to express the CAR, BiTE, BiKE or TriKE of the present disclosure. The cell population may be homogenous or heterogenous. In accordance with the present disclosure, the cell population may comprise T cells (CD4+ T-cells, CD8+ T-cells or a combination thereof), Natural Killer (NK) cells, cytotoxic T cells, regulatory T cells, and combinations thereof. In accordance with the present disclosure the cell population may be autologous. In accordance with the present disclosure the cell population may be allogenic.

As used herein the term "autologous" refers to material derived from the same individual.

The term "allogeneic" refers to material derived from a different subject of the same species but that is genetically distinct.

As used herein, the term "heterogenous" with reference to a cell population means that the cell population either express different chimeric antigen receptors or that the cell population comprises different types of cells.

As used herein, the term "homogenous" with reference to a cell population means that the cell population either express the same chimeric antigen receptors or that the cell population comprises the same type of cells.

The present disclosure also encompasses complement of the nucleic acids disclosed herein. It is to be understood herein that nucleic acid molecules comprising at least a portion complementary to the nucleic acid sequence disclosed herein are also encompassed by the present disclosure. Such complementary nucleic acid molecules may be used, for example, for gene amplification or detection of the nucleic acid molecule of the present disclosure and include probes or primers.

Production of Cells Expressing Chimeric Antigen Receptors

Methods of manufacturing or of producing immune cells expressing chimeric antigen receptors, bi-specific T-cell engagers, bispecific killer cell engagers or trispecific killer cell engagers.

Immune cells of human origin may particularly be used to generate the CAR-expressing cell population of the present disclosure. The immune cells may comprise T-cells (e.g., $CD4^+$ or $CD8^+$), Natural Killer cells, cytotoxic T-cells, regulatory T-cells, and combinations thereof. Particularly contemplated are T-cells or NK cells.

Immune cells are first isolated from a subject by various methods known to a person skilled in the art. For example, peripheral blood mononuclear cells (PBMCs) may be isolated from a subject by leukaphoresis. T-cells may be enriched and washed to separate them from the leukocytes. The different T cell subsets may be separated using beads conjugated with specific antibody or markers. CAR-T cells are often generated from the $CD3^+$ population. T-cells are activated by various methods including for example, by antigen-presenting cells, with specific antibodies and the like (methods reviewed in Wang, X et al., Molecular Therapy—Oncolytics, 3:16015, 2016).

The method may comprise introducing the isolated nucleic acid molecule or the vector disclosed herein into the immune cells such that the nucleic acid integrates into the genome of the cell. The cells may be transduced using viral vectors or by other means and expanded. For example, lentiviral vectors are used to transduce immune cells with CAR-expression by exposing cells directly to viral vector containing supernatant media overnight. Cells are then assessed for transduction using a fluorescent marker included in the CAR-expressing lentiviral backbone.

Following purification and quality control steps, CAR-expressing immune cells are provided to a subject in need. The subject in need may be, for example, the initial donor of the immune cells.

Production of the Antibodies or Antigen-Binding Fragments in Cells

The antibodies that are disclosed herein can be made by a variety of methods familiar to those skilled in the art including hybridoma methodology or recombinant DNA methods.

Conventional hybridoma technology entails immunizing a rodent with an antigen, isolating and fusing spleen cells with myeloma cells lacking HGPRT expression and selecting hybrid cells by hypoxanthine, aminopterin and thymine (HAT) containing media. Hybridoma are screened to identify those producing antibodies that are specific for a given antigen. The hybridoma is expanded and cloned. The nucleic acid sequence of the light chain and heavy chain variable regions is obtained by standard sequencing methodology and expression vectors comprising the light chain and heavy chain nucleic acid sequence of an antibody are generated.

For recombinant expression of antibodies, host cells are transformed with a vector or a set of vectors comprising the nucleic acid sequence of the light chain and heavy chain of the antibody or antigen-binding fragment thereof (on the same vector or separate vectors).

For long-term production of recombinant proteins in mammalian systems, stable expression in cell lines may be effected. For example, nucleotide sequences able to encode any one of a light and heavy immunoglobulin chains described herein may be transformed into cell lines using expression vectors that may contain viral origins of replication and/or endogenous expression elements and a selectable or visible marker gene on the same or on a separate vector. The disclosure is not to be limited by the vector or host cell employed. In certain embodiments of the present disclosure, the nucleotide sequences able to encode any one of a light and heavy immunoglobulin chains described herein may each be ligated into a separate expression vector and each chain expressed separately. In another embodiment, both the light and heavy chains able to encode any one of a light and heavy immunoglobulin chains described herein may be ligated into a single expression vector and expressed simultaneously.

Immunological methods for detecting and measuring the expression of polypeptides are known in the art. Examples of such techniques include enzyme-linked immunosorbent assays (ELISAs), radioimmunoassays (RIAs), fluorescence activated cell sorting (FACS) or flow cytometry. Those of skill in the art may readily adapt these methodologies to the present disclosure.

Different host cells that have specific cellular machinery and characteristic mechanisms for post-translational activities (e.g., Chinese Hamster Ovary (CHO), HeLa, MDCK, HEK293, and W138) are available commercially and from the American Type Culture Collection (ATCC) and may be chosen to ensure the correct modification and processing of the expressed polypeptide.

Typically, antibody or antigen-binding fragments thereof are produced in CHO cells, NS0 murine myeloma cells, PER.C6® human cells.

The present disclosure relates to a method of making an antibody or an antigen-binding fragment thereof comprising expressing the light chain and heavy chain of the antibody or antigen-binding fragment of the present disclosure in cultured cells.

The method may further comprise purifying or isolating the antibody or antigen-binding fragment of the present disclosure. The method may also further comprise conjugating the antibody or antigen-binding fragment of the present disclosure to a cargo molecule such as a therapeutic or detectable moiety.

Antibody Conjugates

The antibody or antigen-binding fragment thereof of the present disclosure may be linked to a cargo molecule. Exemplary embodiments of cargo molecules include without limitation a therapeutic moiety a detectable moiety, a polypeptide (e.g., peptide, enzyme, growth factor), a polynucleotide, liposome, nanoparticle, nanowire, nanotube, quantum dot, etc.

More particularly, the antibody or antigen-binding fragment thereof of the present disclosure may be conjugated with a therapeutic moiety. The therapeutic moiety is usually attached to the antibody via a linker which may be cleavable or non-cleavable.

Included amongst the list of therapeutic moiety are cytotoxic agents, cytostatic agents, anti-cancer agents (chemotherapeutics) and radiotherapeutics (e.g. radioisotopes).

Exemplary embodiments of cytotoxic agents include, without limitation, alpha-amanitine, cryptophycin, duocarmazine, duocarmycin, chalicheamicin, deruxtecan, pyrrolobenzodiazepine (PBD), dolastatins, pseudomonas endotoxin, ricin, auristatins (e.g., monomethyl auristatin E, monomethyl auristatin F), maytansinoids (e.g., mertansine) and analogues.

Exemplary embodiments of radiotherapeutics include without limitation, Yttrium-90, Scandium-47, Rhenium-186, Iodine-131, Iodine-125, and many others recognized by those skilled in the art (e.g., lutetium (e.g., $Lu^{177}$), bismuth (e.g., $Bi^{213}$), copper (e.g., $Cu^{67}$)), astatine-211 (211At) actinium 225 ($Ac^{225}$).

Exemplary embodiments of chemotherapeutics include, without limitation, 5-fluorouracil, adriamycin, irinotecan, taxanes, carboplatin, cisplatin, etc.

The antibody or antigen-binding fragment of the present disclosure may also be conjugated with a detectable moiety (i.e., for detection or diagnostic purposes).

A "detectable moiety" comprises agents detectable by spectroscopic, photochemical, biochemical, immunochemical, chemical and/or other physical means. A detectable moiety may be coupled either directly and/or indirectly (for example via a linkage, such as, without limitation, a DOTA or NHS linkage) to antibodies and antigen-binding fragments thereof of the present disclosure using methods well known in the art. A wide variety of detectable moieties may be used, with the choice depending on the sensitivity required, ease of conjugation, stability requirements and available instrumentation. A suitable detectable moiety include, but is not limited to, a fluorescent label, a radioactive label (for example, without limitation, $^{125}$I, In$^{111}$, Tc$^{99}$, I$^{131}$ and including positron emitting isotopes for PET scanner etc), a nuclear magnetic resonance active label, a luminescent label, a chemiluminescent label, a chromophore label, an enzyme label (for example and without limitation horseradish peroxidase, alkaline phosphatase, etc.), quantum dots and/or a nanoparticle. Detectable moiety may cause and/or produce a detectable signal thereby allowing for a signal from the detectable moiety to be detected.

Pharmaceutical Compositions

The present disclosure relates to a pharmaceutical composition which may comprise the antibodies or antigen binding fragments thereof, BiTEs, BiKEs or TriKEs of the present disclosure. The pharmaceutical composition may comprise, for example, diluents and/or other components such as immunomodulatory antibodies including but not limited to immune checkpoint blocking antibodies, cytokines or chemokines.

The present disclosure relates to a pharmaceutical composition which may comprise a cell population engineered to express CARs, BiTEs, BiKEs or TriKEs of the present disclosure. The pharmaceutical composition may comprise, for example, diluents and/or other components such as immunomodulatory antibodies including but not limited to immune checkpoint blocking antibodies, cytokines or chemokines.

The present disclosure also relates to pharmaceutical compositions comprising the antibodies or antigen-binding fragments (conjugated or not) disclosed herein.

In addition to the active ingredients, a pharmaceutical composition may contain pharmaceutically acceptable carriers comprising without limitation, water, PBS, salt solutions, gelatins, oils, alcohols, and other excipients and auxiliaries that facilitate processing of the active compounds into preparations that may be used pharmaceutically. In instances where the pharmaceutical composition comprises live cells (e.g., human NK cell lines) the preparation may be irradiated. Pharmaceutical compositions may also contain, without limitation; dextran, dextrose, dimethylsulfoxide (DMSO), human serum albumin, PlasmaLyte A™, sodium chloride As used herein, "pharmaceutical composition" means therapeutically effective amounts of the agent together with pharmaceutically acceptable diluents, preservatives, solubilizers, emulsifiers, adjuvant and/or carriers. A "therapeutically effective amount" as used herein refers to that amount which provides a therapeutic effect for a given condition and administration regimen. Such compositions are liquids or lyophilized or otherwise dried formulations and include diluents of various buffer content (e.g., Tris-HCl, acetate, phosphate), pH and ionic strength, additives such as albumin or gelatin to prevent absorption to surfaces, detergents (e.g., Tween 20, Tween 80, Pluronic F68, bile acid salts). Solubilizing agents (e.g., glycerol, polyethylene glycerol), antioxidants (e.g., ascorbic acid, sodium metabisulfite), preservatives (e.g., thimerosal, benzyl alcohol, parabens, dimethylsulfoxide), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polyglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils). Also comprehended by the disclosure are particulate compositions coated with polymers (e.g., poloxamers or poloxamines).

Other embodiments of the compositions of the disclosure incorporate particulate forms protective coatings, protease inhibitors or permeation enhancers for various routes of administration, including parenteral, pulmonary, nasal, oral, vaginal, rectal routes. In one embodiment the pharmaceutical composition is administered parenterally, paracancerally, transmucosally, transdermally, intramuscularly, intravenously, intradermally, subcutaneously, intraperitonealy, intraventricularly, intracranially and intratumorally.

Further, as used herein "pharmaceutically acceptable carrier" or "pharmaceutical carrier" are known in the art and include, but are not limited to, 0.01-0.1 M or 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

For any compound, the therapeutically effective dose may be estimated initially either in cell culture assays or in animal models such as mice, rats, rabbits, dogs, or pigs. An animal model may also be used to determine the concentration range and route of administration. Such information may then be used to determine useful doses and routes for administration in humans. These techniques are well known to one skilled in the art and a therapeutically effective dose refers to that amount of active ingredient that ameliorates the symptoms or condition. Therapeutic efficacy and toxicity may be determined by standard pharmaceutical procedures in cell cultures or with experimental animals, such as by calculating and contrasting the ED$_{50}$ (the dose therapeutically effective in 50% of the population) and LD$_{50}$ (the dose lethal to 50% of the population) statistics. Any of the therapeutic compositions described above may be applied to any subject in need of such therapy, including, but not limited to, mammals such as dogs, cats, cows, horses, rabbits, monkeys, and humans.

Pharmaceutical compositions comprising cells may be administered by infusion (e.g., by intravenous route, intracerebral injection or other routes). Pharmaceutical compositions comprising antibodies of the present disclosure may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In certain instances, the CAR cell population may be administered concurrently in combination with other treatments given for the same condition including for example anti-cancer agents. Exemplary embodiments of anti-cancer agents include for example and without limitation, therapeutic antibodies, immunomodulators (immune checkpoint blocking antibodies), anti-mitotics (e.g., taxanes), platinum-based agents (e.g., cisplatin), DNA damaging agents (eg. Doxorubicin) and other anti-cancer therapies that are known to those skilled in the art.

Additional aspects of the disclosure relate to kits which may include vial(s) containing one or more nucleic acid encoding the CARs, BiTEs, BiKEs, TriKEs or antibodies or antigen-binding fragments described herein.

Methods of Use

Aspects of the disclosure comprise administering antibodies or antigen binding fragments thereof, CAR, BiTE, BiKE or TriKE molecules to a subject in need.

Other aspects of the disclosure comprise administering immune cells engineered to express the CAR, BiTE, BiKE or TriKE molecules to a subject in need.

The CAR, BiTE, BiKE or TriKE constructs of the present disclosure may be used to re-target engineered immune cells towards EGFRvIII-positive tumors.

The engineered immune cells may be administered to a subject in need.

In accordance with an aspect of the present disclosure, immune cells are isolated from the subject, engineered to express the CAR, BiTE, BiKE or TriKE construct and re-administered to the same subject.

As used herein the term "subject" encompasses humans and animals such as non-human primates, cattle, rabbits, mice, rats, sheep, goats, horses, birds, etc. The term "subject" particularly encompasses humans.

Subjects in need which would benefit from treatment include humans having tumor cells expressing EGFRvIII. More particularly, the immune cells engineered to express the CAR, BiTE, BiKE or TriKE construct disclosed herein may be administered to a subject suspected of having glioblastoma multiforme (GBM). Subjects in need also encompass those having or suspected of having carcinomas, such as breast carcinoma, ovarian carcinoma, prostate carcinoma, or non-small cell lung carcinomas.

The term "treatment" for purposes of this disclosure refers to both therapeutic treatment and prophylactic or preventative measures, wherein the object is to slow down (lessen) the targeted pathologic condition or disorder. Those in need of treatment include those already with the disorder as well as those prone to have the disorder or those in whom the disorder is to be prevented. Particularly, subjects in need include subjects with an elevated level of one or more cancer markers.

The present disclosure more particularly relates to a method of treating a subject having or suspected of having cancer by administering a cell population expressing the chimeric antigen receptor or the antibody or antigen-binding fragment thereof disclosed herein.

The cell population expressing the chimeric antigen receptor, or the antibody or antigen-binding fragment thereof may be administered as a pharmaceutical composition either alone or in combination with other anti-cancer drugs.

Other aspects of the disclosure relate to a method for detecting EGFRvIII, the method may comprise contacting a cell expressing EGFRvIII, or a sample (biopsy, a body fluid such as serum, plasma, urine etc.) comprising or suspected of comprising EGFRvIII with the antibody or antigen-binding fragments described herein and measuring binding. The sample may originate from a mammal (e.g., a human) which may have cancer (e.g., glioblastoma multiforme or carcinoma) or may be suspected of having such cancer. The sample may be a tissue sample obtained from the mammal or a cell culture supernatant.

In accordance with the disclosure the sample may be a serum sample, a plasma sample, a blood sample or ascitic fluid obtained from the mammal.

Further scope, applicability and advantages of the present disclosure will become apparent from the non-restrictive detailed description given hereinafter. It should be understood, however, that this detailed description, while indicating exemplary embodiments of the disclosure, is given by way of example only, with reference to the accompanying drawings.

EXAMPLES

Example 1: Generation of EGFRvIII Specific Monoclonal Antibodies

Monoclonal antibodies (mAb) against EGFRvIII were generated by immunizing mice with the extracellular domain of recombinant proteins.

Immunizations

Mice were bled (pre-immune serum) and injected intraperitoneally and subcutaneously with 100 µg of recombinant EGFRvIII protein emulsified in Titermax adjuvant (Cedarlane Labs, Burlington, ON) at day 0 and in PBS without adjuvant at day 22. Blood was collected in microvette CB 300Z (Sarstedt, Montreal, QC) at day 29, and serum was stored at −20° C. until further use. ELISA (serum titer determination)

Pre- and post-immune sera titers of animals were assessed by ELISA on recombinant EGFRvIII protein. Unless otherwise stated, all incubations were performed at room temperature. Briefly, half-area 96-well plates (Costar #3690) were coated with 25 µl per well of immunogen at 5 µg/ml in PBS and incubated overnight at 4° C. Microplates were washed three times in PBS and blocked for 30 min with PBS containing 1% bovine serum albumin (BSA, Sigma Cat #A7030). Blocking buffer was removed and 25 µl of serial dilutions of sera samples were added. After a 2-h incubation, microplates were washed 4 times with PBS-TWEEN™ 20 0.05% and 25 µl of a ⅕,₀₀₀ dilution of alkaline phosphatase conjugated F(ab')'₂ goat anti-mouse IgG (H+L, #115-056-062, Jackson Immunoresearch, Cedarlane, Burlington, ON) in blocking buffer was added. After a 1-h incubation, microplates were washed 4 times and 25 µl of p-nitrophenyl phosphate (pNPP) substrate (Sigma-Aldrich Canada Co., Oakville, ON) at 1 mg/ml in carbonate buffer at pH 9.6 was added and further incubated for 30 min. Absorbance was read at 405 nm using a SpectraMax 340 PC plate reader (Molecular Devices, Sunnyvale, CA). All pre-immune bleeds were negative and all post-immune bleeds were very strong (titer above $\frac{1}{51200}$) on recombinant protein.

Generation of Hybridomas

Mice received a final boost of 100 µg of recombinant EGFRvIII protein and their spleen was harvested 3 to 4 days later. All manipulations were done under sterile conditions. Spleen cells were harvested in Iscove's Modified Dulbecco's medium (IMDM, Gibco Cat. #31980-030) and fused to NS0 myeloma cell line using electrofusion protocol.

Electrofusion Protocol

Spleen cells and myeloma cells were washed separately in IMDM. Cells were washed in Isoosmolar buffer (Eppendorf cat #4308070536), then in Cytofusion Medium C (BTX cat #47-0001). Myeloma and lymphocytes were mixed together at a 1:1 ratio and fused using an ECM 2001 Cell Fusion System (BTX, Harvard Bioscience Inc.) following manufacturer's instructions.

Following fusion, cells were suspended at a concentration of $2\text{-}4\times10^5$ input myeloma cells per ml in HAT selection medium (IMDM containing 20% heat inactivated FBS, penicillin-streptomycin (Sigma Cat #P7539), 1 ng/ml mouse IL-6 (Biolegend Cat #575706), HAT media supplement (Sigma Cat #H0262) and L-glutamine (Hy-Clone Cat #SH30034.01) and incubated at 37° C., 5% $CO_2$. The next day, hybridoma cells were washed and suspended at a concentration of $2\text{-}5\times10^5$ input myeloma cells per ml in semi-solid medium D (StemCell Technologies Cat. #03804) supplemented with 5% heat inactivated FBS, 1 ng/ml mouse IL-6 and 10 µg/ml FITC-F(ab')$_2$ Goat anti-mouse IgG Fc gamma specific (Jackson #115-096-071). The cell mixture was plated in Omnitray dish (Nunc cat #242811) and further incubated for 6-7 days at 37° C., 5% $CO_2$. Fluorescent secretor clones were then transferred using a mammalian cell clone picker (ClonepixFL™, Molecular Devices) into sterile 96-w plates (Costar #3595) containing 200 µl of IMDM supplemented with 20% heat inactivated FBS, penicillin-streptomycin, 1 ng/ml mouse IL-6, HT media supplement (Sigma Cat #H0137) and L-glutamine and incubated for 2-3 days at 37° C., 5% $CO_2$.

Five thousand (5000) hybridoma supernatants from seven (7) fusion experiments were screened by ELISA using recombinant EGFRvIII or EGFR wild-type proteins to detect specific binders. To this end, half-area 96-well plates (Costar #3690) were coated with 25 µl per well of immunogen at 5 µg/ml in PBS and incubated overnight at 4° C. Microplates were washed three times in PBS and blocked for 30 min with PBS containing 1% bovine serum albumin (BSA, Sigma Cat #A7030). Blocking buffer was removed and 25 µl of hybridoma supernatant were added. After a 2-h incubation, microplates were washed 4 times with PBS-TWEEN™ 20 0.05% and 25 µl of a $\frac{1}{5,000}$ dilution of alkaline phosphatase conjugated F(ab')'$_2$ goat anti-mouse IgG (Fc specific, #115-056-071, Jackson Immunoresearch, Cedarlane, Burlington, ON) in blocking buffer was added. After a 1-h incubation, microplates were washed 4 times and 25 µl of p-nitrophenyl phosphate (pNPP) substrate (Sigma-Aldrich Canada Co., Oakville, ON) at 1 mg/ml in carbonate buffer at pH 9.6 was added and further incubated for one hour at 37° C. Absorbance was read at 405 nm using a SpectraMax 340 PC plate reader (Molecular Devices, Sunnyvale, CA).

ELISA positive antibodies were selected and further characterized by flow cytometry on U87MG cells overexpressing wild-type human EGFR (U87MG-EGFR WT) or human EGFRvIII (U87MG-EGFRvIII) to confirm their specificity. To this end, 15-ml supernatant from each positive clone was produced.

In order to compare our results with previous studies, additional monoclonal antibodies were used including the 13.1.2 antibody which is specific to EGFRvIII mutation (Hamblett K. J, et al., 2015; U.S. Pat. No. 7,736,644) and the 225 monoclonal antibody which is a murine antibody recognizing both wild-type human EGFR and human EGFRvIII proteins (Mendelson et al.; 2015).

Example 2: Cell Surface Binding by Flow Cytometry

For specificity analysis, several cell lines were used including human glioblastoma cell lines U87MG overexpressing wild-type human EGFR (a.k.a., U87MG-EGFR WT or U87 WT) and U87MG overexpressing human EGFRvIII (42-7 deletion mutation of EGFR a.k.a. U87MG-EGFRvIII or U87vIII).

The binding properties of the anti-EGFRvIII monoclonal antibodies selected in Example 1 were assessed by flow cytometry on human glioblastoma cell lines U87MG overexpressing wild-type EGFR and U87MG overexpressing EGFRvIII mutation.

Briefly, cells overexpressing full length wt EGFR or EGFRvIII were obtained from the laboratory of W. Cavanee (Ludwig Institute for Cancer Research, University of California at San Diego). Cells were grown in DMEM high glucose medium containing 10% FBS and 400 µg/ml G418. Prior to analysis, cells were plated such that they were not more than 80% confluent on the day of analysis. Unless otherwise stated, all media are kept are 4° C. and all incubations are performed on wet ice. Cells were washed in PBS and harvested by the addition of cell dissociation buffer (Sigma), centrifuged and resuspended in complete medium at a cell density of $2\times10^6$ cells/mL. Fifty µL/well of cells are distributed in a polypropylene v-bottom 96 well plate and equal volume of hybridoma supernatant were added and incubated for 2 hours. Cells were washed twice by centrifugation and further incubated with a FITC labeled F(ab')$_2$ goat anti-mouse antibody (Fc specific, #115-096-071, Jackson Immunoresearch, Cedarlane, Burlington, ON) for an hour. Cells were washed and resuspended in medium containing Propidium iodide to exclude dead cells from analysis. Samples were filtered through a 60 µm nylon mesh filter plate (Millipore, Ireland) to remove cell aggregates. Flow cytometry analyses were performed on 2,000 viable single-cells events gated on forward scattering, side scattering parameters and propidium iodide dye exclusion using a BD-LSR Fortessa flow cytometer (Becton-Dickinson Biosciences, CA, USA) and a standard filter set using BD FACSDiva™ acquisition software, according to manufacturer's instructions.

Cells were stained with either negative control anti-GFP 3E6 monoclonal antibody supernatant (open histograms) or tested hybridoma supernatant (grey histograms). Specific binding was reflected by the increase in the mean fluorescent intensity of antibody binding to U87 cells expressing EGFRvIII but not wild-type EGFR.

Out of the 36 positive cell based binding antibodies derived from 7 independent fusion experiments, we chose to further study three hybridoma supernatants, whose binding was found to be specific for EGFRvIII overexpressing U87MG cells, including F265-5B7 (FIG. 1A) referred to herein also as 5B7, F269-3D12 (FIG. 1B) referred to herein also as 3D12 and F271-1D2 (FIG. 1C) referred to herein also as 1D2. Data obtained for the 225 antibody (ATCC HB-8508) and the 13.1.2 antibody are shown in FIGS. 1D and 1E respectively.

Example 3: Evaluation of Binding on Purified Denatured Antigen

To evaluate if monoclonal antibodies bind to a conformational epitope, an ELISA analysis on native and denatured recombinant human wild-type EGFR and EGFRvIII proteins were performed. The 13.1.2 antibody) and the 225 antibody were used as controls. Antigens at 1-2 mg/ml were denatured by incubation at 95° C. for 5 min in PBS containing DTT at 40 mM final concentration. They were then incubated on ice for 5 min and diluted at their final coating concentration for ELISA purpose.

mAbs were purified using HiTrap ProteinG HP 1 mL columns GE Healthcare cat no. 17-0404-01 and desalted using Zeba-spin desalting columns 5 mL (Pierce) pre-equilibrated in PBS and filter sterilized through 0.22 UM membrane (Millipore). The final concentration of the antibody solutions was determined using a Nano-drop 2000 (ThermoScientific), using IgG as sample type. ELISA was performed as described above (serum titer determination) using 25 µl of mAb supernatant (Exp 1) or purified mAb at 1 µg/ml (Exp 2).

Table 1 shows ELISA results (n=2) of different mAb clones assessed on recombinant human EGFRvIII or wild-type EGFR, in native or denatured conditions. As expected, the 225 antibody binds to both wild-type EGFR and EGFRvIII under native conditions only. The 13.1.2 antibody binds to EGFRvIII in native and denatured conformations, but not to EGFR wild-type native or denatured. All other mAbs binds to EGFRvIII in native and denatured conformations.

TABLE 1

Binding on native or denatured recombinant proteins by ELISA

| | EGFRvIII | | | | EGFRwt | | | |
| | Native | | Denatured | | Native | | Denatured | |
| Clone | Exp 1 | Exp 2 | Exp 1 | Exp 2 | Exp 1 | Exp 2 | Exp 1 | Exp 2 |
|---|---|---|---|---|---|---|---|---|
| 5B7 | 1.144 | 0.874 | 1.674 | 0.623 | 0.008 | 0.002 | 0.046 | 0.000 |
| 3D12 | 1.173 | 1.125 | 1.859 | 0.517 | 0.095 | 0.011 | 0.045 | 0.001 |
| 1D2 | 1.491 | 0.935 | 2.553 | 1.054 | 0.002 | 0.004 | ND | 0.000 |
| 225 | 1.081 | 1.496 | 0.001 | 0.004 | 1.204 | 1.320 | −0.010 | 0.002 |
| 13.1.2 mIgG1 | 1.097 | 1.671 | 1.914 | 1.705 | 0.011 | 0.003 | 0.003 | 0.005 |
| 13.1.2 mIgG2a | 1.291 | 1.487 | 2.094 | 1.495 | 0.009 | 0.003 | 0.007 | 0.002 |
| Neg ctrl mouse mAb | ND | −0.001 | ND | 0.002 | ND | 0.002 | ND | 0.000 |

ND: not determined

Selected hybridoma were recloned by limiting dilution to ensure their monoclonality.

Example 4. Epitope Mapping by Yeast Surface Display

The yeast surface display method (Feldhaus M J et al., 2003 Nat Biotechnol. 2003 February; 21(2): 163-70) was used to map the epitopes of our collection of monoclonal antibodies against EGFRvIII. This technique allows cloned protein or peptide of choice to be expressed and displayed at cell surface through covalent linkage to cell wall. The displayed protein/peptide can be interrogated for antibody binding.

A total of 36 different human EGFRvIII fragments of variable size from 10 to 414 as indicated in FIG. 3 were cloned into the pPNL6 vector (obtained from The Pacific Northwest National Laboratory, USA) as fusion proteins to be expressed and displayed as Aga2-HA-hEGFRvIII-MYC. The displayed human EGFRvIII fragments were used to identify the smallest fragment required for the binding of each anti-EGFRvIII monoclonal antibodies.

Assessment of the binding of anti-EGFRvIII monoclonal antibodies to the fusion proteins expressed on yeast cell surface was done by flow cytometry analysis. Yeast cells were labeled with both the anti-EGFRvIII monoclonal antibody and chicken anti-Myc antibody the latter being used to monitor the level of expression of the fusion protein. Following a wash step, binding of the primary antibodies is probed by a two-color indirect fluorescence labeling using a specific mouse and chicken secondary antibodies for each of the primary antibody respectively.

The anti-EGFRvIII monoclonal antibodies were binding with similar signal intensities to both full length hEGFRvIII protein and small peptides of the same protein, as well to both native and heat denatured yeast displayed antigen fragments, suggesting that the epitopes for the mAbs are contained within a continuous peptide fragment (linear).

The results presented in FIG. 3 illustrate the binding properties of the anti-EGFRvIII monoclonal antibodies to various fragments of the EGFRvIII and wild-type EGFR protein cells displayed on yeast cells.

Based on the results presented in FIG. 3, the smallest EGFRvIII fragment (peptide) that the anti-EGFRvIII antibodies were able to bind was identified (Table 2). Two different epitope bins were identified: 1) aa 1-18 recognized by 1D2 as well as the 13.1.2 control mAb, 2) aa 15-37 recognized by 5B7 and 3D12. Surprisingly, despite the fact that all antibodies were capable of binding specifically to EGFRvIII expressing cells, the 5B7 and 3D12 monoclonal antibodies bind to an epitope that doesn't encompass the spliced junction neoepitope (aa 5-7) found exclusively in EGFRvIII. Despite the absence of binding on U87MG-EGFR WT expressing cells. 5B7 did bind slightly to yeast cells engineered to express EGFR WT fragments 266-482 (FIG. 3).

TABLE 2

Summary of epitope binning

| mAb Clone Name | Epitope Containing EGFRvIII Fragment |
|---|---|
| 5B7 | aa 15-37 |
| 3D12 | aa 15-37 |
| 1D2 | aa 1-18 |
| hFc-13.1.2 | aa 1-18 |
| 225 | aa 43-456 |

Example 5. Fine Epitope Mapping Using Yeast Surface Display

To further characterize mAb epitopes within the EGFRvIII 15-37 region, an alanine scan of this region was performed, and modified fragments were expressed at the surface of the yeast. SEQ ID NO:5 shows the amino acid sequence of the EGFRvIII 15-37 fragment, where each underlined amino acid was mutated to alanine. The resulting DNAs were expressed at the surface of the yeast and each anti-EGFRvIII mAbs was tested on the corresponding yeast mutant strain by flow cytometry analysis. The original Ala19 and Ala22 were not mutated. Thus, this assay determined the contribution of each amino acid(s) in mAb binding in comparison to the original wild-type fragment (SEQ ID NO:5) which is attributed the value of 100%.

Table 3 shows the results obtained in flow cytometry analysis for the 5B7 and 3D12 monoclonal antibodies. Results obtained are in line with the results of FIG. 3 i.e. binding of mAbs in bin 15-37 are strongly inhibited by mutation of at least one amino acid residue between position 15 and 19. This assay shows that the binding of the 5B7 monoclonal antibody is compromised by mutation of Val17, Arg18, Cys20, Gly21, Asp23 and Cys35. The binding of the 3D12 monoclonal antibody is strongly inhibited by mutation of Arg18, Cys20, Gly21, Tyr25, Glu26, Gly31 and Cys35, and weakened by Glu29 and Arg33 mutation to Alanine.

TABLE 3

Flow cytometry evaluation of mAb binding to yeast expressing mutated amino acid within fragment 15-37 of EGFRvIII. Data represent the % of binding of mAb on the yeast displaying the mutated sequence compared to the binding on the yeast displaying the wild-type sequence, normalized to the Myc-tag expression.

| Amino acid mutated to | mAbs | | Corresponding |
|---|---|---|---|
| Ala | 5B7-2 | 3D12-2 | peptide sequence |
| Ser15 | 91.6 | 90.2 | SEQ ID: 48 |
| Cys16 | 240.2 | 170.7 | SEQ ID: 49 |
| Val17 | 0.3 | 116.2 | SEQ ID: 50 |
| Arg18 | 0.2 | 0.1 | SEQ ID: 51 |
| Ala19* | ND | ND | — |
| Cys20 | 0.4 | 0.2 | SEQ ID: 52 |
| Gly21 | 0.1 | 0.0 | SEQ ID: 53 |
| Ala22* | ND | ND | — |
| Asp23 | 0.8 | 62.4 | SEQ ID: 54 |
| Ser24 | 230.1 | 232.8 | SEQ ID: 55 |
| Tyr25 | 192.5 | 3.5 | SEQ ID: 56 |
| Glu26 | 140.1 | 1.4 | SEQ ID: 57 |
| Met27 | 111.4 | 75.3 | SEQ ID: 58 |
| Glu28 | 78.5 | 71.0 | SEQ ID: 59 |
| Glu29 | 109.7 | 47.7 | SEQ ID: 60 |
| Asp30 | 105.6 | 78.5 | SEQ ID: 61 |
| Gly31 | 98.9 | 10.7 | SEQ ID: 62 |
| Val32 | 101.1 | 93.8 | SEQ ID: 63 |
| Arg 33 | 95.8 | 22.1 | SEQ ID: 64 |
| Lys34 | 192.7 | 137.0 | SEQ ID: 65 |
| Cys35 | 1.5 | 0.1 | SEQ ID: 66 |
| Lys36 | 87.2 | 95.1 | SEQ ID: 67 |
| Lys37 | 143.3 | 162.3 | SEQ ID: 68 |

*Original Ala 19 and Ala 22 were not mutated
Legend
Values between 0% and 15%: No binding
Values between 16% and 59%: Partial binding
Values at or above 60%: Complete binding Example 6: Antibody Sequencing The sequence of the VH and VL regions of the anti-EGFRvIII antibodies 5B7, 3D12 and 1D2 were analyzed.

Briefly, total RNA was extracted from hybridoma clones (Qiagen, RNEasy) and reverse transcribed into cDNA (SuperScript™, ThermoFisher Scientific, Waltham, MA, USA). DNA encoding VH and VL domains was PCR amplified (Platinum Taq or equivalent) using mixtures of degenerate forward primers annealing in FR1 and a single reverse primer annealing in CH1 (Novagen/EMD Millipore cat. no 69831-3). The resulting amplicons were sequenced using the Sanger method on an ABI 3730xl instrument or were determined using 2×250 bp reads on an 10 Illumina MiSeq instrument.

Sequences of the VH and VL regions as well as the CDR regions are shown in the Sequence Table section. Analysis of the sequence for a consensus binding sequence of the CDR 1-3 regions of the VH and VL chains was conducted using Kabat numbering scheme (Kabat et al 1992, Johnson et al 2004). The results of this analysis indicated that 5B7, 3D12 and 1D2 monoclonal antibodies have unique VH and VL CDRs.

Example 7: EGFRvIII CAR-T Design and Cloning

To generate a chimeric antigen receptor sequence using the EGFRvIII-specific antibody sequences (as described above), amino acid sequences based on the variable regions of the 5B7, 3D12, 1D2 monoclonal antibodies were assembled into single chain variable fragments (scFv) containing their respective heavy chain, a $(GGGGS)_3$ (SEQ ID NO: 89) linker sequence (although any appropriate linker could be used), followed by the light chain in silico. An amino acid sequence compatible with a restriction site was included at the beginning of the linker sequence to allow later recombination as needed. In addition, a spacer sequence was attached to the 3' end of the sequence. In the present case, a hinge domain derived from mouse CD8 was used, but this sequence can also be substituted for other spacer domains as described herein.

FIG. 4 illustrates the synthetic assembly of 5B7 amino acids (SEQ ID NO: 30) for insertion in CAR vector to generate EGFRvIII 5B7 CAR (SEQ ID NO:32). Sequence shows the heavy chain portion (underlined), amino acids corresponding to a restriction site (*), linker (double underlined), the light chain portion (underlined), and the mouse CD8 hinge. The 3D12 and 1D2 sequences were assembled similarly (SEQ ID NO:33 and SEQ ID NO:35 respectively) to generate EGFRvIII 3D12 CAR (SEQ ID NO:34) and EGFRvIII 1D2 CAR (SEQ ID NO:36) respectively.

After in silico assembly, sequences were reverse translated into DNA using a standard human codon usage table via online tool available to the public (Chojnacki, S. et al., Nucl Acid Res. 45 (W1): W550-553, 2017). Specific DNA sequences for various restriction sites were avoided and appropriate DNA linkers were added to the ends of the DNA to allow insertion of the sequence into a modular CAR vector using a scarless cloning strategy based on a Type IIS restriction enzyme (Bbsl). DNA was then synthesized by Integrated DNA Technologies in the form of a linear double stranded gene fragment.

The DNA sequence of the 5B7 scFv and hinge as synthesized is presented in SEQ ID NO: 31. Sequence shows heavy chain (underlined), restriction sites (nucleotide 5 to 10, 412 to 418 and 1039 to 1045), linker (419 to 457), light chain (underlined), and mouse CD8 hinge (twice underlined). Sticky end sequences for scarless insertion via type IIs cloning are shown in bold.

This sequence was then inserted into our modular CAR vector (SEQ ID NO:37, FIG. 5A). The modular CAR vector comprises nucleic acid sequence encoding a human CD28 signal peptide (nucleotide 1 to 50), restriction sites (nucleotides 57 to 63 and 65 to 70) including sticky end sequences shown in black, filler (irrelevant sequence), a human CD28 transmembrane domain (nucleotide 84 to 165), a human CD28 intracellular transduction domain (nucleotide 167 to 294), and a human CD3 zeta intracellular transduction domain (nucleotide 295 to 642). Linker sequences for scarless insertion via type IIs cloning are shown in bold.

Certain truncations of the CAR sequences especially truncations in the scFv portion (as exemplified in SEQ ID NO:78) can retain similar activity while removing some backbone elements of the antibody heavy or light chain. Exemplary data is provided to show that a CAR plasmid containing truncated versions of both the VH and VL elements of 1D2-CAR has minimal effect on the ability of CAR-transduced T cells to respond to target cells as measured using electroporated Jurkat cells exposed to varying doses of EGFRvIII+ target cells (FIG. 5B and FIG. 5C).

Sequences were combined into a modular plasmid vector which also contained a human EF1a promoter, P2A-GFP marker and Lentiviral transfer elements. Construction was confirmed using clonal sequencing in *Escherichia coli* bacteria, and plasmids were isolated by standard technique.

Figures 5B, 5C, 5D:
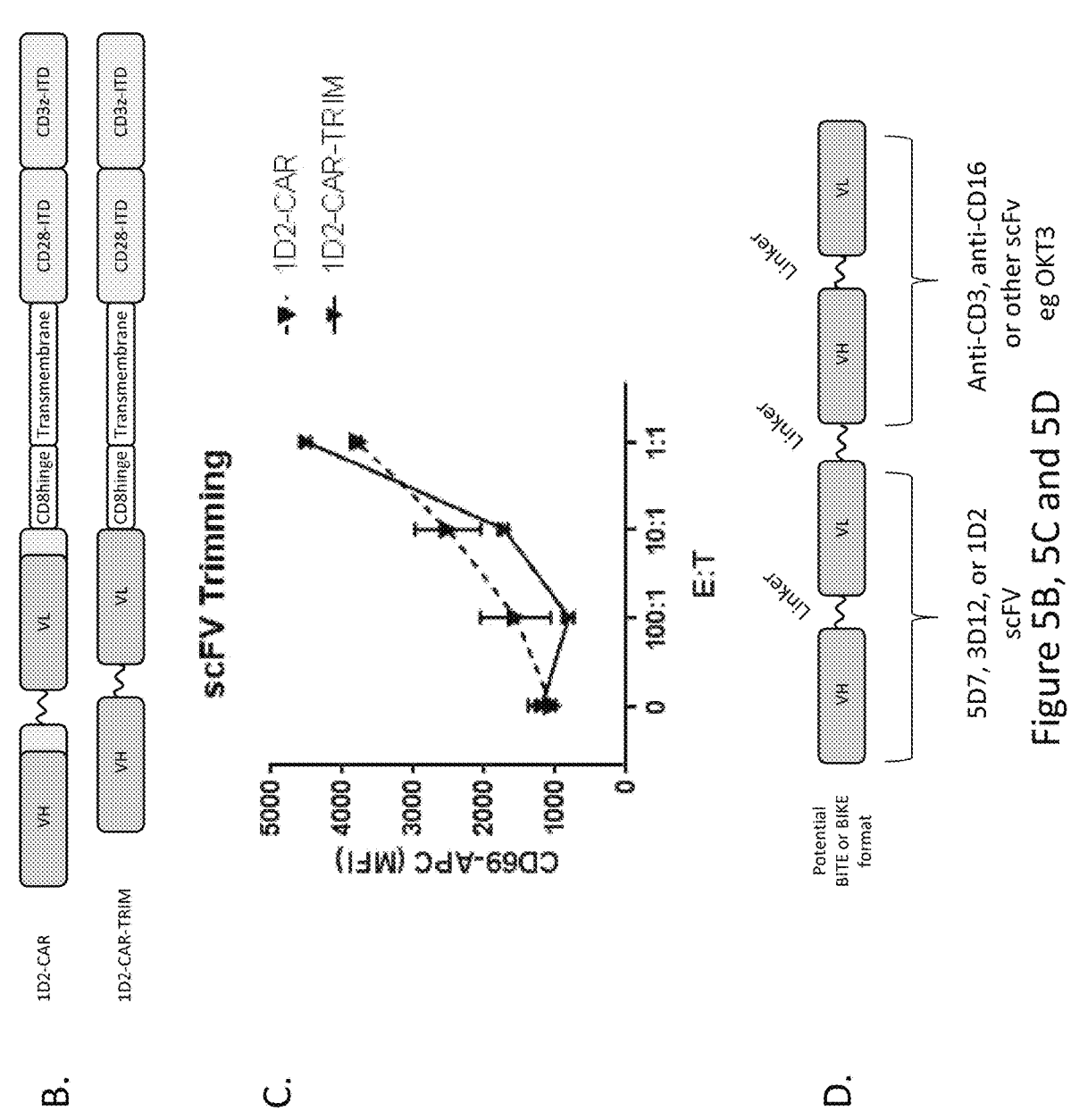
FIG. 5B: Schematic illustrating 1D2-CAR-TRIM which contains a shorter scFv portion (SEQ ID NO:78)
FIG. 5C: Graph comparing 1D2-CAR and 1D2-CAR-TRIM construct using the CAR-J assay. Briefly, Jurkat cells were electroporated with plasmids expressing either full length or trimmed form of the CAR as illustrated in 5B. CAR-J cells were then mixed with EGFRvIII expressing target cells and examined for activation signature (CD69 expression) via antibody staining and flow cytometric analysis.
FIG. 5D: Schematic illustrating potential bi-specific T-cell engagers and bispecific killer cell engagers.

Alternatively, the scFv sequences described herein can be inserted into vectors for expression of bi-specific T-cell engagers, bispecific killer cell engagers or trispecific killer cell engagers (FIG. 5D).

Example 8: Detection of CAR Expression on Transduced Cells

Two strategies were employed to detect the expression of CAR molecule(s) on transduced immune cells. As a research strategy, the green fluorescence protein (GFP) was co-expressed with the EGFRvIII CAR and used as a surrogate for monitoring CAR expression in transduced cells.

Briefly, the Jurkat human CD8+ T-cell line was transiently transfected with the EGFRvIII construct which also expressed GFP using a 2A self-cleaving peptide based multi-gene expressing system. Expression of EGFP was quantified using flow cytometry (FIG. 6A) and the surface expression of CAR was detected by flow cytometry using a fluorescent tagged antibody that recognize murine IgG (Goat Anti-Mouse IgG H&L [Alexa Fluor® 594]; Jackson Immunoresearch) (FIG. 6B).

Figure 6A:
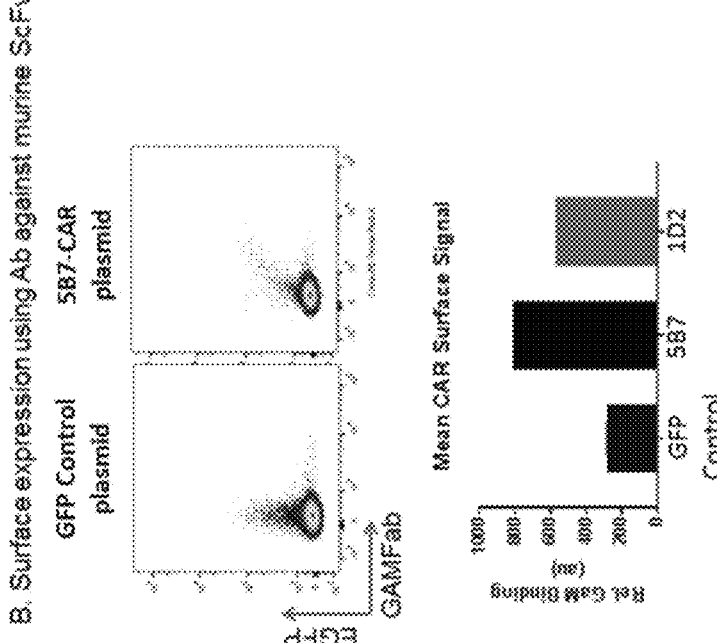
FIGS. 6A and 6B: Human CD8 T cell line Jurkat transiently transfected with the EGFRvIII CAR construct which also expressed green fluorescent protein (GFP) using a 2A self-cleaving peptide based multi-gene expressing system. Expression of GFP was quantified using flow cytometry (A) and the surface expression of CAR was detected by flow cytometry using a fluorescent tagged antibody that recognize murine IgG (Goat Anti-Mouse IgG H&L [Alexa Fluor® 594]; Abcam) (B) (5B7=F265-5B7; 3D12=F269-3D12; 1D2=F271-1D2).
Figure 6B:
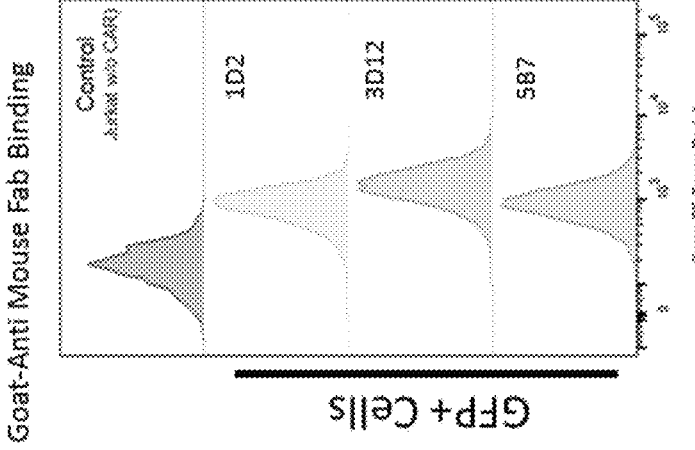

The flow cytometry analysis showed an increased level of GFP expression in EGFRvIII CAR (EGFRvIII 5B7 CAR (a.k.a. 5B7), EGFRvIII 3D12 CAR (a.k.a. 3D12) and EGFRvIII 1D2 CAR (a.k.a. 1D2)) transduced cells compared to the control cells (FIG. 6A).

In addition, an antibody recognizing murine IgG sequences within the scFv (GAMFab) was used for direct evaluation of surface expression of the CAR. The EGFRvIII CAR (PSLQC2-5B7 and 1D2) transduced cells were positive for GFP expression and binding of the GAMFab antibody whereas the control cells that were transduced with GFP expressing control plasmid devoid of a CAR construct (PX458) showed GFP expression but no binding of the GAMFab antibody (FIG. 6B).

Example 9: CAR-T Functionality Screening

The in vitro functionality of the EGFRvIII CAR constructs was tested using a novel flow cytometry based high-throughput screening platform developed by the Applicant; which is in some instances referred to as CAR-J assay. In brief, EGFRvIII or control (CD19-targeted) CAR plasmids were electroporated into the Jurkat human CD8+ T-cell line. Cells expressing CAR were then exposed to various target cell lines (with or without EGFRvIII expression) in varying doses and maintained under standard culture conditions. Following 24 hours of co-incubation with target cells, CAR-T cells were examined for cellular activation by flow cytometry via surface expression of the T-cell activation marker CD69. The level of auto-activation (tonic signaling) associated with each CAR was also examined by quantification of the level of CD69 expression on non-stimulated CAR-expressing Jurkat cells or CAR-expressing Jurkat cells incubated with irrelevant target cells. The high-throughput screening method for CAR functionality is summarized in FIG. 7A.

Figures 7A, 7B, 7C, 7D:
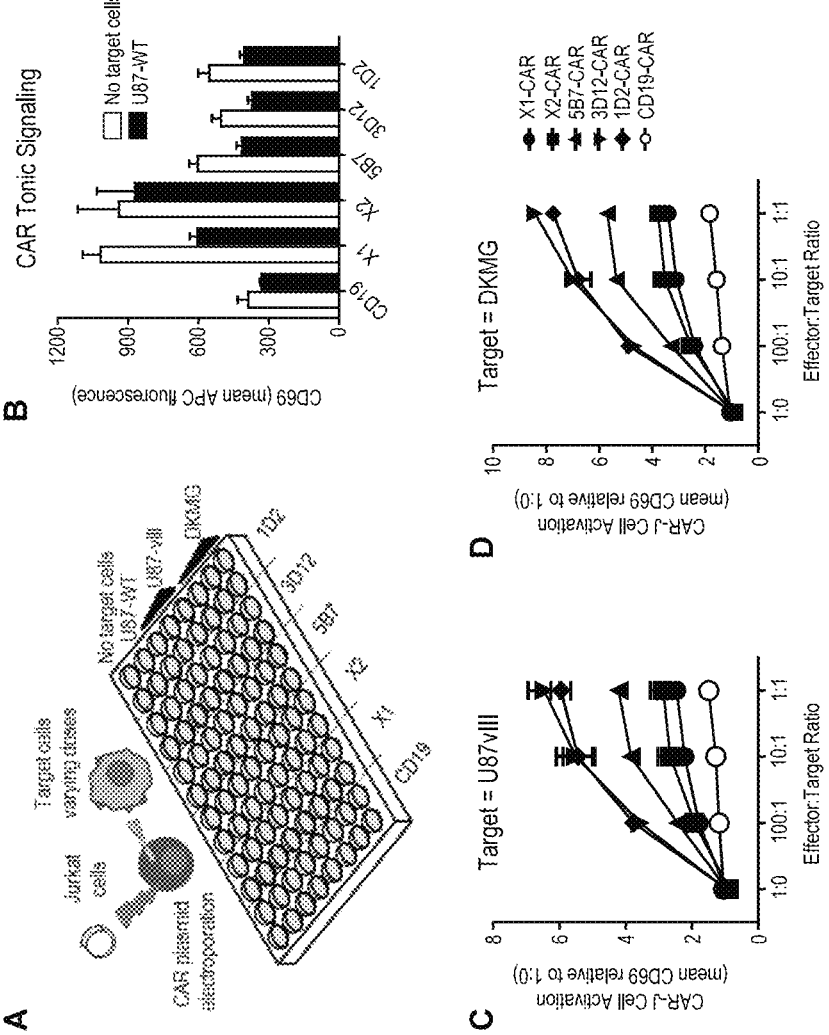
FIG. 7: Schematic illustrating the high-throughput screening method for CAR functionality. (A) Jurkat cells electroporated with various CAR constructs were exposed to varying doses of target cells with (U87-vIII, DKMG) or without (U87-MG) specific target expression. CAR constructs found to have inappropriate properties for advancement are also shown (X1, X2) (B) Tonic signaling/auto-activation of each CAR construct was assessed by examining the level of CD69 expression in CAR-expressing (GFP+) cells without additional stimulation. (C and D) The relative increase in expression of CD69 within CAR cells following stimulation with EGFRvIII expressing target cells is shown.

Jurkat cells electroporated with various CAR constructs (X1, X2, 5B7, 3D12 and 1D2) were exposed to varying doses of target cells with (U87vIII, DKMG) or without (U87-MG) specific target expression (FIGS. 7B, C and D). Tonic signaling/auto-activation of each CAR construct was assessed by examining the level of CD69 expression in CAR-expressing (GFP+) cells without additional stimulation (FIG. 7B). The relative increase in expression of CD69 within CAR cells following stimulation with EGFRvIII-expressing target cells is illustrated in FIG. 7C and FIG. 7D.

The results of FIGS. 7B-D indicate that some CAR constructs (X1 and X2) showed high level of activation in the absence of stimulation or when stimulated with target cells that do not express EGFRvIII (U87-MG), indicative of high tonic signaling and therefore would not be suitable for CAR-mediated therapy. The 5B7, 3D12 and 1D2 CAR constructs showed very low level of activation in the absence of stimulation or in response to irrelevant target cells (U87-MG, FIG. 7B) but showed high level of activation in response to specific stimulation with EGFRvIII expressing target cells U87vIII and DKMG (FIGS. 7C and D, respectively). This allowed the selection of the 5B7, 3D12 and 1D2 CAR constructs for further characterization.

Figure 8A:
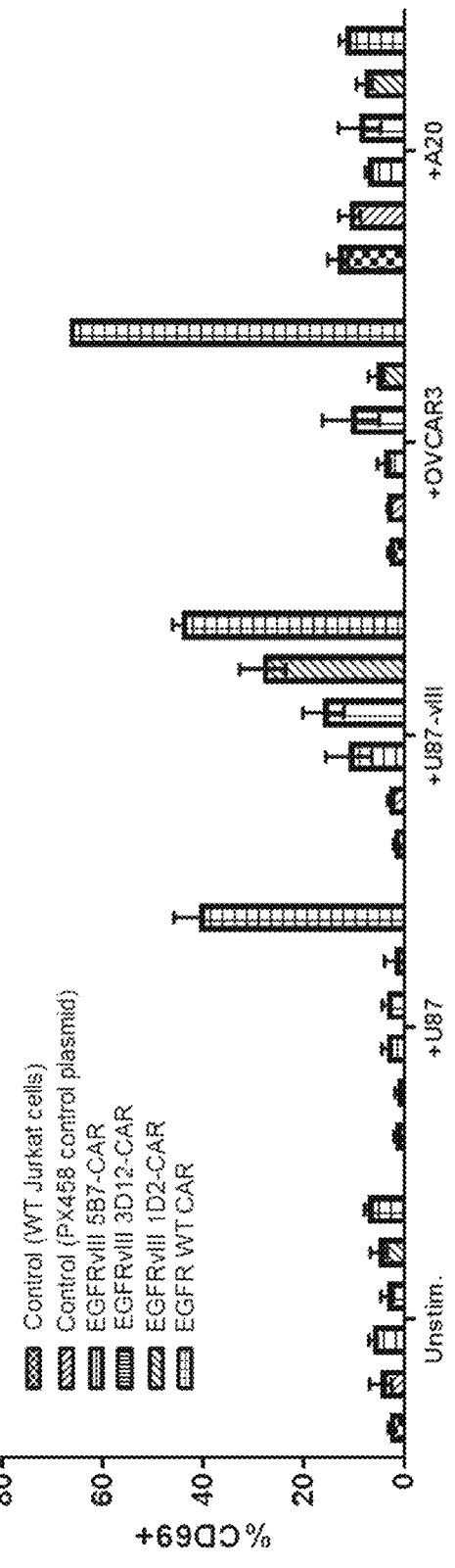
FIG. 8A: Graph illustrating the in vitro functionality of EGFRvIII CAR-T constructs. Jurkat cells electroporated with various CAR constructs (EGFRvIII 5B7 CAR, EGFRvIII 3D12 CAR, EGFRvIII 1D2 CAR, EGFR WT CAR) were exposed to target cells with (U87vIII) or without (U87, OVCAR3 and A20) EGFRvIII target expression for 24 hours. The level of cell activation was measured by quantifying surface expression of CD69 on Jurkat cells (CD45 positive) by flow cytometry.

In a separate experiment, plasmid expressing CAR targeting EGFRvIII or control plasmids (PX458 expressing GFP but no CAR construct and plasmid expressing CAR targeting wild-type EGFR protein) were electroporated into Jurkat cells. GFP expressing cells and control Jurkat cells (CD45 positive) were then exposed to various target cell lines with (U87vIII) or without (A20 and U87-MG) EGFRvIII expression in varying doses and maintained under standard culture conditions. Following 24 hours of incubation, cells were examined via flow cytometry for GFP expression and cell activation using fluorescent staining against the T-cell activation marker CD69. The level of auto-activation (tonic signaling) associated with each CAR was also examined by quantification of the level of CD69 expression on non-stimulated CAR-expressing Jurkat cells (FIG. 8A).

The baseline level of CD69 expression in unstimulated CAR transduced Jurkat cells is similar to levels seen with unstimulated wild-type Jurkat cells suggesting no detectable tonic signaling in CAR-T cells. Similarly, low level of CD69 expression that were comparable to levels seen with wild-type Jurkat cells was seen with EGFR wild-type and EGFRvIII CAR-T cells when stimulated with human B cell lymphoma cell line A20 that does not express wild-type EGFR or EGFRvIII protein. CAR-T cells targeting wild-type EGFR responded strongly to U87, U87vIII and OVCAR3 cells, which express the wild-type EGFR protein whereas EGFRvIII targeted CAR-T cells responded only to U87vIII cells and not the U87 or OVCAR3 cells (FIG. 8A).

In order to optimize the length of the hinge element that should be integrated in CAR constructs, various constructs were tested using Jurkat activation assay similarly as described above. Briefly, CAR constructs containing either 5B7 scFV (SEQ ID NO:44) or 3D12 scFV (SEQ ID NO: 45) sequence followed by (1) a very long hinge wherein a 17AA poly-glycine linker [(GGGGS) 3GG] (SEQ ID NO: 92) was followed by the 45AA sequence of the hinge domain of the human CD8 protein [L17-CD8h: SEQ ID NO:83], (2) human CD8 hinge alone [45CD8h: SEQ ID NO: 84], (3) a truncated form of CD8-hinge containing C-terminal 35AA [35CD8h: SEQ ID NO:85], (4) a truncated form of CD8-hinge containing C-terminal 15AA [15CD8h: SEQ ID NO:86], or (5) a truncated form of CD8-hinge containing C-terminal 1AA (1CD8h: PLD) were generated. Jurkat cells were then electroporated with vIII-specific constructs with varying hinge length and co-cultured at a 1:1 effector to target ratio with antigen expressing cells (U87III) or antigen-negative cells (U87WT). Results clearly demonstrate that EGFRvIII constructs developed here show high target-specific response across a range of hinge lengths (FIG. 8B).

Based on the in vitro functionality data, EGFRvIII CAR constructs 1D2 and 3D12 were selected for testing for in vivo functionality.

Figures 9A, 9B, 9C:
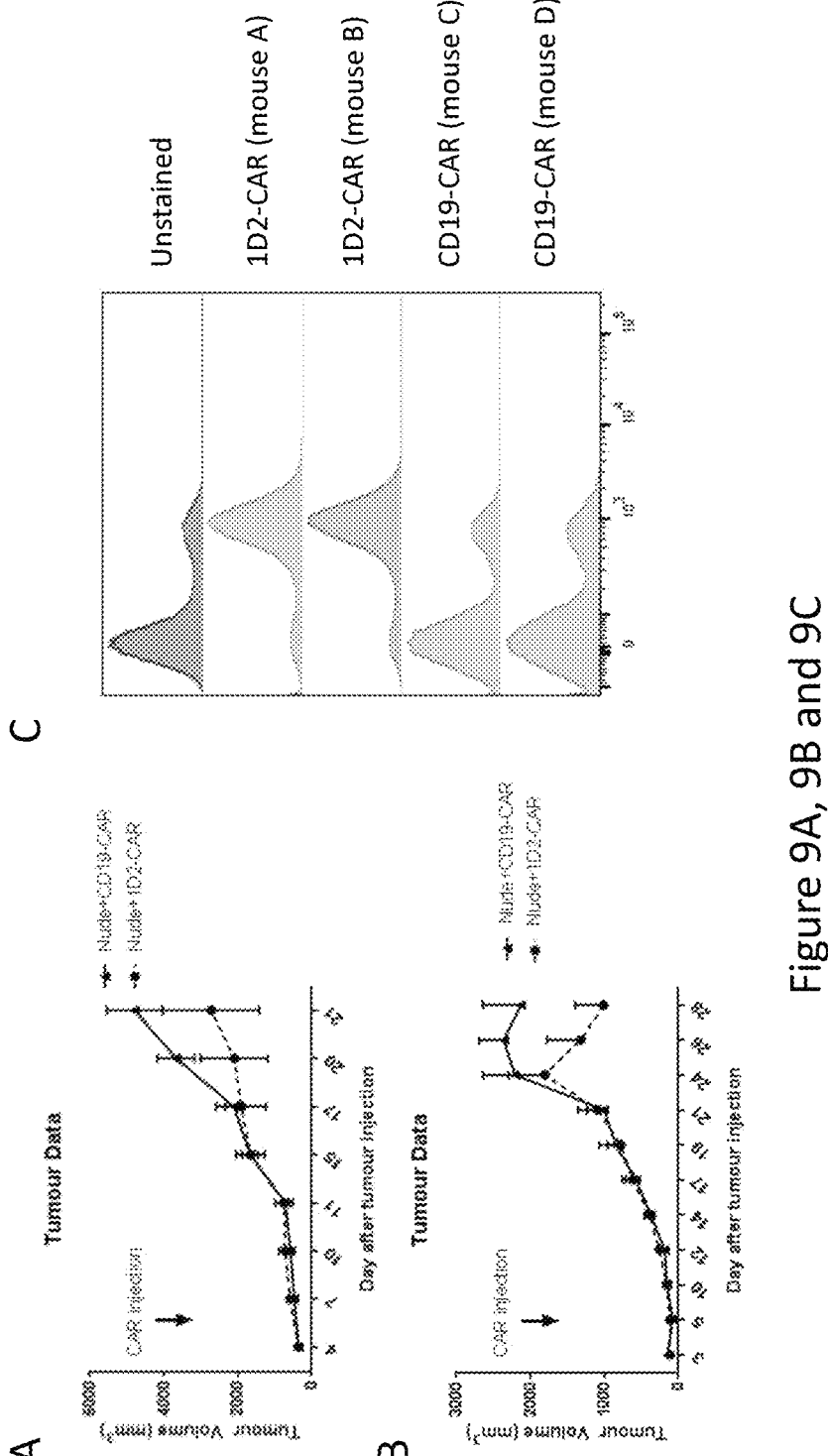
FIG. 9: Graphs showing the tumor volume (mean±SEM) in athymic nude mice (Jackson Laboratory, Barr Harbor, ME) injected subcutaneously with $1\times10^6$ (FIG. 9A) or $4\times10^6$ (FIG. 9B) U87vIII human glioblastoma cells expressing EGFRvIII and administered with $10^5$ (FIG. 9A) or $10^6$ (FIG. 9B) human primary T cells expressing EGFRvIII 1D2 CAR or negative control CD19 CAR on day 5 post tumor cell injection. Tumor size (the length and the width) was measured using a digital vernier caliper. Tumor volume was calculated by using the formula: Tumor volume=(0.4) (ab2), where a=large diameter and b=smaller diameter. The level of CD8 T cell infiltration in tumors from two animals each from groups receiving EGFRvIII targeted CAR-T and showing good tumor control was assessed and compared to CD19 CAR-T negative control (FIG. 9C).

Briefly, athymic nude mice (Jackson Laboratory, Barr Harbor, ME) were injected subcutaneously with $1 \times 10^6$ (FIG. 9A) or $4 \times 10^6$ (FIG. 9B) U87vIII human glioblastoma cells expressing EGFRvIII. CD19 targeted CAR-T was used as control in the studies. On day 5 post tumor cell injection, mice were given $10^5$ (FIG. 9A) or $10^6$ (FIG. 9B) human primary T cells expressing EGFRvIII 1D2 CAR. Animals were monitored for tumor growth. Tumor size (the length and the width) was measured using a digital vernier caliper. Tumor volume was calculated by using the formula: Tumor volume=(0.4) (ab2), where a=large diameter and b=smaller diameter. The tumor volume (mean±SEM) is depicted in FIG. 9A and FIG. 9B. FIG. 9C depicts the level of CD8$^+$ T-cell infiltration in tumors from two animals each from groups receiving EGFRvIII targeted CAR-T and showing good tumor control and irrelevant CAR (CD19 CAR-T).

The results illustrate an increase in tumor growth in all animals receiving irrelevant CD19 CAR-T cells whereas effective tumor control was seen in a subset of animals receiving EGFRvIII CAR-T cells (FIG. 9A and FIG. 9B). EGFRvIII CAR-T treated mice showing good tumor control also showed good CAR-T cell infiltration in the tumor (FIG. 9C).

Example 10: CAR-NK Functional Screening

Figures 10B, 10C:
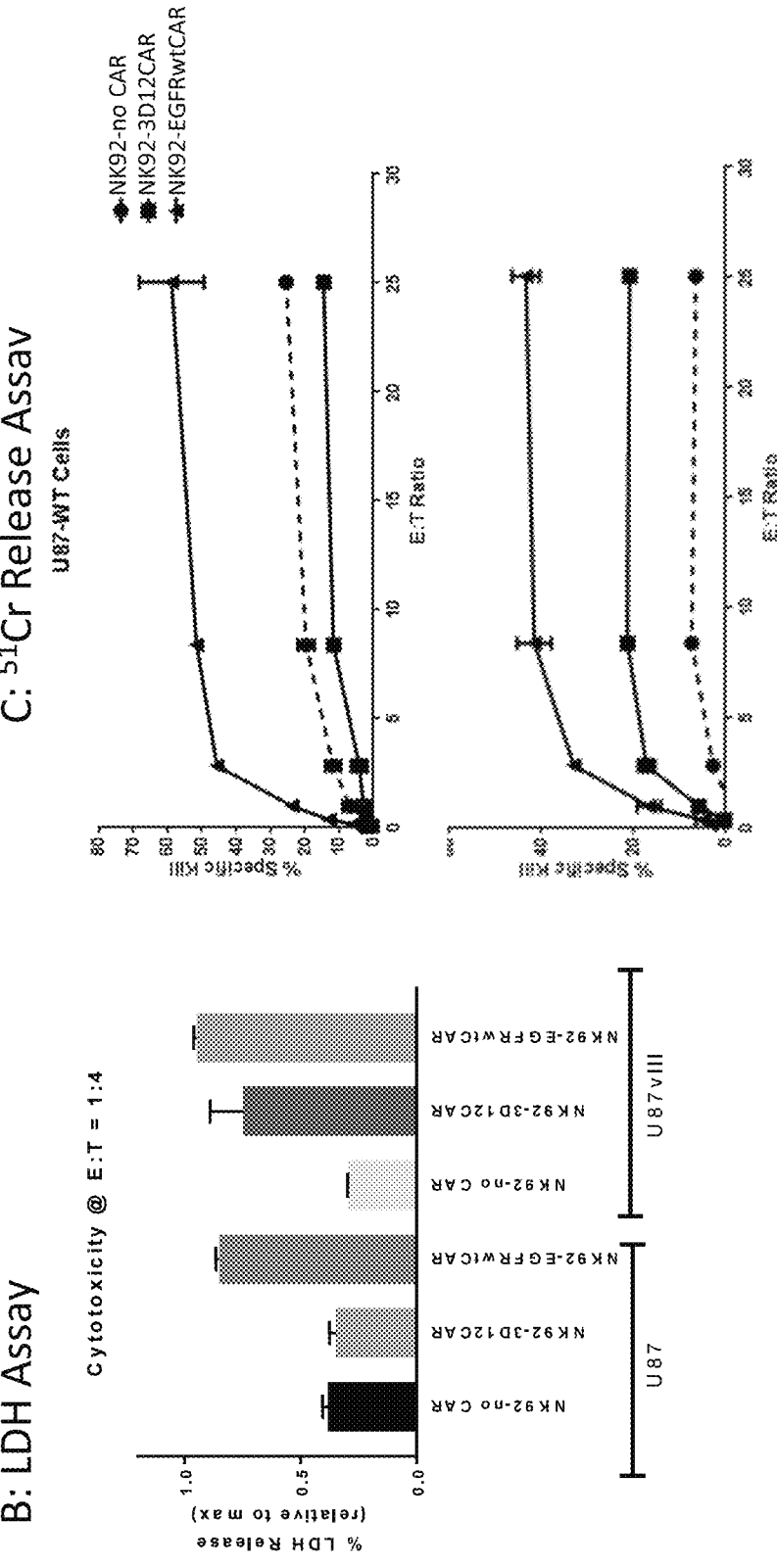
FIG. 10: Schematic illustrating the generation of EGFRvIII targeted NK92-CAR cells for in vitro testing of tumor cytotoxicity (FIG. 10A). Graphs showing data of cytotoxicity of control NK92 cells (NK92-no CAR), NK 92 cells expressing EGFRvIII 3D12 CAR construct (NK92-3D12CAR) or EGFR WT CAR construct towards cells expressing EGFRvIII (U87-vIII) or WT EGFR (U87) as measured by LDH (FIG. 10B) or $^{51}$Cr-release assay (FIG. 10C). Wild-type NK92 cells devoid of a CAR construct was used as negative control (NK92 wt).

The human NK-92 cell line (Gong et al; 1994; Leukemia) was used for development and testing of EGFRvIII targeted NK 3D12-CAR cells. The graphic in FIG. 10A represents the generation of EGFRvIII targeted NK92-CAR cells for in vitro testing of tumor cytotoxicity. In brief, EGFRvIII or control (wild-type EGFR protein-targeted) CAR plasmids were electroporated into NK-92 cells (ATCC; Manassas, VA). Cells expressing CAR were then exposed to various target cell lines with (U87vIII) or without (U87) EGFRvIII expression in varying doses and maintained under standard culture conditions. Following 24 hours of co-incubation with target cells, tumor cell killing was assessed by quantifying the release of lactate dehydrogenase (FIG. 10B LDH; a cytosolic enzyme which is release upon cell death) by colorimetry or by using the standard $^{51}$Cr-release assay (FIG. 10C). Wild-type NK92 cells devoid of CAR construct was used as negative control.

EGFR WT NK-CAR showed killing of U87 and U87vIII cells both of which overexpress a common epitope present on both EGFR protein isoforms whereas EGFRvIII CAR-NK showed preferential killing of U87vIII cells. The specific cytotoxicity of EGFRvIII targeted NK 3D12-CAR towards EGFRvIII and not the wild-type EGFR protein expressing cells was shown by both LDH (FIG. 10B) and $^{51}$Chromium release (FIG. 10C) assays.

The in vivo functionality of the EGFRvIII targeted NK-CARs was also tested using 2 independent experiments using athymic nude mice bearing EGFRvIII expressing U87vIII tumors.

Figures 11A, 11B:
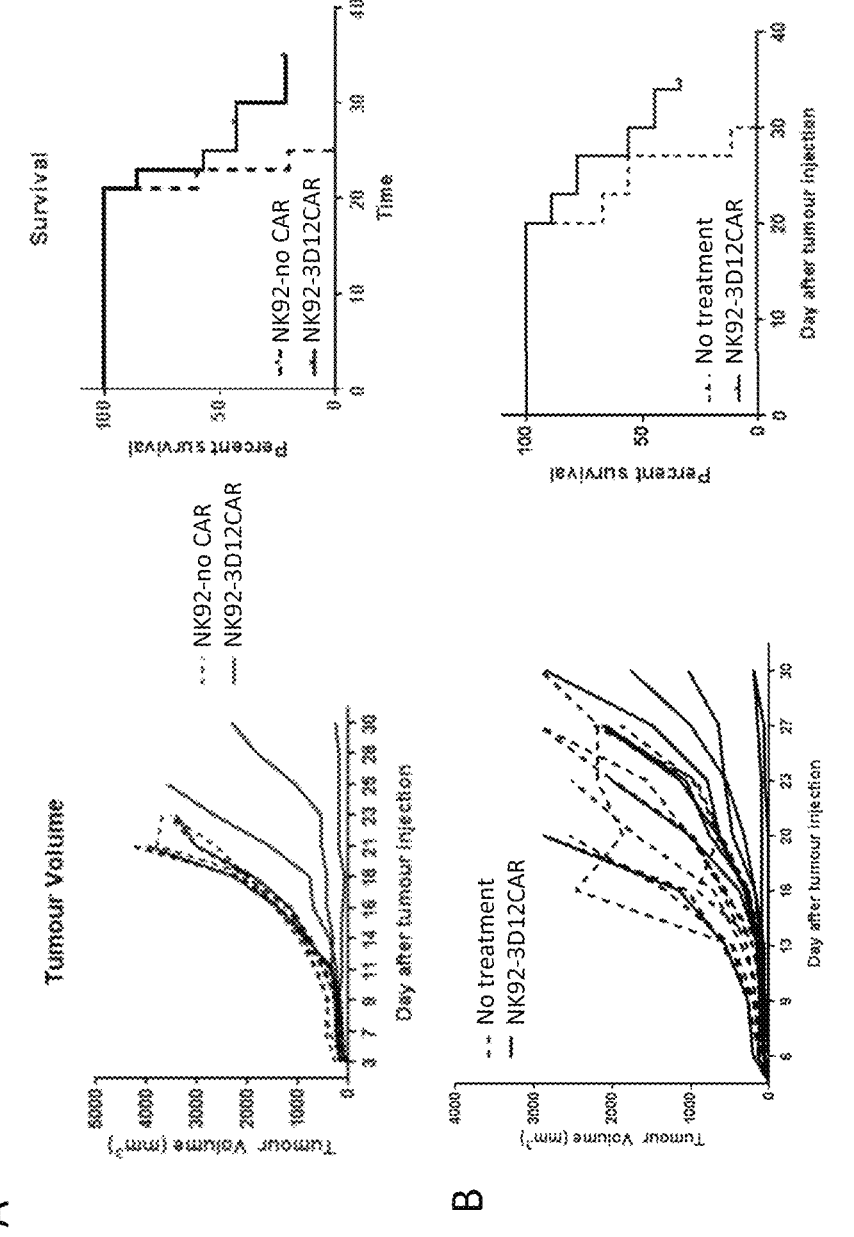
FIG. 11: Graphs illustrating tumor growth (left panels) and survival (right panels) of tumor-bearing athymic nude mice administered with NK92 cells expressing EGFRvIII 3D12 CAR construct or devoid of CAR expression (NK92-WT or NK92 wt). Athymic nude mice (Jackson Laboratory, Barr Harbor, ME) were injected subcutaneously with $1\times10^6$ U87vIII human glioblastoma cells expressing EGFRvIII. On day 2 post tumor cell injection, mice were given either $5\times10^6$ wild-type NK92 cells devoid of CAR or NK92 cells expressing EGFRvIII 3D12 CAR (FIG. 11A) or on day 3 post tumor induction animals were given $1\times10^7$ EGFRvIII 3D12 NK-CAR or left untreated (FIG. 11B). Animals were monitored for survival and tumor growth. Tumor size (the length and the width) was measured using a digital vernier caliper. Tumor volume was calculated by using the formula: Tumor volume=(0.4) (ab2), where a=large diameter and b=smaller diameter.

Briefly, athymic nude mice (Jackson Laboratory, Barr Harbor, ME) were injected subcutaneously with $1 \times 10^6$ U87vIII human glioblastoma cells expressing EGFRvIII. On day 2 post tumor cell injection, mice were given either $5 \times 10^6$ wild-type NK92 cells devoid of CAR or NK92 cells expressing EGFRvIII 3D12-CAR-NK (FIG. 11A) or on day 3 post tumor induction animals were given $1 \times 10^7$ EGFRvIII 3D12-CAR-NK or left untreated (FIG. 11B). Animals were monitored for survival (left panels) and tumor growth (right panels). Tumor size (the length and the width) was measured using a digital vernier caliper. Tumor volume was calculated by using the formula: Tumor volume=(0.4) (ab2), where a=large diameter and b=smaller diameter.

In both studies, better control of tumor growth and increased survival was seen in animals receiving EGFRvIII NK-CAR compared to animals receiving unmodified NK92 cells or untreated controls (FIG. 11A and FIG. 11B) respectively.

The chimeric antigen receptors (CAR) generated herein may therefore be used to re-direct NK cells to specifically recognize and kill cells expressing EGFRvIII protein.

Example 11: Primary CAR-T Functional Testing In Vitro

Human primary peripheral blood derived T cells were used for confirmation of in vitro and in vivo activity of EGFRvIII targeted 3D12 CARs constructs in the context of primary human immune cells. In brief, EGFRvIII-CAR or control (human CD19-targeted FMC63-CAR) lentivirus was generated using standard production protocols in HEK293 and concentrated using ultracentrifugation. Primary T cells were isolated from donor blood samples using magnetic separation and activated using anti-CD3/CD28 beads. Primary T cells were then transduced with CAR lentivirus and expanded for several days in culture.

Figure 12:
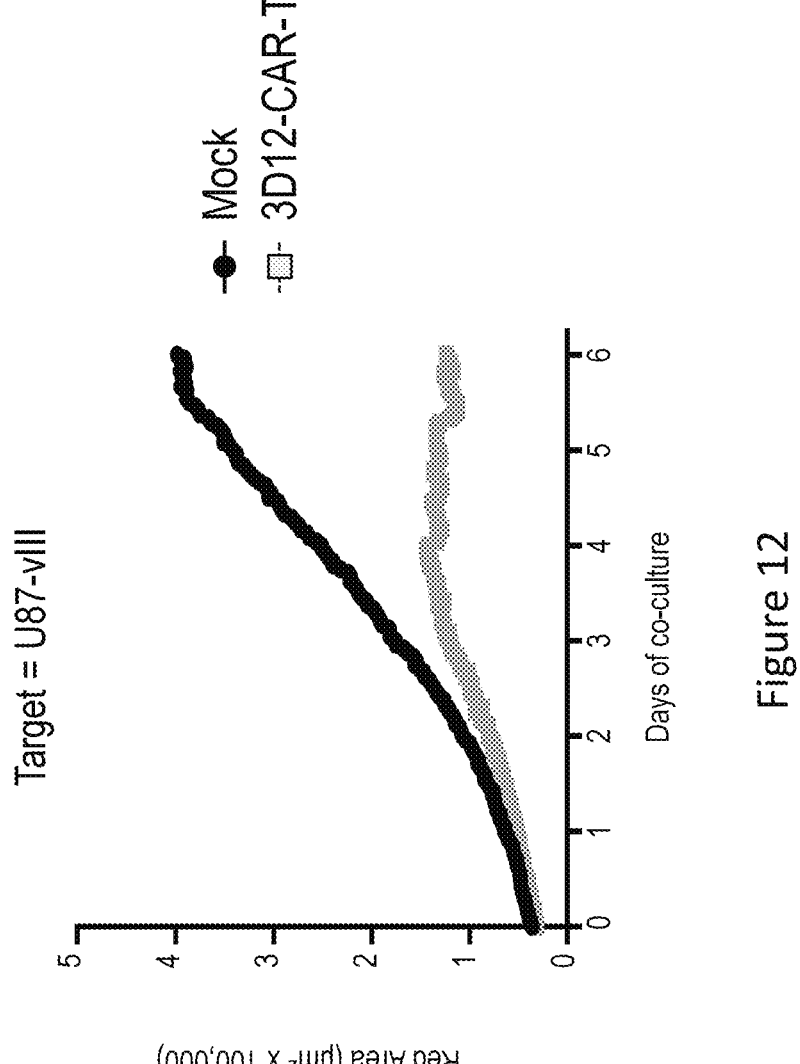
FIG. 12: Graph illustrating repression of target cell growth in CAR transduced T-cell/target cell co-cultures. Human primary peripheral blood derived T cells were transduced with EGFRvIII-specific CAR lentivirus (3D12-CAR-T) or treated similarly in the absence of lentivirus (Mock) and grown for several days in culture. CAR-transduced or non-transduced T cells were then placed in co-culture with EGFRvIII antigen expressing target cells which express nuclear localized mKate2-fluorescent protein (U87vIII). Cells were then examined using live fluorescence microscopy (Incucyte™, Sartorius). Graph depicts the relative target cell growth over 6 days as measured via automated counting of mKate2+ cells.

In vitro functionality of primary human EGFRvIII-specific CAR-transduced T cells were assessed using a live-fluorescence microscopy approach. Briefly, EGFRvIII targeted CAR-T or mock transduced T cells, wherein no lentiviral construct was introduced into cells handled under similar conditions, were generated as described above. Cells were then placed in co-culture with EGFRvIII-expressing target cells modified to also express a nuclear-localized form of mKate2 fluorescent protein. Co-cultures were monitored constantly over 6 days using the Incucyte™ automated live fluorescent microscopy device (Sartorius, USA). The relative growth of target cells was then assessed using automated counting of mKate2+ cells (FIG. 12). Data showed that the growth of U87MG overexpressing EGFRvIII cells was efficiently repressed by 3D12 CAR-T compared to mock transfected T-cells.

Example 12: Primary CAR-T Functional Testing In Vivo

Figure 13A:
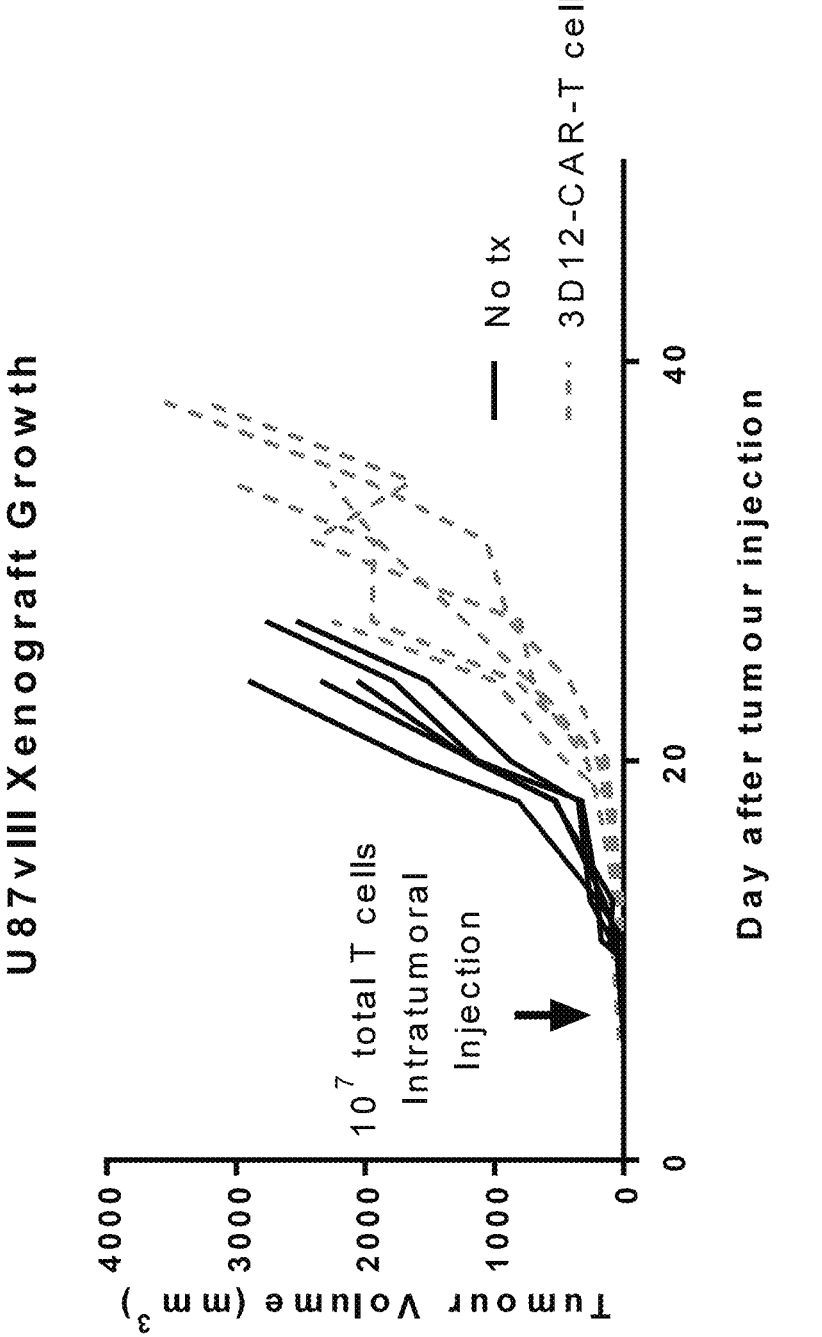
FIG. 13: Graphs illustrating tumor growth (left panels) and survival (right panels) of tumor-bearing NOD/SCID/IL-2Ry-null (NSG) mice. NSG mice (Jackson Laboratory, Barr Harbor, ME) were injected subcutaneously with $1\times10^6$ U87vIII human glioblastoma cells expressing EGFRvIII. On day 7 post tumor cell injection, mice were given either primary human T cells transduced with EGFRvIII-3D12 CAR or left untreated. Tumour growth was then monitored by caliper measurements (FIG. 13A). Tumor size (the length and the width) was measured using a digital vernier caliper. Tumor volume was calculated by using the formula: Tumor volume=(0.4) (ab2), where a=large diameter and b=smaller diameter. Survival is defined as time to humane endpoint (defined as a tumour volume exceeding 2000 mm$^3$) with and without CAR-T treatment (FIG. 13B).
Figure 13B:
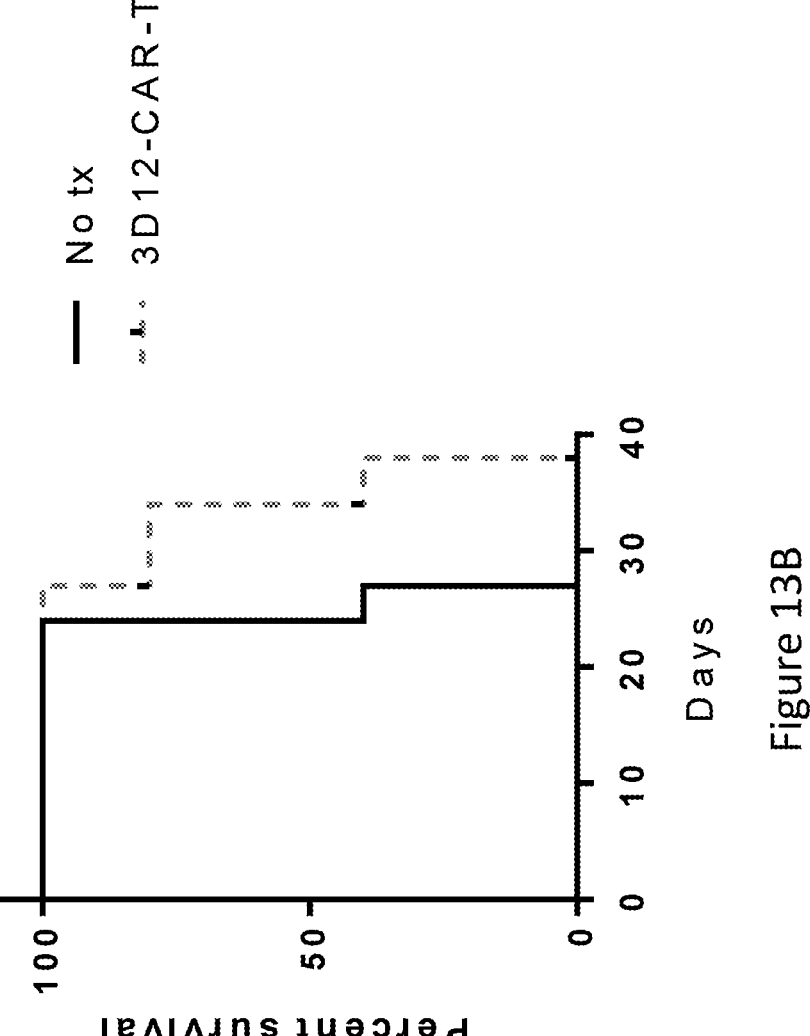

The in vivo functionality of the EGFRvIII targeted primary CAR-T cells was also tested using Nod-SCID-IL2γR2$^{-/-}$ (NSG) mice (Jackson Laboratory, Barr Harbor, ME) bearing EGFRvIII expressing U87vIII tumors. Briefly, mice were subcutaneously injected with $1 \times 10^6$ fluorescently labelled U87-vIII cells. Eight days after tumour cell injection, cryo-preserved CAR-T cells were thawed, washed with PBS, and $1 \times 10^7$ total T cells (with 20-25% CAR transduction) were immediately delivered intra-tumourally, ensuring equal distribution of tumour sizes between groups. Tumour growth was evaluated three times per week using calipers by trained animal technicians blinded to specific treatment groups (FIG. 13A). Primary endpoint was tumour size above 2000 mm$^3$, with secondary endpoints determined by overall animal health and well-being (FIG. 13B). Tumor volume was calculated by using the formula: Tumor volume=(0.4) (ab2), where a=large diameter and b=smaller diameter.

In this study, better control of tumor growth and increased survival was seen in animals receiving EGFRvIII primary CAR-T compared to untreated control animals (FIG. 13A and FIG. 13B) respectively.

Example 13: Bi-Specific Immune Cell Engager Functional Testing

Figure 14:
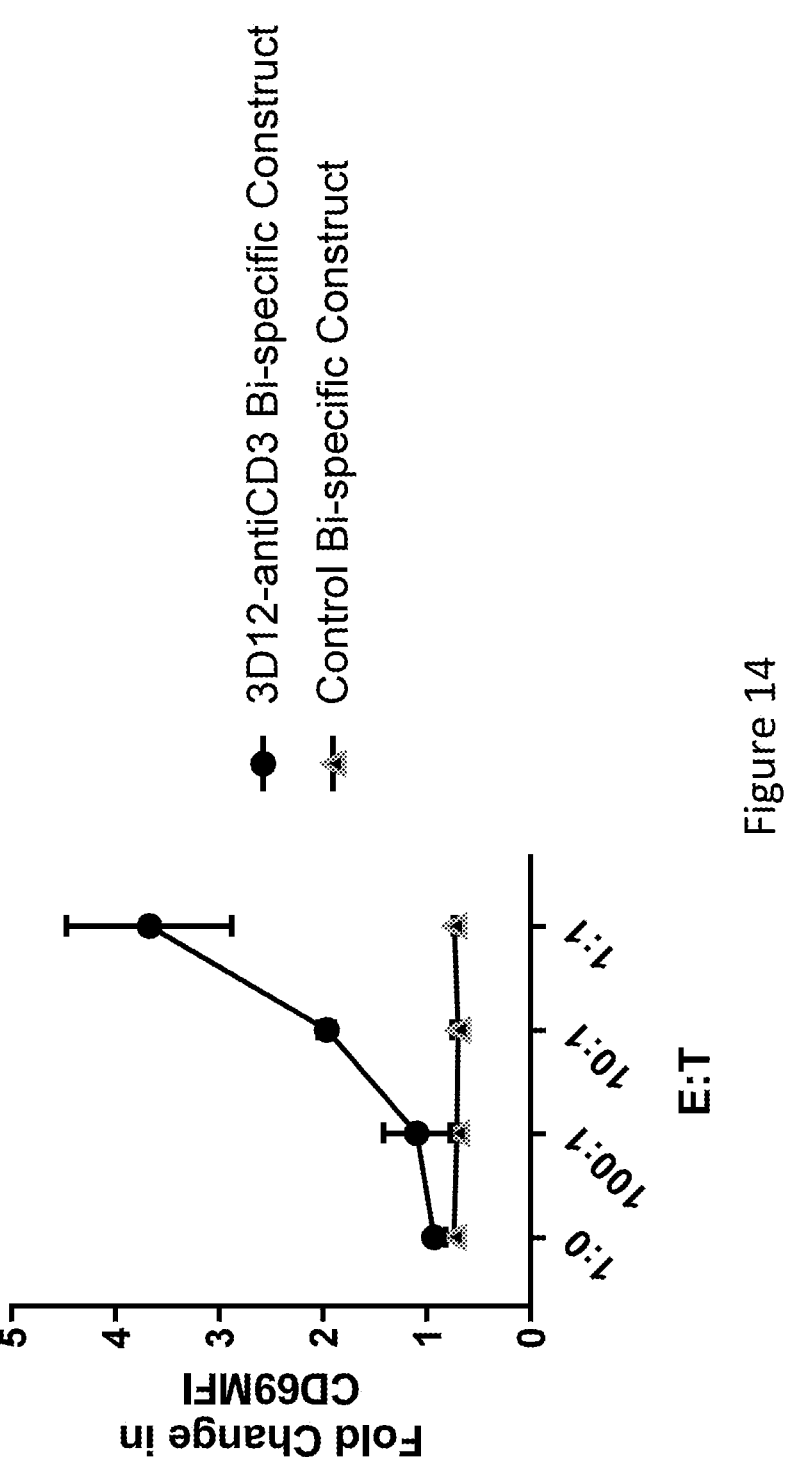
FIG. 14: Graph illustrating screening of bi-specific T cell engager activity with EGFRvIII-specific constructs containing 3D12-scFV sequence linked to OKT3 human CD3-specific scFV. Supernatant from human embryonic kidney (HEK293) cells transiently expressing 3D12-OKT3 bi-specific engager construct were transferred to wells containing Jurkat cells and varying doses of antigen expressing target cells (U87vIII). Target-induced activation of T cells in the presence or absence of bispecific T-cell engager was measured by examining the level of CD69 expression using human CD69-specific antibody staining and flow cytometry. The fold change in CD69 expression with and without bispecific-T cell engager over varying doses of target cell is shown here.

Various experiments were performed to demonstrate the activity of the novel EGFRvIII-specific single chain variable fragment in the context of a bispecific T cell engager. Constructs were generated using synthetic DNA wherein the 3D12 scFV sequence (SEQ ID NO:45) was linked to a previously demonstrated CD3-engaging scFv sequence (SEQ ID NO:82). A plasmid expressing this bi-specific construct was transfected into human embryonic kidney cells (HEK293T) and supernatant was collected after 2 to 4 days in culture. Supernatant from HEK293T were transferred to wells containing Jurkat cells and varying doses of antigen expressing target cells (U87vIII). Target-induced activation in the presence or absence of bispecific T-cell engager was measured by examining the level of CD69 expression using human CD69-specific antibody staining and flow cytometry (FIG. 14). Results showed that only EGFRvIII targeted bi-specific construct could induce high target-specific T-cell activation response compared to a control bi-specific molecule.

Figure 15:
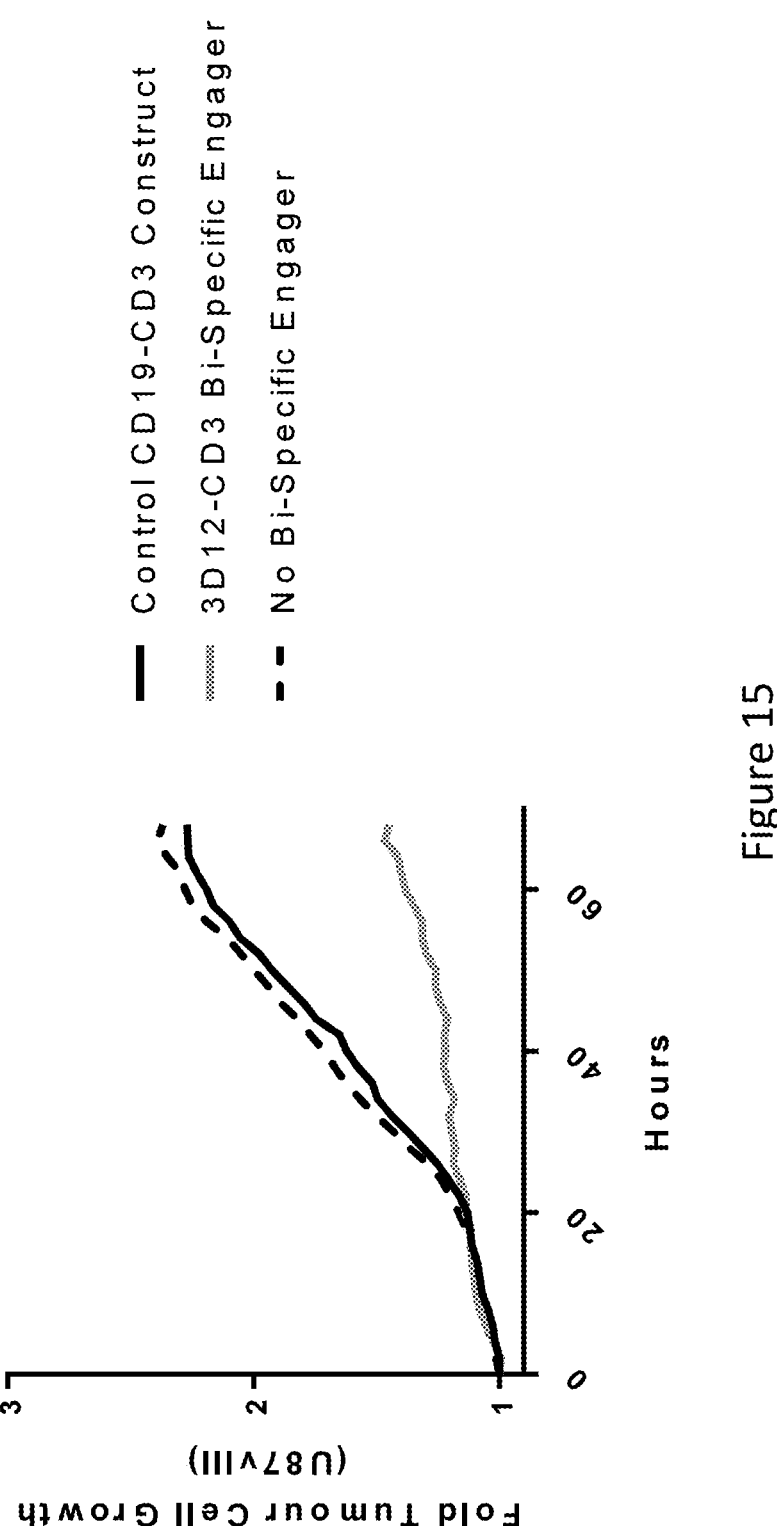
FIG. 15: Graph illustrating repression of target cell growth in T-cell/target cell co-cultures in the presence of a bi-specific T cell engager constructs containing 4E11-scFV sequence linked to OKT3 human CD3-specific scFV. A control bi-specific T cell engager composed of human—CD19-specific scFv linked to OKT3 is shown for comparison. Supernatants from human embryonic kidney cells transiently expressing 4E11-OKT3 bi-specific T cell engager construct or the CD19-OKT3 bi-specific T cell engager construct were transferred to wells containing primary blood derived T cells and EGFRvIII antigen expressing target cells which express nuclear localized mKate2-fluorescent protein (U87vIII). Cells were then examined using live fluorescence microscopy (Incucyte™, Sartorius, USA). Graph depicts the relative target cell growth over 72 hours as measured via automated counting of mKate2+ cells.

In vitro functionality of primary human EGFRvIII-specific bi-specific immune T-cell engager in interaction with primary human T cells were assessed using a live-fluorescence microscopy approach. Briefly, polyclonally expanded human T cells which were allowed to return to a rest state over several weeks in culture were placed in co-culture with EGFRvIII-expressing target cells modified to also express a nuclear-localized form of mKate2 fluorescent protein. Various doses of HEK293T supernatant, or supernatant wherein cells were secreting a control CD19-CD3 targeted or 3D12-CD3 targeted bi-specific immune cell engager were transferred to T-cell target cell co-cultures. Co-cultures were then monitored constantly over 6 days using the Incucyte™ automated live fluorescent microscopy device (Sartorius, USA). The relative growth of target cells was then assessed using automated counting of mKate2+ cells (FIG. 15). Results demonstrate that 3D12-CD3 bi-specific immune cell engagers can actively induce T-cell mediated repression of EGFRvIII-positive tumour cell growth compared to the bi-specific CD19-CD3 control molecule or mock supernatant.

The embodiments and examples described herein are illustrative and are not meant to limit the scope of the disclosure as claimed. Variations of the foregoing embodiments, including alternatives, modifications and equivalents, are intended by the inventors to be encompassed by the claims. Citations listed in the present application are incorporated herein by reference.

REFERENCES

All patents, patent applications and publications referred to throughout the application are incorporated herein by reference.

Andris-Widhopf, J., et al. Generation of human scFv antibody libraries: PCR amplification and assembly of light- and heavy-chain coding sequences. Cold Spring Harbor protocols, 2011(9).

Bird et al. Science 242:423-426(1988)

Chojnacki, S. et al., Nucl Acid Res. 45 (W1): W550-553 (2017)

Chothia C, Lesk A M. Canonical structures for the hypervariable regions of immunoglobulins. J Mol Biol. August 20: 196(4): 901-17(1987).

Feldhaus M J et al., 2003 Nat Biotechnol. February; 21(2): 163-70(2003).

Gacerez, A. T. et al., J Cell Physiol. 231(12): 2590-2598 (2016),

Gan H. K., Anna N. Cvrljevic, Terrance G. Johns. The epidermal growth factor receptor variant III (EGFRvIII): where wild things are altered. FEBS Journal 280; 5350-5370(2013).

Gong et al; Leukemia, 8(4): 652-658(1994)

Hamblett K. J, et al., Molecular Cancer Therapeutics, Vol. 14(7), pp. 1614-24(2015).

Huston et al. Proc. Natl. Acad. Sci. USA 85:5879-5883 (1988).

Jones, P. T. et al., Nature 321:522-525(1986).

Johnson G, Wu T T. The Kabat database and a bioinformatics example. Methods Mol Biol., 248:11-25(2004).

Kabat E A, Wu T T. Identical V region amino acid sequences and segments of sequences in antibodies of different specificities. Relative contributions of VH and VL genes, minigenes, and complementarity-determining regions to binding of antibody-combining sites. J Immunol., 147:1709-19(1991). Lefranc, M.-P., The Immunologist, 7, 132-136(1999).

Mendelsohn J, Prewett M, Rockwell P, Goldstein N I. CCR 20th anniversary commentary: a chimeric antibody, C225, inhibits EGFR activation and tumor growth. Clin Cancer Res. 21(2): 227-9(2015).

Queen C, Schneider W P, Selick H E, Payne P W, Landolfi N F, Duncan J F, Avdalovic N M, Levitt M, Junghans R P, Waldmann T A, Proc Natl Acad Sci USA 86, 10029-10033(1989).

Riechmann, L. et al., Nature 332:323-327(1988).

Sadelain, M. et al. Cancer Discovery, 3(4): 388-98, (2013).

Sblattero & Bradbury, 2000, Nature Biotechnology, 18(1): 75-80, (2000).

Schaefer, J. V, et al. Construction of scFv Fragments from Hybridoma or Spleen Cells by PCR Assembly. (R. Kontermann & S. Dübel, Eds.), (2010).

Tatusova, et al. FEMS Microbiol Lett. 174:247-250 (1999).

Tempest P R, Bremmer P, Lambert M, Taylor G, Furze J M, Carr F J, Harris W J Biotechnology 9, 266-271 (1991). 5

Tsurushita N, Hinton, RP, Kumar S Design of humanized antibodies: From anti-Tac to Zenapax. Methods 36, 69-83 (2005).

U.S. Pat. No. 7,736,644.

Wang, X et al., Molecular Therapy-Oncolytics, 3:16015, 2016

Ward et al., Nature 341:544-546 (1989).

Zhang, C. et al., Biomarker Research, 5:22 (2017).

SEQUENCE TABLE
CDRs are generally indicated in bold and/or underlined

| Seq. ID | Description | Sequence |
|---|---|---|

1 — Wild type human EGFR ectodomain cDNA sequence

CTGGAGGAAAAGAAAGTTTGCCAAGGCACGAGTAACAAGCTCACGCAGTT
GGGCACTTTTGAAGATCATTTTCTCAGCCTCCAGAGGATGTTCAATAACT
GTGAGGTGGTCCTTGGGAATTTGGAAATTACCTATGTGCAGAGGAATTAT
GATCTTTCCTTCTTAAAGACCATCCAGGAGGTGGCTGGTTATGTCCTCAT
TGCCCTCAACACAGTGGAGCGAATTCCTTTGGAAAACCTGCAGATCATCA
GAGGAAATATGTACTACGAAAATTCCTATGCCTTAGCAGTCTTATCTAAC
TATGATGCAAATAAAACCGGACTGAAGGAGCTGCCCATGAGAAATTTACA
GGAAATCCTGCATGGCGCCGTGCGGTTCAGCAACAACCCTGCCCTGTGCA
ACGTGGAGAGCATCCAGTGGCGGGACATAGTCAGCAGTGACTTTCTCAGC
AACATGTCGATGGACTTCCAGAACCACCTGGGCAGCTGCCAAAAGTGTGA
TCCAAGCTGTCCCAATGGGAGCTGCTGGGGTGCAGGAGAGGAGAACTGCC
AGAAACTGACCAAAATCATCTGTGCCCAGCAGTGCTCCGGGCGCTGCCGT
GGCAAGTCCCCCAGTGACTGCTGCCACAACCAGTGTGCTGCAGGCTGCAC
AGGCCCCCGGGAGCGACTGCCTGGTCTGCCGCAAATTCCGAGACGAAG
CCACGTGCAAGGACACCTGCCCCCCACTCATGCTCTACAACCCCACCACG
TACCAGATGGATGTGAACCCCGAGGGCAAATACAGCTTTGGTGCCACCTG
CGTGAAGAAGTGTCCCCGTAATTATGTGGTGACAGATCACGGCTCGTGCG
TCCGAGCCTGTGGGGCCGACAGCTATGAGATGGAGGAAGACGGCGTCCGC
AAGTGTAAGAAGTGCGAAGGGCCTTGCCGCAAAGTGTGTAACGGAATAGG
TATTGGTGAATTTAAAGACTCACTCTCCATAAATGCTACGAATATTAAAC
ACTTCAAAAACTGCACCTCCATCAGTGGCGATCTCCACATCCTGCCGGTG
GCATTTAGGGGTGACTCCTTCACACATACTCCTCCTCTGGATCCACAGGA
ACTGGATATTCTGAAAACCGTAAAGGAAATCACAGGGTTTTTGCTGATTC
AGGCCTTGGCCTGAAAACAGGACGGACCTCCATGCCTTTGAGAACCTAGAA
ATCATACGCGGCAGGACCAAGCAACATGGTCAGTTTTCTCTTGCAGTCGT
CAGCCTGAACATAACATCCTTGGGATTACGCTCCCTCAAGGAGATAAGTG
ATGGAGATGTGATAATTTCAGGAAACAAAAAATTTGTGCTATGCAAATACA
ATAAACTGGAAAAAACTGTTTGGGACCTCCGGTCAGAAAACCAAAATTAT
AAGCAACAGAGGTGAAAACAGCTGCAAGGCCACAGGCCAGGTCTGCCATG
CCTTGTGCTCCCCCGAGGGCTGCTGGGGCCCGGAGCCCAGGGACTGCGTC
TCTTGCCGGAATGTCAGCCGAGGCAGGGAATGCGTGGACAAGTGCAACCT
TCTGGAGGGTGAGCCAAGGGAGTTTGTGGAGAACTCTGAGTGCATACAGT
GCCACCCAGAGTGCCTGCCTCAGGCCATGAACATCACCTGCACAGGACGG
GGACCAGACAACTGTATCCAGTGTGCCCACTACATTGACGGCCCCCACTG
CGTCAAGACCTGCCCGGCAGGAGTCATGGGAGAAAACAACACCCTGGTCT
GGAAGTACGCAGACGCCGGCCATGTGTGCCACCTGTGCCATCCAAACTGC
ACCTACGATGCACTGGGCCAGGTCTTGAAGGCTGTCCAACGAATGGGCC
TAAGATCCCGTCC

2 — Human EGFR ectodomain amino acid sequence

LEEKKVCQGTSNKLTQLGTFEDHELSLQRMENNCEVVLGNLEITYVQRNY
DLSFLKTIQEVAGYVLIALNTVERIPLENLQIIRGNMYYENSYALAVLSN
YDANKTGLKELPMRNLQEILHGAVRESNNPALCNVESIQWRDIVSSDELS
NMSMDFQNHLGSCQKCDPSCPNGSCWGAGEENCQKLTKIICAQQCSGRCR
GKSPSDCCHNQCAAGCTGPRESDCLVCRKERDEATCKDTCPPLMLYNPTT
YQMDVNPEGKYSFGATCVKKCPRNYVVTDHGSCVRACGADSYEMEEDGVR
KCKKCEGPCRKVCNGIGIGEFKDSLSINATNIKHFKNCTSISGDLHILPV
AFRGDSFTHTPPLDPQELDILKTVKEITGELLIQAWPENRTDLHAFENLE
IIRGRTKQHGQFSLAVVSLNITSLGLRSLKEISDGDVIISGNKNLCYANT
INWKKLFGTSGQKTKIISNRGENSCKATGQVCHALCSPEGCWGPEPRDCV
SCRNVSRGRECVDKCNLLEGEPREFVENSECIQCHPECLPQAMNITCTGR
GPDNCIQCAHYIDGPHCVKTCPAGVMGENNTLVWKYADAGHVCHLCHPNC
TYGCTGPGLEGCPTNGPKIPS

3 — Human EGFRvIII ectodomain cDNA sequence (nucleotides 1-996)

CTGGAAGAGAAGAAAGGCAACTACGTCGTGACCGACCACGGCAGCTGTGT
GCGGGCTTGTGGCGCCGATAGCTACGAGATGGAAGAGGACGGCGTGCGGA
AGTGCAAGAAGTGCGAGGGCCCCTGCCGGAAAGTGTGCAACGGCATCGGC
ATCGGAGAGTTCAAGGACAGCCTGAGCATCAACGCCACCAACATCAAGCA
CTTCAAGAACTGCACCAGCATCAGCGGCGACCTGCACATCCTGCCCGTGG
CCTTTAGAGGCGACAGCTTCACCCACACCCCCCCACTGGACCCCCAGGAA
CTGGACATCCTGAAAACCGTGAAAGAGATCACCGGCTTTCTGCTGATTCA
GGCCTGGCCCGAGAACCGGACAGACCTGCACGCCTTCGAGAACCTGGAAA
TCATCCGGGGCAGGACCAAGCAGCACGGCCAGTTTTCTCTGGCCGTGGTG
TCCCTGAACATCACCAGCCTGGGCCTGCGCGAGCCTGAAAGAAATCAGCGA
CGGCGACGTGATCATCTCCGGCAACAAGAACCTGTGCTACGCCAACACCA
TCAACTGGAAGAAGCTGTTCGGCACCTCCGGCCAGAAAACAAAGATCATC
AGCAACCGGGGCGAGAACAGCTGCAAGGCCACAGGACAAGTGTGCCACGC
CCTGTGTAGCCCTGAGGGCTGTTGGGGACCCGAGCCCAGAGATTGCGTGT
CCTGCAGAAACGTGTCCCGGGGCAGAGAATGCGTGGACAAGTGCAACCTG
CTGGAAGGCGAGCCCCGCGAGTTCGTGGAAAACAGCGAGTGCATCCAGTG
CCACCCCGAGTGTCTGCCCCAGGCCATGAACATTACCTGCACCGGCAGAG
GCCCCGACAACTGTATCCAGTGCGCCCACTACATCGACGGCCCCCACTGC
GTGAAAACCTGTCCTGCTGGCGTGATGGGAGAACAACACCCTCGTGTG
GAAGTACGCCGACGCCGGCCATGTGTGCCACCTGTGTCACCCCCAAT

SEQUENCE TABLE
CDRs are generally indicated in bold and/or underlined

| Seq. ID | Description | Sequence |
|---|---|---|
| 4 | Human EGFRvIII ectodomain amino acid sequence (amino acids 1-332) | LEEKKGNYVVTDHGSCVRACGADSYEMEEDGVRKCKKCEGPCRKVCNGIG IGEFKDSLSINATNIKHFKNCTSISGDLHILPVAFRGDSFTHTPPLDPQE LDILKTVKEITGELLIQAWPENRTDLHAFENLEIIRGRTKQHGQFSLAVV SLNITSLGLRSLKEISDGDVIISGNKNLCYANTINWKKLFGTSGQKTKII SNRGENSCKATGQVCHALCSPEGCWGPEPRDCVSCRNVSRGRECVDKCNL LEGEPREFVENSECIQCHPECLPQAMNITCTGRGPDNCIQCAHYIDGPHC VKTCPAGVMGENNTLVWKYADAGHVCHLCHPN |
| 5 | Human EGFRvIII amino acid residues 15 to 37 | SCVRACGADSYEMEEDGVRKCKK |
| 6 | 5B7 light chain variable region (CDRs in bold) | DVVMTQTPLTLSVTIGQPASISCKSSQSLLDSDGKTYLNWLLQRPGQSPK RLIYLVSKLDSGVPDRFTGSGSGTDFTLKISRVEAEDLGVYYCWQGTHFP QTFGGGTKLEIK |
| 7 | 5B7 CDRL1 | KSSQSLLDSDGKTYLN |
| 8 | 5B7 CDRL2 | LVSKLDS |
| 9 | 5B7 CDRL3 | WQGTHEPQT |
| 10 | 5B7 heavy chain variable region | QIQLVQSGPELKKPGETVMISCKASGYSFTNYGMNWVKQAPEKDLKWMGW INTYTGESRYVDEFKGRFAFSLETSVSIVY̲L̲K̲I̲N̲N̲LKNEDMATYFCARGP NFDVWGTGTTVTVSS |
| 11 | 5B7 CDRH1 | NYGMN |
| 12 | 5B7 CDRH2 | WINTYTGESRYVDEFKG |
| 13 | 5B7 CDRH3 | GPNFDV |
| 14 | 3D12 light chain variable region | EIVLTQSPALMAASPGEKVTITCSVSSSISSSNLHWYQQKSETSPKPWIY GTSNLASGVPVRFSGSGSGTSYSLTISSMEAEDAATYYCQQWSSYPLTFG SGTKLEIK |
| 15 | 3D12 CDRL1 | SVSSSISSSNLH |
| 16 | 3D12 CDRL2 | GTSNLAS |
| 17 | 3D12 CDRL3 | QQWSSYPLT |
| 18 | 3D12 heavy chain variable region | EVQLQQSGPELVKPGSSVRISCKASGYTFTDYNMDWVKQSHGKSLEWIGT INPNNGGTSYNQKFKGKATLTVDKSSSTAYM̲E̲L̲R̲S̲L̲TSEDSAVYYCARVR QLGLWFAYWGQGTLVTVSA |
| 19 | 3D12 CDRH1 | DYNMD |
| 20 | 3D12 CDRH2 | TINPNNGGTSYNQKFKG |
| 21 | 3D12 CDRH3 | VRQLGLWFAY |
| 22 | 1D2 light chain variable region | DVVMTQTPLSLPVSLGDQASISCRSSQSLVHSDGNTYLHWYLQKPGQSPK LLIYKVSNRFSGVPDRFSGSGSGTDFTLKISRVEAEDLGVYFCSQSTHVP WTFGGGTKLEIK |
| 23 | 1D2 CDRL1 | RSSQSLVHSDGNTYLH |
| 24 | 1D2 CDRL2 | KVSNRFS |
| 25 | 1D2 CDRL3 | SQSTHVPWT |
| 26 | 1D2 heavy chain variable region | DVQLQESGPDLVKPSQSLSLTCTVTGYSITSGYSWHWIRQFPGNKLEWMG YIHYSGSTNYNPSLKSRISITRDTSKNQFF̲L̲Q̲L̲SSVTTEDTATYYCTRSP YFDVWGTGTTVTVSSA |
| 27 | 1D2 CDRH1 | SGYSWH |
| 28 | 1D2 CDRH2 | YIHYSGSTNYNPSLKS |

-continued

| SEQUENCE TABLE |
| CDRs are generally indicated in bold and/or underlined |

| Seq. ID | Description | Sequence |
|---|---|---|
| 29 | 1D2 CDRH3 | SPYFDV |
| 30 | 5B7 CAR construct amino acid sequence (with linker and CD8 hinge) | QIQLVQSGPELKKPGETVMISCKASGYSFTNYGMNWVKQAPEKDLKWMGWINTYTGESRYVDEFKGRFAFSLETSVSIVYLKINNLKNEDMATYFCARGPNFDVWGTGTTVTVSSAKTTAPSVYPLAPGSLGGTGGGSGGGSGGGGSDVVMTQTPLTLSVTIGQPASISCKSSQSLLDSDGKTYLNWLLQRPGQSPKRLIYLVSKLDSGVPDRFTGSGSGTDFTLKISRVEAEDLGVYYCWQGTHEPQTFGGGTKLEIKRADAAPTVSIFPPSSKLGVISNSVMYFSSVVPVLQKVNSTTTKPVLRTPSPVHPTGTSQPQRPEDCRPRGSVKGTGLDFA |
| 31 | 5B7 CAR construct nucleotide sequence | GACAGAAGACCTAGGACAGATCCAGTTGGTGCAGTCTGGACCTGAGCTGAAGAAGCCTGGAGAGACAGTCATGATCTCCTGCAAGGCTTCTGGGTATTCCTTCACAAACTATGGAATGAACTGGGTGAAGCAGGCTCCAGAAAAGGATTTAAAGTGGATGGGCTGGATAAACACCTACACTGGAGAGTCAAGATATGTTGATGAATTCAAGGGACGGTTTGCCTTCTCTTTGGAAACCTCTGTTAGTATTGTCTATTTGAAGATCAACAACCTCAAAAATGAGGACATGGCTACATATTTCTGTGCAAGAGGGCCTAATTTCGATGTCTGGGGCACAGGGACCACGGTCACTGTCTCCTCAGCCAAAACAACAGCCCCATCCGTCTATCCCCTGGCCCCTGGAAGCTTGGGAGGTACCGGCGGAAGTGGAGGCGGAGGATCTGGCGGCGGAGGATCCGATGTTGTGATGACCCAGACTCCACTCACTTTGTCGGTTACCATTGGACAACCAGCCTCCATCTCTTGCAAGTCAAGTCAGAGCCTCTTAGATAGTGATGGAAAGACATATTTGAATTGGTTGTTACAGAGGCCAGGCCAGTCTCCAAAGCGCCTAATCTATCTGGTGTCTAAACTGGACTCTGGAGTCCCTGACAGGTTCACTGGCAGTGGATCAGGGACAGATTTCACACTGAAAATCAGCAGAGTGGAGGCTGAGGATTTGGGAGTTTATTATTGCTGGCAAGGTACACATTTTCCTCAGACGTTCGGTGGAGGCACCAAGCTGGAAATCAAACGGGCTGATGCTGCACCAACTGTATCCATCTTCCCACCATCCAGTAAGCTTGGGGTCATCAGCAACTCGGTGATGTACTTCAGTTCTGTCGTGCCAGTCCTTCAGAAAGTGAACTCTACTACTACCAAGCCAGTGCTGCGAACTCCCTCACCTGTGCACCCTACCGGGACATCTCAGCCCCAAAGACCAGAAGATTGTCGGCCCCGTGGCTCAGTGAAGGGGACCGGATTGGACTTCGCCCCTTGGGTCTTCGGTAGGG |
| 32 | 5B7 CAR construct with CD28 intracellular transduction domain (ITD) and CD3zeta ITD (signal peptide underlined) | <u>MLRLLLALNLEPSIQVT</u>GQIQLVQSGPELKKPGETVMISCKASGYSFTNYGMNWVKQAPEKDLKWMGWINTYTGESRYVDEFKGRFAFSLETSVSIVYLKINNLKNEDMATYFCARGPNFDVWGTGTTVTVSSAKTTAPSVYPLAPGSLGGTGGGSGGGSGGGGSDVVMTQTPLTLSVTIGQPASISCKSSQSLLDSDGKTYLNWLLQRPGQSPKRLIYLVSKLDSGVPDRFTGSGSGTDFTLKISRVEAEDLGVYYCWQGTHEPQTFGGGTKLEIKRADAAPTVSIFPPSSKLGVISNSVMYFSSVVPVLQKVNSTTTKPVLRTPSPVHPTGTSQPQRPEDCRPRGSVKGTGLDFAPSKPFWVLVVVGGVLACYSLLVTVAFIIFWVRSKRSRLLHSDYMNMTPRRPGPTRKHYQPYAPPRDFAAYRSASLRVKFSRSADAPAYQQGQNQLYNELNLGRREEYDVLDKRRGRDPEMGGKPQRRKNPQEGLYNELQKDKMAEAYSEIGMKGERRRGKGHDGLYQGLSTATKDTYDALHMQALPPRLE |
| 33 | 3D12 CAR construct amino acid sequence (with linker and CD8 hinge) | EVQLQQSGPELVKPGSSVRISCKASGYTFTDYNMDWVKQSHGKSLEWIGTINPNNGGTSYNQKFKGKATLTVDKSSSTAYMELRSLTSEDSAVYYCARVRQLGLWFAYWGQGTLVTVSAAKTTPPSVYPLAPGSLGGTGGGSGGGSGGGGSEIVLTQSPALMAASPGEKVTITCSVSSSISSSNLHWYQQKSETSPKPWIYGTSNLASGVPVRESGSGSGTSYSLTISSMEAEDDAATYYCQQWSSYPLTFGSGTKLEIKRADAAPTVSIFPPSSKLGVISNSVMYFSSVVPVLQKUNSTTTKPVLRTPSPVHPTGTSQPQRPEDCRPRGSVKGTGLDFA |
| 34 | 3D12 CAR construct with CD28 ITD and CD3zeta ITD (signal peptide underlined) | <u>MLRLLLALNLEPSIQVT</u>GEVQLQQSGPELVKPGSSVRISCKASGYTFTDYNMDWVKQSHGKSLEWIGTINPNNGGTSYNQKFKGKATLTVDKSSSTAYMELRSLTSEDSAVYYCARVRQLGLWFAYWGQGTLVTVSAAKTTPPSVYPLAPGSLGGTGGGSGGGSGGGGSEIVLTQSPALMAASPGEKVTITCSVSSSISSSNLHWYQQKSETSPKPWIYGTSNLASGVPVRESGSGSGTSYSLTISSMEAEDDAATYYCQQWSSYPLTFGSGTKLEIKRADAAPTVSIFPPSSKLGVISNSVMYFSSVVPVLQKVNSTTTKPVLRTPSPVHPTGTSQPQRPEDCRPRGSVKGTGLDFAPSKPFWVLVVVGGVLACYSLLVTVAFIIFWVRSKRSRLLHSDYMNMTPRRPGPTRKHYQPYAPPRDFAAYRSASLRVKESRSADAPAYQQGQNQLYNELNLGRREEYDVLDKRRGRDPEMGGKPQRRKNPQEGLYNELQKDKMAEAYSEIGMKGERRRGKGHDGLYQGLSTATKDTYDALHMQALPPRLE |
| 35 | 1D2 CAR construct amino acid sequence (with linker and CD8 hinge) | DVQLQESGPDLVKPSQSLSLTCTVTGYSITSGYSWHWIRQFPGNKLEWMGYIHYSGSTNYNPSLKSRISITRDTSKNQFFLQLSSVTTEDTATYYCTRSPYFDVWGTGTTVTVSSAKTTPPSVYPLAPGSLGGTGGGSGGGSGGGGSDVVMTQTPLSLPVSLGDQASISCRSSQSLVHSDGNTYLHWYLQKPGQSPKLLIYKVSNRFSGVPDRFSGSGSGTDFTLKISRVEAEDLGVYFCSQSTHVPWTFGGGTKLEIKRADAAPTVSIFPPSSKLGVISNSVMYFSSVVPVLQKVNSTTKPVLRTPSPVHPTGTSQPQRPEDCRPRGSVKGTGLDFA |

SEQUENCE TABLE
CDRs are generally indicated in bold and/or underlined

| Seq. ID | Description | Sequence |
|---|---|---|
| 36 | 1D2 CAR construct with CD28 ITD and CD3zeta ITD (signal peptide underlined) | MLRLLLALNLEPSIQVTGDVQLQESGPDLVKPSQSLSLTCTVTGYSITSG YSWHWIRQFPGNKLEWMGYIHYSGSTNYNPSLKSRISITRDTSKNQFFLQ LSSVTTEDTATYYCTRSPYFDVWGTGTTVTVSSAKTTPPSVYPLAPGSLG TGGGSGGGGSGGGGSDVVMTQTPLSLPVSLGDQASISCRSSQSLVHSDGN TYLHWYLQKPGQSPKLLIYKVSNRFSGVPDRESGSGSGTDETLKISRVEA EDLGVYFCSQSTHVPWTFGGGTKLEIKRADAAPTVSIFPPSSKLGVISNS VMYFSSVVPVLQKVNSTTTKPVLRTPSPVHPTGTSQPQRPEDCRPRGSVK GTGLDFAPSKPFWVLVVVGGVLACYSLLVTVAFIIFWVRSKRSRLLHSDY MNMTPRRPGPTRKHYQPYAPPRDFAAYRSASLRVKESRSADAPAYQQGON QLYNELNLGRREEYDVLDKRRGRDPEMGGKPQRRKNPQEGLYNELQKDKM AEAYSEIGMKGERRRGKGHDGLYQGLSTATKDTYDALHMQALPPRLE |
| 37 | DNA sequence for modular CAR vector (without filler/insert) | ATGCTCAGGCTGCTCTTGGCTCTCAACTTATTCCCTTCAATTCAGTAAC AGGAGGGTCTTCGAGAAGACCTCCTTCTAAGCCCTTTTGGGTGCTGGTGG TGGTTGGTGGGTTCCTGGCTTGCTATAGCTTGCTAGTAACAGTGGCCTTT ATTATTTTCTGGGTGAGGAGTAAGAGGAGCAGGCTCCTGCACAGTGACTA CATGAACATGACTCCCAGGCGGCCCGGACCCACCCGCAAGCATTACCAGC CCTATGCCCCACCACGCGACTTCGCAGCCTATCGCTCCGCTAGCCTGAGA GTGAAGTTCAGCAGGAGCGCAGACGCCCCCGCGTACCAGCAGGGCCAGAA CCAGCTCTATAACGAGCTCAATCTAGGACGAAGAGAGGAGTACGATGTTT TGGACAAGAGACGTGGCCGGGACCCTGAGATGGGGGGAAAGCCGCAGAGA AGGAAGAACCCTCAGGAAGGCCTGTACAATGAACTGCAGAAAGATAAGAT GGCGGAGGCCTACAGTGAGATTGGGATGAAAGGCGAGCGCCGGAGGGGCA AGGGGCACGATGGCCTTTACCAGGGTCTCAGTACAGCCACCAAGGACACC TACGACGCCCTTCACATGCAGGCCCTGCCCCCTCGCCTCGAG |
| 38 | 5B7 Heavy chain variable region nucleotide sequence | CAGATCCAGTTGGTGCAGTCTGGACCTGAGCTGAAGAAGCCTGGAGAGAC AGTCATGATCTCCTGCAAGGCTTCTGGGTATTCCTTCACAAACTATGGAA TGAACTGGGTGAAGCAGGCTCCAGAAAAGGATTTAAAGTGGATGGGCTGG ATAAACACCTACACTGGAGAGTCAAGATATGTTGATGAATTCAAGGGACG GTTTGCCTTCTCTTTGGAAACCTCTGTTAGTATTGTCTATTTGAAGATCA ACAACCTCAAAAATGAGGACATGGCTACATATTTCTGTGCAAGAGGGCCT AATTTCGATGTCTGGGGCACAGGGACCACGGTCACCGTCTCCTCA |
| 39 | 5B7 Light chain variable region nucleotide sequence | GATGTTGTGATGACCCAGACTCCACTCACTTTGTCGGTTACCATTGGACA ACCAGCCTCCATCTCTTGCAAGTCAAGTCAGAGCCTCTTAGATAGTGATG GAAAGACATATTTGAATTGGTTGTTACAGAGGCCAGGCCAGTCTCCAAAG CGCCTAATCTATCTGGTGTCTAAACTGGACTCTGGAGTCCCTGACAGGTT CACTGGCAGTGGATCAGGGACAGATTTCACACTGAAAATCAGCAGAGTGG AGGCTGAGGATTTGGGAGTTTATTATTGCTGGCAAGGTACACATTTTCCT CAGACGTTCGGTGGAGGCACCAAGCTGGAAATCAAA |
| 40 | 3D12 Heavy chain variable region nucleotide sequence | GAGGTCCAGCTGCAACAGTCTGGACCTGAGCTGGTGAAGCCTGGGTCTTC AGTGAGGATATCCTGCAAAGCTTCTGGATACACCATTCACTGACTACAACA TGGACTGGGTGAAGCAGAGCCATGGAAAGAGCCTTGAGTGGATTGGAACT ATTAATCCTAACAATGGTGGTACTAGCTACAACCAGAAGTTCAAGGGCAA GGCCACATTGACTGTTGACAAGTCCTCCAGCACAGCCTACATGGAACTCC GCAGCCTGACATCTGAGGACTCTGCAGTCTATTACTGTGCAAGAGTGAGA CAGCTCGGGCTGTGGTTTGCTTACTGGGGCCAAGGGACTCTGGTCACTGT CTCTGCA |
| 41 | 3D12 Light chain variable region nucleotide sequence | GAAATTGTGCTCACCCAGTCTCCAGCACTCATGGCTGCATCTCCAGGGGA GAAGGTCACCATCACCTGCAGTGTCAGCTCAAGTATAAGTTCCAGCAACT TGCACTGGTACCAGCAGAAGTCAGAAACCTCCCCCAAACCCTGGATTTAT GGCACATCCAACCTGGCTTCTGGAGTCCCTGTTCGCTTCAGTGGCAGTGG ATCTGGGACCTCTTATTCTCTCACAATCAGCAGCATGGAGGCTGAAGATG CTGCCACTTATTACTGTCAACAGTGGAGTAGTTACCCACTCACGTTCGGC TCGGGGACAAAGTTGGAAATAAAA |
| 42 | 1D2 Heavy chain variable nucleotide sequence | GATGTGCAGCTTCAGGAGTCAGGACCTGACCTGGTGAAACCTTCTCAGTC ACTTTCACTCACCTGCACTGTCACTGGCTACTCCATCACCAGTGGTTATA GCTGGCACTGGATCCGGCAGTTTCCAGGAAACAAACTGGAATGGATGGGC TACATACACTACAGTGGTAGCACTAACTACAACCCATCTCTCAAAAGTCG AATCTCTATCACTCGAGACACATCCAAGAACCAGTTCTTCCTGCAGTTGA GTTCTGTGACTACTGAGGACACTGCCACATATTACTGTACAAGAAGCCCG TACTTCGATGTCTGGGGCACAGGGACCACGGTCACCGTCTCCTCA |
| 43 | 1D2 Light chain variable region nucleotide sequence | GATGTTGTGATGACCCAAACTCCACTCTCCCTGCCTGTCAGTCTTGGCGA TCAAGCCTCCATCTCTTGCAGATCTAGTCAGAGCCTTGTGCACAGTGATG GAAACACCTATTTACATTGGTACCTGCAGAAGCCAGGCCAGTCTCCAAAG CTCCTGATCTACAAAGTTTCCAACCGATTTTCTGGGGTCCCAGACAGGTT CAGTGGCAGTGGATCAGGGACAGATTTCACACTCAAGATCAGCAGAGTGG |

-continued

---

SEQUENCE TABLE
CDRs are generally indicated in bold and/or underlined

---

| Seq. ID | Description | Sequence |
|---|---|---|
| | | AGGCTGAGGATCTGGGAGTTTATTTCTGCTCTCAAAGTACACATGTTCCG TGGACGTTCGGTGGAGGCACCAAGCTGGAAATCAAA |
| 44 | 5B7 scFV (linker twice-underlined, any suitable known linker may be used) | QIQLVQSGPELKKPGETVMISCKASGYSFTNYGMNWVKQAPEKDLKWMGW INTYTGESRYVDEFKGRFAFSLETSVSIVYLKINNLKNEDMATYFCARGP NFDVWGTGTTVTVSSAKTTAPSVYPLAPGSLG<u>GTGGGSGGGGSGGGGS</u>DV VMTQTPLTLSVTIGQPASISCKSSQSLLDSDGKTYLNWLLQRPGQSPKRL IYLVSKLDSGVPDRFTGSGSGTDFTLKISRVEAEDLGVYYC<u>WQGTHEPOT</u> FGGGTKLEIKRADAAPTVSIFPPSSKLG |
| 45 | 3D12 scFV (linker twice-underlined, any suitable known linker may be used) | EVQLQQSGPELVKPGSSVRISCKASGYTFTDYNMDWVKQSHGKSLEWIGT INPNNGGTSYNQKFKGKATLTVDKSSSTAYMELRSLTSEDSAVYYCARVR QLGLWFAYWGQGTLVTVSAAKTTPPSVYPLAPGSLG<u>GTGGGSGGGGSGGG GS</u>EIVLTQSPALMAASPGEKVTITCSVSSSISSSNLHWYQQKSETSPKPW IYGTSNLASGVPVRESGSGSGTSYSLTISSMEAEDAATYYCQQWSSYPLT FGSGTKLEIKRADAAPTVSIFPPSSKLG |
| 46 | 1D2 scFV (linker twice-underlined, any suitable known linker may be used) | DVQLQESGPDLVKPSQSLSLTCTVTGYSITSGYSWHWIRQFPGNKLEWMG YIHYSGSTNYNPSLKSRISITRDTSKNQFFLQLSSVTTEDTATYYCTRSP YFDVWGTGTTVTVSSAKTTPPSVYPLAPGSL<u>GTGGGSGGGGSGGGGS</u>DVV MTQTPLSLPVSLGDQASISCRSSQSLVHSDGNTYLHWYLQKPGQSPKLLI YKVSNRFSGVPDRESGSGSGTDFTLKISRVEAEDLGVYFC<u>SQSTHVPWT</u>F GGGTKLEIKRADAAPTVSIFPPSSKLG |
| 47 | Linker (exemplary linker, any suitable linker may be used) | GGGSGGGGSGGGGS |
| 48 | Amino acid residues 15 to 37 of EGFRvIII, with Ser15 to Ala mutation | ACVRACGADSYEMEEDGVRKCKK |
| 49 | Amino acid residues 15 to 37 of EGFRvIII, with Cys16 to Ala mutation | SAVRACGADSYEMEEDGVRKCKK |
| 50 | Amino acid residues 15 to 37 of EGFRvIII, with Val17 to Ala mutation | SCARACGADSYEMEEDGVRKCKK |
| 51 | Amino acid residues 15 to 37 of EGFRvIII, with Arg18 to Ala mutation | SCVAACGADSYEMEEDGVRKCKK |
| 52 | Amino acid residues 15 to 37 of EGFRvIII, with Cys20 to Ala mutation | SCVRAAGADSYEMEEDGVRKCKK |
| 53 | Amino acid residues 15 to 37 of EGFRvIII, with Gly21 to Ala mutation | SCVRACAADSYEMEEDGVRKCKK |
| 54 | Amino acid residues 15 to 37 of EGFRvIII, with Asp23 to Ala mutation | SCVRACGAASYEMEEDGVRKCKK |
| 55 | Amino acid residues 15 to 37 of EGFRvIII, with Ser24 to Ala mutation | SCVRACGADAYEMEEDGVRKCKK |
| 56 | Amino acid residues 15 to 37 of EGFRvIII, with Tyr25 to Ala mutation | SCVRACGADSAEMEEDGVRKCKK |
| 57 | Amino acid residues 15 to 37 of EGFRvIII, with Glu26 to Ala mutation | SCVRACGADSYAMEEDGVRKCKK |
| 58 | Amino acid residues 15 to 37 of EGFRvIII, with Met27 to Ala mutation | SCVRACGADSYEAEEDGVRKCKK |

-continued

| SEQUENCE TABLE |
| CDRs are generally indicated in bold and/or underlined |

| Seq. ID | Description | Sequence |
|---|---|---|
| 59 | Amino acid residues 15 to 37 of EGFRvIII, with Glu28 to Ala mutation | SCVRACGADSYEMAEDGVRKCKK |
| 60 | Amino acid residues 15 to 37 of EGFRvIII, with Glu29 to Ala mutation | SCVRACGADSYEMEADGVRKCKK |
| 61 | Amino acid residues 15 to 37 of EGFRvIII, with Asp30 to Ala mutation | SCVRACGADSYEMEEAGVRKCKK |
| 62 | Amino acid residues 15 to 37 of EGFRvIII, with Gly31 to Ala mutation | SCVRACGADSYEMEEDAVRKCKK |
| 63 | Amino acid residues 15 to 37 of EGFRvIII, with Val32 to Ala mutation | SCVRACGADSYEMEEDGARKCKK |
| 64 | Amino acid residues 15 to 37 of EGFRvIII, with Arg33 to Ala mutation | SCVRACGADSYEMEEDGVAKCKK |
| 65 | Amino acid residues 15 to 37 of EGFRvIII, with Lys34 to Ala mutation | SCVRACGADSYEMEEDGVRACKK |
| 66 | Amino acid residues 15 to 37 of EGFRvIII, with Cys35 to Ala mutation | SCVRACGADSYEMEEDGVRKAKK |
| 67 | Amino acid residues 15 to 37 of EGFRvIII, with Lys36 to Ala mutation | SCVRACGADSYEMEEDGVRKCAK |
| 68 | Amino acid residues 15 to 37 of EGFRvIII, with Lys37 to Ala mutation | SCVRACGADSYEMEEDGVRKCKA |
| 69 | Amino acid residues 1 to 76 of EGFRvIII | LEEKKGNYVVTDHGSCVRACGADSYEMEEDGVRKCKK CEGPCRKVCNGIGIGEFKDSLSINATNIKHFKNCTSI SG |
| 70 | Amino acid residues 3 to 37 of EGFRvIII | EKKGNYVVTDHGSCVRACGADSYEMEEDGVRKCKK |
| 71 | Amino acid residues 1 to 18 of EGFRvill | LEEKKGNYVVTDHGSCVR |
| 72 | 5B7 Shorter scFv (linker twice-underlined, any suitable known linker may be used) | QIQLVQSGPELKKPGETVMISCKASGYSFTNYGMNWVKQAPEKDLKWMGW INTYTGESRYVDEFKGRFAFSLETSVSIVYLKINNLKNEDMATYFCARGP NFDVWGTGTTVTVSS<u>GTGGGSGGGGSGGGGS</u>DVVMTQTPLTLSVTIGQPA SISCKSSQSLLDSDGKTYLNWLLQRPGQSPKRLIYLVSKLDSGVPDRFTG SGSGTDFTLKISRVEAEDLGVYYCWQGTHEPQTFGGGTKLEIK |
| 73 | 5B7 scFv consensus (linker twice-underlined, any suitable known linker may be used) | QIQLVQSGPELKKPGETVMISCKASGYSFTNYGMNWVKQAPEKDLKWMGW INTYTGESRYVDEFKGRFAFSLETSVSIVYLKINNLKNEDMATYFCARGP NFDVWGTGTTVTVSS<u>[Linker]</u>DVVMTQTPLTLSVTIGQPASISCKSSQS LLDSDGKTYLNWLLQRPGQSPKRLIYLVSKLDSGVPDRFTGSGSGTDETL KISRVEAEDLGVYYCWQGTHFPQTFGGGTKLEI |

SEQUENCE TABLE
CDRs are generally indicated in bold and/or underlined

| Seq. ID | Description | Sequence |
|---|---|---|
| 74 | 5B7 CAR consensus (linker twice-underlined, any suitable known linker may be used) | QIQLVQSGPELKKPGETVMISCKASGYSFTNYGMNWVKQAPEKDLKWMGW INTYTGESRYVDEFKGRFAFSLETSVSIVYLKINNLKNEDMATYFCARGP NFDVWGTGTTVTVSS[<u>Linker</u>]DVVMTQTPLTLSVTIGQPASISCKSSQS LLDSDGKTYLNWLLQRPGQSPKRLIYLVSKLDSGVPDRFTGSGSGTDFTL KISRVEAEDLGVYYCWQGTHFPQTFGGGTKLEIVISNSVMYFSSVVPVLQ KVNSTTTKPVLRTPSPVHPTGTSQPQRPEDCRPRGSVKGTGLDFAPSKPF WVLVVVGGVLACYSLLVTVAFIIFWVRSKRSRLLHSDYMNMTPRRPGPTR KHYQPYAPPRDFAAYRSASLRVKFSRSADAPAYQQGQNQLYNELNLGRRE EYDVLDKRRGRDPEMGGKPQRRKNPQEGLYNELQKDKMAEAYSEIGMKGE RRRGKGHDGLYQGLSTATKDTYDALHMQALPPRLE |
| 75 | 3D12 Shorter scFV (linker twice-underlined, any suitable known linker may be used) | EVQLQQSGPELVKPGSSVRISCKASGYTFTDYNMDWVKQSHGKSLEWIGT INPNNGGTSYNQKFKGKATLTVDKSSSTAYMELR<u>SLTSEDSAVYYCARVR QLGLWFAY</u>WGQGTLVTVSA<u>GTGGGSGGGGSGGGGS</u>EIVLTQSPALMAA<u>SP GEKVTITCSVSSISSSNLH</u>WYQQKSETSPKPWIYGTSNLASGVPVRESG SGSGTSYS<u>LTISSMEAEDAATYYCQQWSSYPLT</u>FGSGTKLEIK |
| 76 | 3D12 scFV consensus (linker twice-underlined, any suitable known linker may be used) | EVQLQQSGPELVKPGSSVRISCKASGYTFTDYNMDWVKQSHGKSLEWIGT INPNNGGTSYNQKFKGKATLTVDKSSSTAYMELR<u>SLTSEDSAVYYCARVR QLGLWFAY</u>WGQGTLVTVSA[<u>Linker</u>]EIVLTQSPALMAASPGEKVTIT<u>CS VSSSISSSNLH</u>WYQQKSETSPKPWIYGTSNLASGVPVRESGSGSGTSYS<u>L TISSMEAEDAATYYCQQWSSYPLT</u>FGSGTKLEIK |
| 77 | 3D12 CAR consensus (linker twice-underlined, any suitable known linker may be used) | EVQLQQSGPELVKPGSSVRISCKASGYTFTDYNMDWVKQSHGKSLEWIGT INPNNGGTSYNQKFKGKATLTVDKSSSTAYMELR<u>SLTSEDSAVYYCARVR QLGLWFAY</u>WGQGTLVTVSA[<u>Linker</u>]EIVLTQSPALMAASPGEKVTIT<u>CS VSSSISSSNLH</u>WYQQKSETSPKPWIYGTSNLASGVPVRESGSGSGTSYS<u>L TISSMEAEDAATYYCQQWSSYPLT</u>FGSGTKLEIKVISNSVMYFSSVVPVL QKVNSTTTKPVLRTPSPVHPTGTSQPQRPEDCRPRGSVKGTGLDFAPSKP FWVLVVVGGVLACYSLLVTVAFIIFWVRSKRSRLLHSDYMNMTPRRPGPT RKHYQPYAPPRDFAAYRSASLRVKESRSADAPAYQQGQNQLYNELNLGRR EEYDVLDKRRGRDPEMGGKPQRRKNPQEGLYNELQKDKMAEAYSEIGMKG ERRRGKGHDGLYQGLSTATKDTYDALHMQALPPRLE |
| 78 | 1D2 Shorter scFV (linker twice-underlined, any suitable known linker may be used) | DVQLQESGPDLVKPSQSLSLTCTVTGYSITSGYSWHWIRQFPGNKLEWMG YIHYSGSTNYNPSLKSRISITRDTSKNQFF<u>LQLSSVTTEDTATYYCTRSP YFDV</u>WGTGTTVTVSSA<u>GTGGGSGGGGSGGGGS</u>DVVMTQTPLSLPVSLGDQ <u>ASISCRSSQSLVHSDGNTYLH</u>WYLQKPGQSPKLLIYKVSNRFSGVPDRES GSGSGTDFTLKISRVEAEDLGVYFCSQSTHVPWTFGGGTKLEIK |
| 79 | 1D2 Consensus scFV (linker twice-underlined, any suitable known linker may be used) | DVQLQESGPDLVKPSQSLSLTCTVTGYSITSGYSWHWIRQFPGNKLEWMG YIHYSGSTNYNPSLKSRISITRDTSKNQFF<u>LQLSSVTTEDTATYYCTRSP YFDV</u>WGTGTTVTVSSA[<u>Linker</u>]DVVMTQTPLSLPVSLGDQASISCRS<u>SQ SLVHSDGNTYLH</u>WYLQKPGQSPKLLIYKVSNRFSGVPDRESGSGSGTDET LKISRVEAEDLGVYFCSQSTHVPWTFGGGTKLEIK |
| 80 | 1D2 CAR Consensus (linker twice-unerlined, any suitable known linker may be used) | DVQLQESGPDLVKPSQSLSLTCTVTGYSITSGYSWHWIRQFPGNKLEWMG YIHYSGSTNYNPSLKSRISITRDTSKNQFF<u>LQLSSVTTEDTATYYCTRSP YFDV</u>WGTGTTVTVSSA[<u>Linker</u>]DVVMTQTPLSLPVSLGDQASISCRS<u>SQ SLVHSDGNTYLH</u>WYLQKPGQSPKLLIYKVSNRFSGVPDRESGSGSGTDET LKISRVEAEDLGVYFCSQSTHVPWTFGGGTKLEIKVISNSVMYFSSVVPV LQKVNSTTTKPVLRTPSPVHPTGTSQPQRPEDCRPRGSVKGTGLDFAPSK PFWVLVVVGGVLACYSLLVTVAFIIFWVRSKRSRLLHSDYMNMTPRRPGP TRKHYQPYAPPRDFAAYRSASLRVKFSRSADAPAYQQGQNQLYNELNLGR REEYDVLDKRRGRDPEMGGKPQRRKNPQEGLYNELQKDKMAEAYSEIGMK GERRRGKGHDGLYQGLSTATKDTYDALHMQALPPRLE |
| 81 | 3GGGGS-flexible linker (exemplary) and human CD8 hinge | GGGGSGGGGSGGGGSTTTPAPRPPTPAPTIASQPLSLRPEACRPAAGGAV HTRGLDFACD |

| Seq. ID | Description | Sequence |
|---------|-------------|----------|
| 82 | Amino acid sequence for 3D12 bi-specific T cell engager exemplary sequence Linker sequences underlined, any suitable known linker may be used CD3-specific scFv engager shown in bold | EVQLQQSGPELVKPGSSVRISCKASGYTFTDYNMDWVKQSHGKSLEWIGT INPNNGGTSYNQKFKGKATLTVDKSSSTAYMELRSLTSEDSAVYYCARVR QLGLWFAYWGQGTLVTVSAAKTTPPSVYPLAPGSL<u>GGTGGGSGGGGSGGG</u> <u>GS</u>EIVLTQSPALMAASPGEKVTITCSVSSSISSSNLHWYQQKSETSPKPW IYGTSNLASGVPVRESGSGSGTSYSLTISSMEAEDAATYYCQQWSSYPLT FGSGTKLEIKRADAAPTVSIFPPSSKLGDLGGGGSRDDDIKLQQSGAELA RPGASVKMSCKTSGYTFTRYTMHWVKQRPGQGLEWIGY INPSRGYTNYNQ KFKDKATLTTDKSSSTAYMQLSSLTSEDSAVYYCARYYDDHYCLDYWGQG TTLTVSSVE<u>GGSGGGSGGSGGSGGSGG</u>VDDIQLTQSPAIMSASPGEKVTMTCRA SSSVSYMNWYQQKSGTSPKRWIYDTSKVASGVPYRFSGSGSGTSYSLTIS SMEAEDAATYYCQQWSSNPLTFGAGTKLELK |
| 83 | Linker of the L17-CD8 construct Restriction site scar underlined | <u>PL</u>GGGGSGGGGSGGGGSGGTTTPAPRPPTPAPTIASQPLSLRPEACRPAA GGAVHTRGLDFACD |
| 84 | Linker of the 45CD8h construct Restriction site scar underlined | <u>PL</u>TTTPAPRPPTPAPTIASQPLSLRPEACRPAAGGAVHTRGLDFACD |
| 85 | Linker of the 35CD8h construct Restriction site scar underlined | <u>PL</u>PAPTIASQPLSLRPEACRPAAGGAVHTRGLDFACD |
| 86 | Linker of the 15CD8h construct Restriction site scar underlined | <u>PL</u>AGGAVHTRGLDFACD |
| 87 | 18-mer prior art linker sequence (Andris-Widhopf et al., 2011) | GGSSRSSSSGGGGSGGGG |
| 88 | G$_4$S linker (5-mer) | GGGGS |
| 89 | (G$_4$S)$_3$ linker (15-mer) | GGGGSGGGGSGGGGS |
| 90 | (G$_4$S)$_4$ linker (20-mer) | GGGGSGGGGSGGGGSGGGGS |
| 91 | Human EGFRvIII ectodomain amino acid sequence (amino acids 1-354) | LEEKKGNYVVTDHGSCVRACGADSYEMEEDGVRKCKKCEGPCRKVCNGIG IGEFKDSLSINATNIKHFKNCTSISGDLHILPVAFRGDSFTHTPPLDPQE LDILKTVKEITGELLIQAWPENRTDLHAFENLEIIRGRTKQHGQFSLAVV SLNITSLGLRSLKEISDGDVIISGNKNLCYANTINWKKLFGTSGQKTKII SNRGENSCKATGQVCHALCSPEGCWGPEPRDCVSCRNVSRGRECVDKCNL LEGEPREFVENSECIQCHPECLPQAMNITCTGRGPDNCIQCAHYIDGPHC VKTCPAGVMGENNTLVWKYADAGHVCHLCHPNCTYGCTGPGLEGCPTNGP KIPS |
| 92 | 17AA poly-glycine linker | GGGGSGGGGSGGGGSGG |

The invention claimed is:

1. An antigen-binding agent comprising an antigen-binding domain of an antibody that specifically binds to epidermal growth factor receptor variant III (EGFRvIII), wherein the antigen-binding domain comprises:

a. a CDRL1 comprising or consisting essentially of the amino acid sequence set forth in SEQ ID NO: 15, a CDRL2 comprising or consisting essentially of the amino acid sequence set forth in SEQ ID NO:16, a CDRL3 comprising or consisting essentially of the amino acid sequence set forth in SEQ ID NO: 17, a CDRH1 comprising or consisting essentially of the amino acid sequence set forth in SEQ ID NO:19, a CDRH2 comprising or consisting essentially of the amino acid sequence set forth in SEQ ID NO:20 and a CDRH3 comprising or consisting essentially of the amino acid sequence set forth in SEQ ID NO:21;

b. a CDRL1 comprising or consisting essentially of the amino acid sequence set forth in SEQ ID NO: 7, a CDRL2 comprising or consisting essentially of the amino acid sequence set forth in SEQ ID NO:8, a CDRL3 comprising or consisting essentially of the amino acid sequence set forth in SEQ ID NO:9, a CDRH1 comprising or consisting essentially of the amino acid sequence set forth in SEQ ID NO:11, a CDRH2 comprising or consisting essentially of the amino acid sequence set forth in SEQ ID NO:12 and a CDRH3 comprising or consisting essentially of the amino acid sequence set forth in SEQ ID NO:13, or c. a CDRL1 comprising or consisting essentially of the amino acid sequence set forth in SEQ ID NO: 23, a CDRL2 comprising or consisting essentially of the amino acid sequence set forth in SEQ ID NO:24, a CDRL3 comprising or consisting essentially of the amino acid sequence set forth in SEQ ID NO:25, a CDRH1 comprising or consisting essentially of the amino acid sequence set forth in SEQ ID NO:27, a CDRH2 comprising or consisting essentially of the amino acid sequence set forth in SEQ ID NO:28 and a CDRH3 comprising or consisting essentially of the amino acid sequence set forth in SEQ ID NO:29.

2. The antigen-binding agent of claim 1, wherein the antigen-binding domain comprises humanized framework amino acid sequences.

3. The antigen-binding agent of claim 1, wherein the antigen-binding agent is an antibody, an antigen-binding fragment thereof, a chimeric antigen receptor, a bi-specific T-cell engager, a bispecific killer cell engager, or a trispecific killer cell engager.

4. The antigen-binding agent of claim 3, wherein the antigen-binding agent is an antibody or an antigen-binding fragment thereof which specifically binds to EGFRvIII and is selected from the group consisting of:

a. an antibody or an antigen-binding fragment thereof comprising a heavy chain variable region comprising an amino acid sequence at least 80% identical to the amino acid sequence of set forth in SEQ ID NO:18 and/or a light chain variable region comprising an amino acid sequence at least 80% identical to the amino acid sequence set forth in SEQ ID NO: 14;

b. an antibody or an antigen-binding fragment thereof comprising a heavy chain variable region comprising an amino acid sequence at least 80% identical to the amino acid sequence of set forth in SEQ ID NO:10 and/or a light chain variable region comprising an amino acid sequence at least 80% identical to the amino acid sequence set forth in SEQ ID NO:6, or c. an antibody or an antigen-binding fragment thereof comprising a heavy chain variable region comprising an amino acid sequence at least 80% identical to the amino acid sequence of set forth in SEQ ID NO:26 and/or a light chain variable region comprising an amino acid sequence at least 80% identical to the amino acid sequence set forth in SEQ ID NO: 22.

5. The antigen-binding agent of claim 3, wherein the antigen-binding agent is a chimeric antigen receptor, a bi-specific T-cell engager, a bispecific killer cell engager or a trispecific killer cell engager and wherein the antigen-binding domain comprises:

a. an amino acid sequence at least 80% identical to the amino acid sequence of the heavy chain variable region set forth in SEQ ID NO:18 and/or an amino acid sequence at least 80% identical to the amino acid sequence of the light chain variable region set forth in SEQ ID NO: 14;

b. an amino acid sequence at least 80% identical to the amino acid sequence of the heavy chain variable region set forth in SEQ ID NO:10 and/or an amino acid sequence at least 80% identical to the amino acid sequence of the light chain variable region set forth in SEQ ID NO: 6, or c. an amino acid sequence at least 80% identical to the amino acid sequence of the heavy chain variable region set forth in SEQ ID NO:26 and/or an amino acid sequence at least 80% identical to the amino acid sequence of the light chain variable region set forth in SEQ ID NO: 22.

6. The antigen-binding agent of claim 5, wherein the chimeric antigen receptor further comprises:

a. a transmembrane domain, wherein the antigen-binding domain is optionally connected to the transmembrane domain by a spacer;

b. at least one intracellular signaling domain; and c. optionally at least one costimulatory domain.

7. The antigen-binding agent of claim 6, wherein the intracellular signaling domain is selected from the group consisting of CD3 zeta, CD3 gamma, CD3 delta, CD3 epsilon, common FcR gamma (FCERIG), FcR beta (Fc Epsilon Rib), CD79a, CD79b, Fcgamma Rlla, DAP10, and DAP12.

8. The antigen-binding agent of claim 6, wherein the chimeric antigen receptor comprises at least one costimulatory domain.

9. The antigen-binding agent of claim 8, wherein the costimulatory domain is selected from the group consisting of CD28, CD27, 4-1BB, OX40, CD7, B7-1 (CD80), B7-2 (CD86), CD30, CD40, PD-1, ICOS, lymphocyte function-associated antigen-1 (LFA-1), CD2, LIGHT, NKG2C, B7-H3, a ligand that specifically binds with CD83, CDS, ICAM-1, GITR, BAFFR, HVEM (LIGHTR), SLAMF7, NKp80 (KLRF1), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD1d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D and a combination thereof.

10. The antigen-binding agent of claim 5, wherein the chimeric antigen receptor comprises:

a. an amino acid sequence at least 80% identical to the amino acid sequence set forth in SEQ ID NO:33;

b. an amino acid sequence at least 80% identical to the amino acid sequence set forth in SEQ ID NO:34 or as set forth in SEQ ID NO:77;

c. an amino acid sequence at least 80% identical to the amino acid sequence set forth in SEQ ID NO:30;

d. an amino acid sequence at least 80% identical to the amino acid sequence set forth in SEQ ID NO:32 or as set forth in SEQ ID NO:74;

e. an amino acid sequence at least 80% identical to the amino acid sequence set forth in SEQ ID NO:35, or f. an amino acid sequence at least 80% identical to the amino acid sequence set forth in SEQ ID NO:36 or as set forth in SEQ ID NO:80.

11. An isolated cell population engineered to express the chimeric antigen receptor of claim 5.

12. The isolated cell population of claim 11, wherein the isolated cell population comprises immune cells.

13. The isolated cell population of claim 12, wherein the immune cells comprise T cells, Natural Killer (NK) cells, cytotoxic T cells, regulatory T cells or a combination thereof.

14. A pharmaceutical composition comprising the isolated cell population of claim 11 and a pharmaceutically acceptable excipient.

15. A method of treating a subject having a cancer associated with EGFRvIII expression, the method comprising administering the isolated cell population of claim 11.

16. The antigen-binding agent of claim 3, wherein the antigen-binding agent is a bi-specific T-cell engager comprising;

a. a CDRL1 comprising or consisting essentially of the amino acid sequence set forth in SEQ ID NO:15, a CDRL2 comprising or consisting essentially of the amino acid sequence set forth in SEQ ID NO:16, a CDRL3 comprising or consisting essentially of the amino acid sequence set forth in SEQ ID NO:17, a CDRH1 comprising or consisting essentially of the amino acid sequence set forth in SEQ ID NO:19, a CDRH2 comprising or consisting essentially of the amino acid sequence set forth in SEQ ID NO:20 and a CDRH3 comprising or consisting essentially of the amino acid sequence set forth in SEQ ID NO:21, and wherein the bi-specific T-cell engager optionally comprises a CDR3-specific binding domain;

b. an amino acid sequence at least 80% identical to the amino acid sequence of the heavy chain variable region set forth in SEQ ID NO:18 and/or an amino acid sequence at least 80% identical to the amino acid sequence of the light chain variable region set forth in SEQ ID NO:14 and wherein the bi-specific T-cell engager optionally comprises a CDR3-specific binding domain or, c. wherein the bi-specific T-cell engager optionally comprises a CDR3-specific binding domain and an amino acid sequence at least 80% identical to SEQ ID NO:82.

17. The antigen-binding agent of claim 1, wherein the antigen-binding domain is in the form of a single chain variable fragment (scFv).

18. The antigen-binding agent of claim 17, wherein the scFv structure is defined by the formula VH-linker-VL.

19. An isolated nucleic acid molecule encoding the antigen-binding agent of claim 1.

20. A vector comprising a nucleic acid molecule encoding the antigen-binding agent of claim 1.

21. An isolated cell comprising or expressing the antigen-binding agent of claim 1.

22. A method of treating subject having a cancer associated with EGFRvIII expression, the method comprising administering the antigen-binding agent of claim 1.

23. The antigen-binding agent of claim 1, wherein the antigen-binding agent comprises:

a. the amino acid sequence of set forth in SEQ ID NO:45;

b. an amino acid sequence of at least 80% identical to the amino acid sequence of set forth in SEQ ID NO:45 and comprising a CDRL1 comprising or consisting essentially of the amino acid sequence set forth in SEQ ID NO:15, a CDRL2 comprising or consisting essentially of the amino acid sequence set forth in SEQ ID NO: 16, a CDRL3 comprising or consisting essentially of the amino acid sequence set forth in SEQ ID NO:17, a CDRH1 comprising or consisting essentially of the amino acid sequence set forth in SEQ ID NO:19, a CDRH2 comprising or consisting essentially of the amino acid sequence set forth in SEQ ID NO: 20 and a CDRH3 comprising or consisting essentially of the amino acid sequence set forth in SEQ ID NO:21;

b. the amino acid sequence of set forth in SEQ ID NO:44;

c. an amino acid sequence of at least 80% identical to the amino acid sequence of set forth in SEQ ID NO:44 and comprising a CDRL1 comprising or consisting essentially of the amino acid sequence set forth in SEQ ID NO:7, a CDRL2 comprising or consisting essentially of the amino acid sequence set forth in SEQ ID NO:8, a CDRL3 comprising or consisting essentially of the amino acid sequence set forth in SEQ ID NO:9, a CDRH1 comprising or consisting essentially of the amino acid sequence set forth in SEQ ID NO:11, a CDRH2 comprising or consisting essentially of the amino acid sequence set forth in SEQ ID NO: 12 and a CDRH3 comprising or consisting essentially of the amino acid sequence set forth in SEQ ID NO:13;

c. the amino acid sequence of set forth in SEQ ID NO:46; or d. an amino acid sequence of at least 80% identical to the amino acid sequence of set forth in SEQ ID NO:46 and comprising CDRL1 comprising or consisting essentially of the amino acid sequence set forth in SEQ ID NO:23, a CDRL2 comprising or consisting essentially of the amino acid sequence set forth in SEQ ID NO:24, a CDRL3 comprising or consisting essentially of the amino acid sequence set forth in SEQ ID NO:25, a CDRH1 comprising or consisting essentially of the amino acid sequence set forth in SEQ ID NO:27, a CDRH2 comprising or consisting essentially of the amino acid sequence set forth in SEQ ID NO: 28 and a CDRH3 comprising or consisting essentially of the amino acid sequence set forth in SEQ ID NO:29.

* * * * *

SEQUENCE LISTING

<160> NUMBER OF SEQ ID NOS: 92

<210> SEQ ID NO 1
<211> LENGTH: 1863
<212> TYPE: DNA
<213> ORGANISM: Homo sapiens

<400> SEQUENCE: 1

```
ctggaggaaa agaaagtttg ccaaggcacg agtaacaagc tcacgcagtt gggcactttt        60
gaagatcatt ttctcagcct ccagaggatg ttcaataact gtgaggtggt ccttgggaat       120
ttggaaatta cctatgtgca gaggaattat gatctttcct tcttaaagac catccaggag       180
gtggctggtt atgtcctcat tgccctcaac acagtggagc gaattccttt ggaaaacctg       240
cagatcatca gaggaaatat gtactacgaa aattcctatg ccttagcagt cttatctaac       300
tatgatgcaa ataaaaccgg actgaaggag ctgcccatga aaatttaca ggaaatcctg        360 catggcgccg tgcggttcag caacaaccct gccctgtgca acgtggagag catccagtgg       420
cgggacatag tcagcagtga ctttctcagc aacatgtcga tggacttcca gaaccacctg       480
ggcagctgcc aaaagtgtga tccaagctgt cccaatggga gctgctgggg tgcaggagag       540
gagaactgcc agaaactgac caaaatcatc tgtgcccagc agtgctccgg gcgctgccgt       600
ggcaagtccc ccagtgactg ctgccacaac cagtgtgctg caggctgcac aggcccccgg       660
gagagcgact gcctggtctg ccgcaaattc cgagacgaag ccacgtgcaa ggacacctgc       720
cccccactca tgctctacaa ccccaccacg taccagatgg atgtgaaccc cgagggcaaa       780
tacagctttg gtgccacctg cgtgaagaag tgtccccgta attatgtggt gacagatcac       840
ggctcgtgcg tccgagcctg tggggccgac agctatgaga tggaggaaga cggcgtccgc       900
aagtgtaaga gtgcgaagg gccttgccgc aaagtgtgta cggaatagg tattggtgaa        960 tttaaagact cactctccat aaatgctacg aatattaaac acttcaaaaa ctgcacctcc      1020
atcagtggcg atctccacat cctgccggtg gcatttaggg gtgactcctt cacacatact      1080
cctcctctgg atccacagga actggatatt ctgaaaaccg taaggaaat cacagggttt       1140 ttgctgattc aggcttggcc tgaaaacagg acggacctcc atgcctttga gaacctagaa      1200
atcatacgcg gcaggaccaa gcaacatggt cagttttctc ttgcagtcgt cagcctgaac      1260
ataacatcct tgggattacg ctccctcaag gagataagtg atggagatgt gataatttca      1320
ggaaacaaaa atttgtgcta tgcaaataca ataaactgga aaaaactgtt tgggacctcc      1380
ggtcagaaaa ccaaaattat aagcaacaga ggtgaaaaca gctgcaaggc cacaggccag      1440
gtctgccatg ccttgtgctc ccccgagggc tgctgggggc cggagcccag ggactgcgtc      1500 tcttccgga atgtcagccg aggcagggaa tgcgtggaca agtgcaacct tctggagggt       1560
gagccaaggg agtttgtgga gaactctgag tgcatacagt gccacccaga gtgcctgcct      1620
caggccatga acatcacctg cacaggacgg ggaccagaca actgtatcca gtgtgcccac      1680
tacattgacg gcccccactg cgtcaagacc tgcccggcag gagtcatggg agaaaacaac      1740
accctggtct ggaagtacgc agacgccggc catgtgtgcc acctgtgcca tccaaactgc      1800
acctacggat gcactgggcc aggtcttgaa ggctgtccaa cgaatgggcc taagatcccg      1860
tcc                                                                     1863
```

<210> SEQ ID NO 2
<211> LENGTH: 621
<212> TYPE: PRT
<213> ORGANISM: Homo sapiens

<400> SEQUENCE: 2

```
Leu Glu Glu Lys Lys Val Cys Gln Gly Thr Ser Asn Lys Leu Thr Gln
1               5                   10                  15

Leu Gly Thr Phe Glu Asp His Phe Leu Ser Leu Gln Arg Met Phe Asn
            20                  25                  30

Asn Cys Glu Val Val Leu Gly Asn Leu Glu Ile Thr Tyr Val Gln Arg
        35                  40                  45

Asn Tyr Asp Leu Ser Phe Leu Lys Thr Ile Gln Glu Val Ala Gly Tyr
    50                  55                  60

Val Leu Ile Ala Leu Asn Thr Val Glu Arg Ile Pro Leu Glu Asn Leu
65                  70                  75                  80

Gln Ile Ile Arg Gly Asn Met Tyr Tyr Glu Asn Ser Tyr Ala Leu Ala
                85                  90                  95

Val Leu Ser Asn Tyr Asp Ala Asn Lys Thr Gly Leu Lys Glu Leu Pro
            100                 105                 110

Met Arg Asn Leu Gln Glu Ile Leu His Gly Ala Val Arg Phe Ser Asn
            115                 120                 125

Asn Pro Ala Leu Cys Asn Val Glu Ser Ile Gln Trp Arg Asp Ile Val
    130                 135                 140

Ser Ser Asp Phe Leu Ser Asn Met Ser Met Asp Phe Gln Asn His Leu
145                 150                 155                 160

Gly Ser Cys Gln Lys Cys Asp Pro Ser Cys Pro Asn Gly Ser Cys Trp
                165                 170                 175

Gly Ala Gly Glu Glu Asn Cys Gln Lys Leu Thr Lys Ile Ile Cys Ala
            180                 185                 190

Gln Gln Cys Ser Gly Arg Cys Arg Gly Lys Ser Pro Ser Asp Cys Cys
            195                 200                 205

His Asn Gln Cys Ala Ala Gly Cys Thr Gly Pro Arg Glu Ser Asp Cys
    210                 215                 220

Leu Val Cys Arg Lys Phe Arg Asp Glu Ala Thr Cys Lys Asp Thr Cys
225                 230                 235                 240

Pro Pro Leu Met Leu Tyr Asn Pro Thr Thr Tyr Gln Met Asp Val Asn
                245                 250                 255

Pro Glu Gly Lys Tyr Ser Phe Gly Ala Thr Cys Val Lys Lys Cys Pro
            260                 265                 270

Arg Asn Tyr Val Val Thr Asp His Gly Ser Cys Val Arg Ala Cys Gly
            275                 280                 285

Ala Asp Ser Tyr Glu Met Glu Glu Asp Gly Val Arg Lys Cys Lys Lys
    290                 295                 300

Cys Glu Gly Pro Cys Arg Lys Val Cys Asn Gly Ile Gly Ile Gly Glu
305                 310                 315                 320

Phe Lys Asp Ser Leu Ser Ile Asn Ala Thr Asn Ile Lys His Phe Lys
                325                 330                 335

Asn Cys Thr Ser Ile Ser Gly Asp Leu His Ile Leu Pro Val Ala Phe
            340                 345                 350

Arg Gly Asp Ser Phe Thr His Thr Pro Pro Leu Asp Pro Gln Glu Leu
            355                 360                 365

Asp Ile Leu Lys Thr Val Lys Glu Ile Thr Gly Phe Leu Leu Ile Gln
    370                 375                 380

Ala Trp Pro Glu Asn Arg Thr Asp Leu His Ala Phe Glu Asn Leu Glu
385                 390                 395                 400

Ile Ile Arg Gly Arg Thr Lys Gln His Gly Gln Phe Ser Leu Ala Val
```

-continued

```
              405              410              415

Val Ser Leu Asn Ile Thr Ser Leu Gly Leu Arg Ser Leu Lys Glu Ile
        420              425              430

Ser Asp Gly Asp Val Ile Ile Ser Gly Asn Lys Asn Leu Cys Tyr Ala
        435              440              445

Asn Thr Ile Asn Trp Lys Lys Leu Phe Gly Thr Ser Gly Gln Lys Thr
    450              455              460

Lys Ile Ile Ser Asn Arg Gly Glu Asn Ser Cys Lys Ala Thr Gly Gln
465              470              475              480

Val Cys His Ala Leu Cys Ser Pro Glu Gly Cys Trp Gly Pro Glu Pro
            485              490              495

Arg Asp Cys Val Ser Cys Arg Asn Val Ser Arg Gly Arg Glu Cys Val
            500              505              510

Asp Lys Cys Asn Leu Leu Glu Gly Glu Pro Arg Glu Phe Val Glu Asn
        515              520              525

Ser Glu Cys Ile Gln Cys His Pro Glu Cys Leu Pro Gln Ala Met Asn
        530              535              540

Ile Thr Cys Thr Gly Arg Gly Pro Asp Asn Cys Ile Gln Cys Ala His
545              550              555              560

Tyr Ile Asp Gly Pro His Cys Val Lys Thr Cys Pro Ala Gly Val Met
            565              570              575

Gly Glu Asn Asn Thr Leu Val Trp Lys Tyr Ala Asp Ala Gly His Val
            580              585              590

Cys His Leu Cys His Pro Asn Cys Thr Tyr Gly Cys Thr Gly Pro Gly
        595              600              605

Leu Glu Gly Cys Pro Thr Asn Gly Pro Lys Ile Pro Ser
    610              615              620
```

<210> SEQ ID NO 3
<211> LENGTH: 996
<212> TYPE: DNA
<213> ORGANISM: Artificial Sequence
<220> FEATURE:
<223> OTHER INFORMATION: Human EGFRvIII ectodomain cDNA sequence
      (nucleotides 1-996)

<400> SEQUENCE: 3

```
ctggaagaga agaaaggcaa ctacgtcgtg accgaccacg gcagctgtgt gcgggcttgt      60
ggcgccgata gctacgagat ggaagaggac ggcgtgcgga agtgcaagaa gtgcgagggc     120
ccctgccgga aagtgtgcaa cggcatcggc atcggagagt tcaaggacag cctgagcatc     180
aacgccacca acatcaagca cttcaagaac tgcaccagca tcagcggcga cctgcacatc     240
ctgcccgtgg cctttagagg cgacagcttc acccacaccc ccccactgga cccccaggaa     300
ctggacatcc tgaaaaccgt gaaagagatc accggctttc tgctgattca ggcctggccc     360
gagaaccgga cagacctgca cgccttcgag aacctggaaa tcatccgggg caggaccaag     420
cagcacggcc agttttctct ggccgtggtg tccctgaaca tcaccagcct gggcctgcgg     480
agcctgaaag aaatcagcga cggcgacgtg atcatctccg gcaacaagaa cctgtgctac     540
gccaacacca tcaactggaa gaagctgttc ggcacctccg gccagaaaac aaagatcatc     600
agcaaccggg gcgagaacag ctgcaaggcc acaggacaag tgtgccacgc cctgtgtagc     660
cctgagggct gttggggacc cgagcccaga gattgcgtgt cctgcagaaa cgtgtcccgg     720
ggcagagaat gcgtggacaa gtgcaacctg ctggaaggcg agccccgcga gttcgtggaa     780
aacagcgagt gcatccagtg ccacccccgag tgtctgcccc aggccatgaa cattacctgc     840
```

```
accggcagag gccccgacaa ctgtatccag tgcgcccact acatcgacgg cccccactgc      900
gtgaaaacct gtcctgctgg cgtgatggga gagaacaaca ccctcgtgtg gaagtacgcc      960
gacgccggcc atgtgtgcca cctgtgtcac cccaat                                996
```

```
<210> SEQ ID NO 4
<211> LENGTH: 332
<212> TYPE: PRT
<213> ORGANISM: Artificial Sequence
<220> FEATURE:
<223> OTHER INFORMATION: Human EGFRvIII ectodomain amino acid sequence
      (amino acids 1-332)

<400> SEQUENCE: 4

Leu Glu Glu Lys Lys Gly Asn Tyr Val Val Thr Asp His Gly Ser Cys
1               5                   10                  15

Val Arg Ala Cys Gly Ala Asp Ser Tyr Glu Met Glu Glu Asp Gly Val
            20                  25                  30

Arg Lys Cys Lys Lys Cys Glu Gly Pro Cys Arg Lys Val Cys Asn Gly
        35                  40                  45

Ile Gly Ile Gly Glu Phe Lys Asp Ser Leu Ser Ile Asn Ala Thr Asn
    50                  55                  60

Ile Lys His Phe Lys Asn Cys Thr Ser Ile Ser Gly Asp Leu His Ile
65                  70                  75                  80

Leu Pro Val Ala Phe Arg Gly Asp Ser Phe Thr His Thr Pro Pro Leu
                85                  90                  95

Asp Pro Gln Glu Leu Asp Ile Leu Lys Thr Val Lys Glu Ile Thr Gly
            100                 105                 110

Phe Leu Leu Ile Gln Ala Trp Pro Glu Asn Arg Thr Asp Leu His Ala
        115                 120                 125

Phe Glu Asn Leu Glu Ile Ile Arg Gly Arg Thr Lys Gln His Gly Gln
    130                 135                 140

Phe Ser Leu Ala Val Val Ser Leu Asn Ile Thr Ser Leu Gly Leu Arg
145                 150                 155                 160

Ser Leu Lys Glu Ile Ser Asp Gly Asp Val Ile Ile Ser Gly Asn Lys
                165                 170                 175

Asn Leu Cys Tyr Ala Asn Thr Ile Asn Trp Lys Lys Leu Phe Gly Thr
            180                 185                 190

Ser Gly Gln Lys Thr Lys Ile Ile Ser Asn Arg Gly Glu Asn Ser Cys
        195                 200                 205

Lys Ala Thr Gly Gln Val Cys His Ala Leu Cys Ser Pro Glu Gly Cys
    210                 215                 220

Trp Gly Pro Glu Pro Arg Asp Cys Val Ser Cys Arg Asn Val Ser Arg
225                 230                 235                 240

Gly Arg Glu Cys Val Asp Lys Cys Asn Leu Leu Glu Gly Glu Pro Arg
                245                 250                 255

Glu Phe Val Glu Asn Ser Glu Cys Ile Gln Cys His Pro Glu Cys Leu
            260                 265                 270

Pro Gln Ala Met Asn Ile Thr Cys Thr Gly Arg Gly Pro Asp Asn Cys
        275                 280                 285

Ile Gln Cys Ala His Tyr Ile Asp Gly Pro His Cys Val Lys Thr Cys
    290                 295                 300

Pro Ala Gly Val Met Gly Glu Asn Asn Thr Leu Val Trp Lys Tyr Ala
305                 310                 315                 320

Asp Ala Gly His Val Cys His Leu Cys His Pro Asn
```

```
                        325                  330

<210> SEQ ID NO 5
<211> LENGTH: 23
<212> TYPE: PRT
<213> ORGANISM: Artificial Sequence
<220> FEATURE:
<223> OTHER INFORMATION: Human EGFRvIII amino acid residues 15 to 37

<400> SEQUENCE: 5

Ser Cys Val Arg Ala Cys Gly Ala Asp Ser Tyr Glu Met Glu Glu Asp
1               5                   10                  15

Gly Val Arg Lys Cys Lys Lys
            20

<210> SEQ ID NO 6
<211> LENGTH: 112
<212> TYPE: PRT
<213> ORGANISM: Artificial Sequence
<220> FEATURE:
<223> OTHER INFORMATION: 5B7 light chain variable region

<400> SEQUENCE: 6

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Gln Thr Phe Gly Gly Gly Thr Lys Leu Glu Ile Lys
            100                 105                 110

<210> SEQ ID NO 7
<211> LENGTH: 16
<212> TYPE: PRT
<213> ORGANISM: Artificial Sequence
<220> FEATURE:
<223> OTHER INFORMATION: 5B7 CDRL1

<400> SEQUENCE: 7

Lys Ser Ser Gln Ser Leu Leu Asp Ser Asp Gly Lys Thr Tyr Leu Asn
1               5                   10                  15

<210> SEQ ID NO 8
<211> LENGTH: 7
<212> TYPE: PRT
<213> ORGANISM: Artificial Sequence
<220> FEATURE:
<223> OTHER INFORMATION: 5B7 CDRL2

<400> SEQUENCE: 8

Leu Val Ser Lys Leu Asp Ser
1               5

<210> SEQ ID NO 9
<211> LENGTH: 9
<212> TYPE: PRT
```

```
<213> ORGANISM: Artificial Sequence
<220> FEATURE:
<223> OTHER INFORMATION: 5B7 CDRL3

<400> SEQUENCE: 9

Trp Gln Gly Thr His Phe Pro Gln Thr
1               5

<210> SEQ ID NO 10
<211> LENGTH: 115
<212> TYPE: PRT
<213> ORGANISM: Artificial Sequence
<220> FEATURE:
<223> OTHER INFORMATION: 5B7 heavy chain variable region

<400> SEQUENCE: 10

Gln Ile Gln Leu Val Gln Ser Gly Pro Glu Leu Lys Lys Pro Gly Glu
1               5                   10                  15

Thr Val Met Ile Ser Cys Lys Ala Ser Gly Tyr Ser Phe Thr Asn Tyr
                20                  25                  30

Gly Met Asn Trp Val Lys Gln Ala Pro Glu Lys Asp Leu Lys Trp Met
            35                  40                  45

Gly Trp Ile Asn Thr Tyr Thr Gly Glu Ser Arg Tyr Val Asp Glu Phe
        50                  55                  60

Lys Gly Arg Phe Ala Phe Ser Leu Glu Thr Ser Val Ser Ile Val Tyr
65                  70                  75                  80

Leu Lys Ile Asn Asn Leu Lys Asn Glu Asp Met Ala Thr Tyr Phe Cys
                85                  90                  95

Ala Arg Gly Pro Asn Phe Asp Val Trp Gly Thr Gly Thr Thr Val Thr
            100                 105                 110

Val Ser Ser
        115

<210> SEQ ID NO 11
<211> LENGTH: 5
<212> TYPE: PRT
<213> ORGANISM: Artificial Sequence
<220> FEATURE:
<223> OTHER INFORMATION: 5B7 CDRH1

<400> SEQUENCE: 11

Asn Tyr Gly Met Asn
1               5

<210> SEQ ID NO 12
<211> LENGTH: 17
<212> TYPE: PRT
<213> ORGANISM: Artificial Sequence
<220> FEATURE:
<223> OTHER INFORMATION: 5B7 CDRH2

<400> SEQUENCE: 12

Trp Ile Asn Thr Tyr Thr Gly Glu Ser Arg Tyr Val Asp Glu Phe Lys
1               5                   10                  15

Gly

<210> SEQ ID NO 13
<211> LENGTH: 6
<212> TYPE: PRT
<213> ORGANISM: Artificial Sequence
<220> FEATURE:
<223> OTHER INFORMATION: 5B7 CDRH3
```

<400> SEQUENCE: 13

Gly Pro Asn Phe Asp Val
1               5

<210> SEQ ID NO 14
<211> LENGTH: 108
<212> TYPE: PRT
<213> ORGANISM: Artificial Sequence
<220> FEATURE:
<223> OTHER INFORMATION: 3D12 light chain variable region

<400> SEQUENCE: 14

Glu Ile Val Leu Thr Gln Ser Pro Ala Leu Met Ala Ala Ser Pro Gly
1               5                   10                  15

Glu Lys Val Thr Ile Thr Cys Ser Val Ser Ser Ser Ile Ser Ser Ser
            20                  25                  30

Asn Leu His Trp Tyr Gln Gln Lys Ser Glu Thr Ser Pro Lys Pro Trp
        35                  40                  45

Ile Tyr Gly Thr Ser Asn Leu Ala Ser Gly Val Pro Val Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys Gln Gln Trp Ser Ser Tyr Pro
                85                  90                  95

Leu Thr Phe Gly Ser Gly Thr Lys Leu Glu Ile Lys
            100                 105

<210> SEQ ID NO 15
<211> LENGTH: 12
<212> TYPE: PRT
<213> ORGANISM: Artificial Sequence
<220> FEATURE:
<223> OTHER INFORMATION: 3D12 CDRL1

<400> SEQUENCE: 15

Ser Val Ser Ser Ser Ile Ser Ser Ser Asn Leu His
1               5                   10

<210> SEQ ID NO 16
<211> LENGTH: 7
<212> TYPE: PRT
<213> ORGANISM: Artificial Sequence
<220> FEATURE:
<223> OTHER INFORMATION: 3D12 CDRL2

<400> SEQUENCE: 16

Gly Thr Ser Asn Leu Ala Ser
1               5

<210> SEQ ID NO 17
<211> LENGTH: 9
<212> TYPE: PRT
<213> ORGANISM: Artificial Sequence
<220> FEATURE:
<223> OTHER INFORMATION: 3D12 CDRL3

<400> SEQUENCE: 17

Gln Gln Trp Ser Ser Tyr Pro Leu Thr
1               5

<210> SEQ ID NO 18
<211> LENGTH: 119
<212> TYPE: PRT

<213> ORGANISM: Artificial Sequence
<220> FEATURE:
<223> OTHER INFORMATION: 3D12 heavy chain variable region

<400> SEQUENCE: 18

Glu Val Gln Leu Gln Gln Ser Gly Pro Glu Leu Val Lys Pro Gly Ser
1               5                   10                  15

Ser Val Arg Ile Ser Cys Lys Ala Ser Gly Tyr Thr Phe Thr Asp Tyr
            20                  25                  30

Asn Met Asp Trp Val Lys Gln Ser His Gly Lys Ser Leu Glu Trp Ile
        35                  40                  45

Gly Thr Ile Asn Pro Asn Asn Gly Gly Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Val Arg Gln Leu Gly Leu Trp Phe Ala Tyr Trp Gly Gln Gly
            100                 105                 110

Thr Leu Val Thr Val Ser Ala
        115

<210> SEQ ID NO 19
<211> LENGTH: 5
<212> TYPE: PRT
<213> ORGANISM: Artificial Sequence
<220> FEATURE:
<223> OTHER INFORMATION: 3D12 CDRH1

<400> SEQUENCE: 19

Asp Tyr Asn Met Asp
1               5

<210> SEQ ID NO 20
<211> LENGTH: 17
<212> TYPE: PRT
<213> ORGANISM: Artificial Sequence
<220> FEATURE:
<223> OTHER INFORMATION: 3D12 CDRH2

<400> SEQUENCE: 20

Thr Ile Asn Pro Asn Asn Gly Gly Thr Ser Tyr Asn Gln Lys Phe Lys
1               5                   10                  15

Gly

<210> SEQ ID NO 21
<211> LENGTH: 10
<212> TYPE: PRT
<213> ORGANISM: Artificial Sequence
<220> FEATURE:
<223> OTHER INFORMATION: 3D12 CDRH3

<400> SEQUENCE: 21

Val Arg Gln Leu Gly Leu Trp Phe Ala Tyr
1               5                   10

<210> SEQ ID NO 22
<211> LENGTH: 112
<212> TYPE: PRT
<213> ORGANISM: Artificial Sequence
<220> FEATURE:
<223> OTHER INFORMATION: 1D2 light chain variable region -continued

```
<400> SEQUENCE: 22

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asp Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

<210> SEQ ID NO 23
<211> LENGTH: 16
<212> TYPE: PRT
<213> ORGANISM: Artificial Sequence
<220> FEATURE:
<223> OTHER INFORMATION: 1D2 CDRL1

<400> SEQUENCE: 23

Arg Ser Ser Gln Ser Leu Val His Ser Asp Gly Asn Thr Tyr Leu His
1               5                   10                  15

<210> SEQ ID NO 24
<211> LENGTH: 7
<212> TYPE: PRT
<213> ORGANISM: Artificial Sequence
<220> FEATURE:
<223> OTHER INFORMATION: 1D2 CDRL2

<400> SEQUENCE: 24

Lys Val Ser Asn Arg Phe Ser
1               5

<210> SEQ ID NO 25
<211> LENGTH: 9
<212> TYPE: PRT
<213> ORGANISM: Artificial Sequence
<220> FEATURE:
<223> OTHER INFORMATION: 1D2 CDRL3

<400> SEQUENCE: 25

Ser Gln Ser Thr His Val Pro Trp Thr
1               5

<210> SEQ ID NO 26
<211> LENGTH: 116
<212> TYPE: PRT
<213> ORGANISM: Artificial Sequence
<220> FEATURE:
<223> OTHER INFORMATION: 1D2 heavy chain variable region

<400> SEQUENCE: 26

Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Tyr Ser Trp His Trp Ile Arg Gln Phe Pro Gly Asn Lys Leu Glu Trp
```

-continued

```
             35                    40                    45
Met Gly Tyr Ile His Tyr Ser Gly Ser Thr Asn Tyr Asn Pro Ser Leu
      50                    55                    60

Lys Ser Arg Ile Ser Ile Thr Arg Asp Thr Ser Lys Asn Gln Phe Phe
65                    70                    75                    80

Leu Gln Leu Ser Ser Val Thr Thr Glu Asp Thr Ala Thr Tyr Tyr Cys
                  85                    90                    95

Thr Arg Ser Pro Tyr Phe Asp Val Trp Gly Thr Gly Thr Thr Val Thr
             100                   105                   110

Val Ser Ser Ala
      115
```

```
<210> SEQ ID NO 27
<211> LENGTH: 6
<212> TYPE: PRT
<213> ORGANISM: Artificial Sequence
<220> FEATURE:
<223> OTHER INFORMATION: 1D2 CDRH1

<400> SEQUENCE: 27

Ser Gly Tyr Ser Trp His
1               5
```

```
<210> SEQ ID NO 28
<211> LENGTH: 16
<212> TYPE: PRT
<213> ORGANISM: Artificial Sequence
<220> FEATURE:
<223> OTHER INFORMATION: 1D2 CDRH2

<400> SEQUENCE: 28

Tyr Ile His Tyr Ser Gly Ser Thr Asn Tyr Asn Pro Ser Leu Lys Ser
1               5                   10                  15
```

```
<210> SEQ ID NO 29
<211> LENGTH: 6
<212> TYPE: PRT
<213> ORGANISM: Artificial Sequence
<220> FEATURE:
<223> OTHER INFORMATION: 1D2 CDRH3

<400> SEQUENCE: 29

Ser Pro Tyr Phe Asp Val
1               5
```

```
<210> SEQ ID NO 30
<211> LENGTH: 340
<212> TYPE: PRT
<213> ORGANISM: Artificial Sequence
<220> FEATURE:
<223> OTHER INFORMATION: 5B7 CAR construct amino acid sequence (with
      linker and CD8 hinge)

<400> SEQUENCE: 30

Gln Ile Gln Leu Val Gln Ser Gly Pro Glu Leu Lys Lys Pro Gly Glu
1               5                   10                  15

Thr Val Met Ile Ser Cys Lys Ala Ser Gly Tyr Ser Phe Thr Asn Tyr
             20                    25                    30

Gly Met Asn Trp Val Lys Gln Ala Pro Glu Lys Asp Leu Lys Trp Met
             35                    40                    45

Gly Trp Ile Asn Thr Tyr Thr Gly Glu Ser Arg Tyr Val Asp Glu Phe
      50                    55                    60
```

```
Lys Gly Arg Phe Ala Phe Ser Leu Glu Thr Ser Val Ser Ile Val Tyr
65                  70                  75                  80

Leu Lys Ile Asn Asn Leu Lys Asn Glu Asp Met Ala Thr Tyr Phe Cys
                85                  90                  95

Ala Arg Gly Pro Asn Phe Asp Val Trp Gly Thr Gly Thr Thr Val Thr
                100                 105                 110

Val Ser Ser Ala Lys Thr Thr Ala Pro Ser Val Tyr Pro Leu Ala Pro
                115                 120                 125

Gly Ser Leu Gly Gly Thr Gly Gly Gly Ser Gly Gly Gly Ser Gly
        130                 135                 140

Gly Gly Gly Ser Asp Val Val Met Thr Gln Thr Pro Leu Thr Leu Ser
145                 150                 155                 160

Val Thr Ile Gly Gln Pro Ala Ser Ile Ser Cys Lys Ser Ser Gln Ser
                165                 170                 175

Leu Leu Asp Ser Asp Gly Lys Thr Tyr Leu Asn Trp Leu Leu Gln Arg
                180                 185                 190

Pro Gly Gln Ser Pro Lys Arg Leu Ile Tyr Leu Val Ser Lys Leu Asp
        195                 200                 205

Ser Gly Val Pro Asp Arg Phe Thr Gly Ser Gly Ser Gly Thr Asp Phe
        210                 215                 220

Thr Leu Lys Ile Ser Arg Val Glu Ala Glu Asp Leu Gly Val Tyr Tyr
225                 230                 235                 240

Cys Trp Gln Gly Thr His Phe Pro Gln Thr Phe Gly Gly Gly Thr Lys
                245                 250                 255

Leu Glu Ile Lys Arg Ala Asp Ala Ala Pro Thr Val Ser Ile Phe Pro
                260                 265                 270

Pro Ser Ser Lys Leu Gly Val Ile Ser Asn Ser Val Met Tyr Phe Ser
        275                 280                 285

Ser Val Val Pro Val Leu Gln Lys Val Asn Ser Thr Thr Thr Lys Pro
        290                 295                 300

Val Leu Arg Thr Pro Ser Pro Val His Pro Thr Gly Thr Ser Gln Pro
305                 310                 315                 320

Gln Arg Pro Glu Asp Cys Arg Pro Arg Gly Ser Val Lys Gly Thr Gly
                325                 330                 335

Leu Asp Phe Ala
        340
```

<210> SEQ ID NO 31
<211> LENGTH: 1052
<212> TYPE: DNA
<213> ORGANISM: Artificial Sequence
<220> FEATURE:
<223> OTHER INFORMATION: 5B7 CAR construct nucleotide sequence

<400> SEQUENCE: 31

```
gacagaagac ctaggacaga tccagttggt gcagtctgga cctgagctga agaagcctgg      60
agagacagtc atgatctcct gcaaggcttc tgggtattcc ttcacaaact atggaatgaa     120
ctgggtgaag caggctccag aaaaggattt aaagtggatg ggctggataa acacctacac     180
tggagagtca agatatgttg atgaattcaa gggacggttt gccttctctt tggaaacctc     240
tgttagtatt gtctatttga agatcaacaa cctcaaaaat gaggacatgg ctacatattt     300
ctgtgcaaga gggcctaatt tcgatgtctg gggcacaggg accacggtca ctgtctcctc     360
agccaaaaca acagccccat ccgtctatcc cctggcccct ggaagcttgg gaggtaccgg     420
cggaagtgga ggcggaggat ctggcggcgg aggatccgat gttgtgatga cccagactcc     480
```

-continued

```
actcactttg tcggttacca ttggacaacc agcctccatc tcttgcaagt caagtcagag    540
cctcttagat agtgatggaa agacatattt gaattggttg ttacagaggc caggccagtc    600
tccaaagcgc ctaatctatc tggtgtctaa actggactct ggagtccctg acaggttcac    660
tggcagtgga tcaggacag atttcacact gaaaatcagc agagtggagg ctgaggattt     720
gggagtttat tattgctggc aaggtacaca ttttcctcag acgttcggtg gaggcaccaa    780
gctggaaatc aaacgggctg atgctgcacc aactgtatcc atcttccac catccagtaa      840 gcttggggtc atcagcaact cggtgatgta cttcagttct gtcgtgccag tccttcagaa    900
agtgaactct actactacca agccagtgct gcgaactccc tcacctgtgc accctaccgg    960
gacatctcag ccccaaagac cagaagattg tcggccccgt ggctcagtga aggggaccgg   1020
attggacttc gccccttggg tcttcggtag gg                                  1052
```

<210> SEQ ID NO 32
<211> LENGTH: 548
<212> TYPE: PRT
<213> ORGANISM: Artificial Sequence
<220> FEATURE:
<223> OTHER INFORMATION: 5B7 CAR construct with CD28 intracellular
    transduction domain (ITD) and CD3zeta ITD

<400> SEQUENCE: 32

```
Met Leu Arg Leu Leu Leu Ala Leu Asn Leu Phe Pro Ser Ile Gln Val
1               5                   10                  15

Thr Gly Gln Ile Gln Leu Val Gln Ser Gly Pro Glu Leu Lys Lys Pro
            20                  25                  30

Gly Glu Thr Val Met Ile Ser Cys Lys Ala Ser Gly Tyr Ser Phe Thr
        35                  40                  45

Asn Tyr Gly Met Asn Trp Val Lys Gln Ala Pro Glu Lys Asp Leu Lys
    50                  55                  60

Trp Met Gly Trp Ile Asn Thr Tyr Thr Gly Glu Ser Arg Tyr Val Asp
65                  70                  75                  80

Glu Phe Lys Gly Arg Phe Ala Phe Ser Leu Glu Thr Ser Val Ser Ile
                85                  90                  95

Val Tyr Leu Lys Ile Asn Asn Leu Lys Asn Glu Asp Met Ala Thr Tyr
            100                 105                 110

Phe Cys Ala Arg Gly Pro Asn Phe Asp Val Trp Gly Thr Gly Thr Thr
        115                 120                 125

Val Thr Val Ser Ser Ala Lys Thr Thr Ala Pro Ser Val Tyr Pro Leu
    130                 135                 140

Ala Pro Gly Ser Leu Gly Gly Thr Gly Gly Gly Ser Gly Gly Gly Gly
145                 150                 155                 160

Ser Gly Gly Gly Gly Ser Asp Val Val Met Thr Gln Thr Pro Leu Thr
                165                 170                 175

Leu Ser Val Thr Ile Gly Gln Pro Ala Ser Ile Ser Cys Lys Ser Ser
            180                 185                 190

Gln Ser Leu Leu Asp Ser Asp Gly Lys Thr Tyr Leu Asn Trp Leu Leu
        195                 200                 205

Gln Arg Pro Gly Gln Ser Pro Lys Arg Leu Ile Tyr Leu Val Ser Lys
    210                 215                 220

Leu Asp Ser Gly Val Pro Asp Arg Phe Thr Gly Ser Gly Ser Gly Thr
225                 230                 235                 240

Asp Phe Thr Leu Lys Ile Ser Arg Val Glu Ala Glu Asp Leu Gly Val
                245                 250                 255
```

-continued

```
Tyr Tyr Cys Trp Gln Gly Thr His Phe Pro Gln Thr Phe Gly Gly Gly
        260                 265                 270

Thr Lys Leu Glu Ile Lys Arg Ala Asp Ala Ala Pro Thr Val Ser Ile
        275                 280                 285

Phe Pro Pro Ser Ser Lys Leu Gly Val Ile Ser Asn Ser Val Met Tyr
        290                 295                 300

Phe Ser Ser Val Val Pro Val Leu Gln Lys Val Asn Ser Thr Thr Thr
305                 310                 315                 320

Lys Pro Val Leu Arg Thr Pro Ser Pro Val His Pro Thr Gly Thr Ser
                325                 330                 335

Gln Pro Gln Arg Pro Glu Asp Cys Arg Pro Arg Gly Ser Val Lys Gly
                340                 345                 350

Thr Gly Leu Asp Phe Ala Pro Ser Lys Pro Phe Trp Val Leu Val Val
                355                 360                 365

Val Gly Gly Val Leu Ala Cys Tyr Ser Leu Leu Val Thr Val Ala Phe
        370                 375                 380

Ile Ile Phe Trp Val Arg Ser Lys Arg Ser Arg Leu Leu His Ser Asp
385                 390                 395                 400

Tyr Met Asn Met Thr Pro Arg Arg Pro Gly Pro Thr Arg Lys His Tyr
                405                 410                 415

Gln Pro Tyr Ala Pro Pro Arg Asp Phe Ala Ala Tyr Arg Ser Ala Ser
                420                 425                 430

Leu Arg Val Lys Phe Ser Arg Ser Ala Asp Ala Pro Ala Tyr Gln Gln
        435                 440                 445

Gly Gln Asn Gln Leu Tyr Asn Glu Leu Asn Leu Gly Arg Arg Glu Glu
        450                 455                 460

Tyr Asp Val Leu Asp Lys Arg Arg Gly Arg Asp Pro Glu Met Gly Gly
465                 470                 475                 480

Lys Pro Gln Arg Arg Lys Asn Pro Gln Glu Gly Leu Tyr Asn Glu Leu
                485                 490                 495

Gln Lys Asp Lys Met Ala Glu Ala Tyr Ser Glu Ile Gly Met Lys Gly
                500                 505                 510

Glu Arg Arg Arg Gly Lys Gly His Asp Gly Leu Tyr Gln Gly Leu Ser
                515                 520                 525

Thr Ala Thr Lys Asp Thr Tyr Asp Ala Leu His Met Gln Ala Leu Pro
        530                 535                 540

Pro Arg Leu Glu
545
```

```
<210> SEQ ID NO 33
<211> LENGTH: 340
<212> TYPE: PRT
<213> ORGANISM: Artificial Sequence
<220> FEATURE:
<223> OTHER INFORMATION: 3D12 CAR construct amino acid sequence (with
      linker and CD8 hinge)

<400> SEQUENCE: 33
```

```
Glu Val Gln Leu Gln Gln Ser Gly Pro Glu Leu Val Lys Pro Gly Ser
1               5                   10                  15

Ser Val Arg Ile Ser Cys Lys Ala Ser Gly Tyr Thr Phe Thr Asp Tyr
                20                  25                  30

Asn Met Asp Trp Val Lys Gln Ser His Gly Lys Ser Leu Glu Trp Ile
        35                  40                  45

Gly Thr Ile Asn Pro Asn Asn Gly Gly Thr Ser Tyr Asn Gln Lys Phe
```

```
        50                    55                    60

Lys Gly Lys Ala Thr Leu Thr Val Asp Lys Ser Ser Ser Thr Ala Tyr
65                    70                    75                    80

Met Glu Leu Arg Ser Leu Thr Ser Glu Asp Ser Ala Val Tyr Tyr Cys
                    85                    90                    95

Ala Arg Val Arg Gln Leu Gly Leu Trp Phe Ala Tyr Trp Gly Gln Gly
                100                   105                   110

Thr Leu Val Thr Val Ser Ala Ala Lys Thr Thr Pro Pro Ser Val Tyr
                115                   120                   125

Pro Leu Ala Pro Gly Ser Leu Gly Gly Thr Gly Gly Gly Ser Gly Gly
        130                   135                   140

Gly Gly Ser Gly Gly Gly Gly Ser Glu Ile Val Leu Thr Gln Ser Pro
145                   150                   155                   160

Ala Leu Met Ala Ala Ser Pro Gly Glu Lys Val Thr Ile Thr Cys Ser
                165                   170                   175

Val Ser Ser Ser Ile Ser Ser Ser Asn Leu His Trp Tyr Gln Gln Lys
                180                   185                   190

Ser Glu Thr Ser Pro Lys Pro Trp Ile Tyr Gly Thr Ser Asn Leu Ala
                195                   200                   205

Ser Gly Val Pro Val Arg Phe Ser Gly Ser Gly Ser Gly Thr Ser Tyr
        210                   215                   220

Ser Leu Thr Ile Ser Ser Met Glu Ala Glu Asp Ala Ala Thr Tyr Tyr
225                   230                   235                   240

Cys Gln Gln Trp Ser Ser Tyr Pro Leu Thr Phe Gly Ser Gly Thr Lys
                245                   250                   255

Leu Glu Ile Lys Arg Ala Asp Ala Ala Pro Thr Val Ser Ile Phe Pro
                260                   265                   270

Pro Ser Ser Lys Leu Gly Val Ile Ser Asn Ser Val Met Tyr Phe Ser
                275                   280                   285

Ser Val Val Pro Val Leu Gln Lys Val Asn Ser Thr Thr Thr Lys Pro
        290                   295                   300

Val Leu Arg Thr Pro Ser Pro Val His Pro Thr Gly Thr Ser Gln Pro
305                   310                   315                   320

Gln Arg Pro Glu Asp Cys Arg Pro Arg Gly Ser Val Lys Gly Thr Gly
                325                   330                   335

Leu Asp Phe Ala
            340
```

<210> SEQ ID NO 34
<211> LENGTH: 548
<212> TYPE: PRT
<213> ORGANISM: Artificial Sequence
<220> FEATURE:
<223> OTHER INFORMATION: 3D12 CAR construct with CD28 ITD and CD3zeta
      ITD

<400> SEQUENCE: 34

```
Met Leu Arg Leu Leu Leu Ala Leu Asn Leu Phe Pro Ser Ile Gln Val
1                   5                     10                    15

Thr Gly Glu Val Gln Leu Gln Gln Ser Gly Pro Glu Leu Val Lys Pro
                20                    25                    30

Gly Ser Ser Val Arg Ile Ser Cys Lys Ala Ser Gly Tyr Thr Phe Thr
            35                    40                    45

Asp Tyr Asn Met Asp Trp Val Lys Gln Ser His Gly Lys Ser Leu Glu
        50                    55                    60
```

```
Trp Ile Gly Thr Ile Asn Pro Asn Asn Gly Gly Thr Ser Tyr Asn Gln
65                  70                  75                  80

Lys Phe Lys Gly Lys Ala Thr Leu Thr Val Asp Lys Ser Ser Ser Thr
                    85                  90                  95

Ala Tyr Met Glu Leu Arg Ser Leu Thr Ser Glu Asp Ser Ala Val Tyr
                100                 105                 110

Tyr Cys Ala Arg Val Arg Gln Leu Gly Leu Trp Phe Ala Tyr Trp Gly
            115                 120                 125

Gln Gly Thr Leu Val Thr Val Ser Ala Ala Lys Thr Thr Pro Pro Ser
        130                 135                 140

Val Tyr Pro Leu Ala Pro Gly Ser Leu Gly Gly Thr Gly Gly Gly Ser
145                 150                 155                 160

Gly Gly Gly Gly Ser Gly Gly Gly Ser Glu Ile Val Leu Thr Gln
                165                 170                 175

Ser Pro Ala Leu Met Ala Ala Ser Pro Gly Glu Lys Val Thr Ile Thr
                180                 185                 190

Cys Ser Val Ser Ser Ser Ile Ser Ser Ser Asn Leu His Trp Tyr Gln
            195                 200                 205

Gln Lys Ser Glu Thr Ser Pro Lys Pro Trp Ile Tyr Gly Thr Ser Asn
        210                 215                 220

Leu Ala Ser Gly Val Pro Val Arg Phe Ser Gly Ser Gly Ser Gly Thr
225                 230                 235                 240

Ser Tyr Ser Leu Thr Ile Ser Ser Met Glu Ala Glu Asp Ala Ala Thr
                245                 250                 255

Tyr Tyr Cys Gln Gln Trp Ser Ser Tyr Pro Leu Thr Phe Gly Ser Gly
            260                 265                 270

Thr Lys Leu Glu Ile Lys Arg Ala Asp Ala Ala Pro Thr Val Ser Ile
        275                 280                 285

Phe Pro Pro Ser Ser Lys Leu Gly Val Ile Ser Asn Ser Val Met Tyr
        290                 295                 300

Phe Ser Ser Val Val Pro Val Leu Gln Lys Val Asn Ser Thr Thr Thr
305                 310                 315                 320

Lys Pro Val Leu Arg Thr Pro Ser Pro Val His Pro Thr Gly Thr Ser
                325                 330                 335

Gln Pro Gln Arg Pro Glu Asp Cys Arg Pro Arg Gly Ser Val Lys Gly
            340                 345                 350

Thr Gly Leu Asp Phe Ala Pro Ser Lys Pro Phe Trp Val Leu Val Val
        355                 360                 365

Val Gly Gly Val Leu Ala Cys Tyr Ser Leu Leu Val Thr Val Ala Phe
        370                 375                 380

Ile Ile Phe Trp Val Arg Ser Lys Arg Ser Arg Leu Leu His Ser Asp
385                 390                 395                 400

Tyr Met Asn Met Thr Pro Arg Arg Pro Gly Pro Thr Arg Lys His Tyr
                405                 410                 415

Gln Pro Tyr Ala Pro Pro Arg Asp Phe Ala Ala Tyr Arg Ser Ala Ser
            420                 425                 430

Leu Arg Val Lys Phe Ser Arg Ser Ala Asp Ala Pro Ala Tyr Gln Gln
        435                 440                 445

Gly Gln Asn Gln Leu Tyr Asn Glu Leu Asn Leu Gly Arg Arg Glu Glu
        450                 455                 460

Tyr Asp Val Leu Asp Lys Arg Arg Gly Arg Asp Pro Glu Met Gly Gly
465                 470                 475                 480

Lys Pro Gln Arg Arg Lys Asn Pro Gln Glu Gly Leu Tyr Asn Glu Leu
```

-continued

```
                    485                  490                  495

Gln Lys Asp Lys Met Ala Glu Ala Tyr Ser Glu Ile Gly Met Lys Gly
            500                  505                  510

Glu Arg Arg Arg Gly Lys Gly His Asp Gly Leu Tyr Gln Gly Leu Ser
        515                  520                  525

Thr Ala Thr Lys Asp Thr Tyr Asp Ala Leu His Met Gln Ala Leu Pro
    530                  535                  540

Pro Arg Leu Glu
545

<210> SEQ ID NO 35
<211> LENGTH: 339
<212> TYPE: PRT
<213> ORGANISM: Artificial Sequence
<220> FEATURE:
<223> OTHER INFORMATION: 1D2 CAR construct amino acid sequence (with
      linker and CD8 hinge)

<400> SEQUENCE: 35

Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Tyr Ser Trp His Trp Ile Arg Gln Phe Pro Gly Asn Lys Leu Glu Trp
        35                  40                  45

Met Gly Tyr Ile His Tyr Ser Gly Ser Thr Asn Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Ser Ser Val Thr Thr Glu Asp Thr Ala Thr Tyr Tyr Cys
            85                  90                  95

Thr Arg Ser Pro Tyr Phe Asp Val Trp Gly Thr Gly Thr Thr Val Thr
            100                 105                 110

Val Ser Ser Ala Lys Thr Thr Pro Pro Ser Val Tyr Pro Leu Ala Pro
        115                 120                 125

Gly Ser Leu Gly Thr Gly Gly Ser Gly Gly Gly Gly Ser Gly Gly
        130                 135                 140

Gly Gly Ser Asp Val Val Met Thr Gln Thr Pro Leu Ser Leu Pro Val
145                 150                 155                 160

Ser Leu Gly Asp Gln Ala Ser Ile Ser Cys Arg Ser Ser Gln Ser Leu
            165                 170                 175

Val His Ser Asp Gly Asn Thr Tyr Leu His Trp Tyr Leu Gln Lys Pro
        180                 185                 190

Gly Gln Ser Pro Lys Leu Leu Ile Tyr Lys Val Ser Asn Arg Phe Ser
        195                 200                 205

Gly Val Pro Asp Arg Phe Ser Gly Ser Gly Ser Gly Thr Asp Phe Thr
    210                 215                 220

Leu Lys Ile Ser Arg Val Glu Ala Glu Asp Leu Gly Val Tyr Phe Cys
225                 230                 235                 240

Ser Gln Ser Thr His Val Pro Trp Thr Phe Gly Gly Gly Thr Lys Leu
            245                 250                 255

Glu Ile Lys Arg Ala Asp Ala Ala Pro Thr Val Ser Ile Phe Pro Pro
            260                 265                 270

Ser Ser Lys Leu Gly Val Ile Ser Asn Ser Val Met Tyr Phe Ser Ser
        275                 280                 285
```

-continued

```
Val Val Pro Val Leu Gln Lys Val Asn Ser Thr Thr Thr Lys Pro Val
    290             295             300

Leu Arg Thr Pro Ser Pro Val His Pro Thr Gly Thr Ser Gln Pro Gln
305             310             315             320

Arg Pro Glu Asp Cys Arg Pro Arg Gly Ser Val Lys Gly Thr Gly Leu
            325             330             335

Asp Phe Ala

<210> SEQ ID NO 36
<211> LENGTH: 547
<212> TYPE: PRT
<213> ORGANISM: Artificial Sequence
<220> FEATURE:
<223> OTHER INFORMATION: 1D2 CAR construct with CD28 ITD and CD3zeta ITD

<400> SEQUENCE: 36

Met Leu Arg Leu Leu Leu Ala Leu Asn Leu Phe Pro Ser Ile Gln Val
1               5               10              15

Thr Gly Asp Val Gln Leu Gln Glu Ser Gly Pro Asp Leu Val Lys Pro
            20              25              30

Ser Gln Ser Leu Ser Leu Thr Cys Thr Val Thr Gly Tyr Ser Ile Thr
        35              40              45

Ser Gly Tyr Ser Trp His Trp Ile Arg Gln Phe Pro Gly Asn Lys Leu
    50              55              60

Glu Trp Met Gly Tyr Ile His Tyr Ser Gly Ser Thr Asn Tyr Asn Pro
65              70              75              80

Ser Leu Lys Ser Arg Ile Ser Ile Thr Arg Asp Thr Ser Lys Asn Gln
            85              90              95

Phe Phe Leu Gln Leu Ser Ser Val Thr Thr Glu Asp Thr Ala Thr Tyr
        100             105             110

Tyr Cys Thr Arg Ser Pro Tyr Phe Asp Val Trp Gly Thr Gly Thr Thr
        115             120             125

Val Thr Val Ser Ser Ala Lys Thr Thr Pro Pro Ser Val Tyr Pro Leu
    130             135             140

Ala Pro Gly Ser Leu Gly Thr Gly Gly Gly Ser Gly Gly Gly Gly Ser
145             150             155             160

Gly Gly Gly Gly Ser Asp Val Val Met Thr Gln Thr Pro Leu Ser Leu
            165             170             175

Pro Val Ser Leu Gly Asp Gln Ala Ser Ile Ser Cys Arg Ser Ser Gln
            180             185             190

Ser Leu Val His Ser Asp Gly Asn Thr Tyr Leu His Trp Tyr Leu Gln
        195             200             205

Lys Pro Gly Gln Ser Pro Lys Leu Leu Ile Tyr Lys Val Ser Asn Arg
    210             215             220

Phe Ser Gly Val Pro Asp Arg Phe Ser Gly Ser Gly Ser Gly Thr Asp
225             230             235             240

Phe Thr Leu Lys Ile Ser Arg Val Glu Ala Glu Asp Leu Gly Val Tyr
            245             250             255

Phe Cys Ser Gln Ser Thr His Val Pro Trp Thr Phe Gly Gly Gly Thr
            260             265             270

Lys Leu Glu Ile Lys Arg Ala Asp Ala Ala Pro Thr Val Ser Ile Phe
        275             280             285

Pro Pro Ser Ser Lys Leu Gly Val Ile Ser Asn Ser Val Met Tyr Phe
    290             295             300

Ser Ser Val Val Pro Val Leu Gln Lys Val Asn Ser Thr Thr Thr Lys
```

```
305                310                315                320

Pro Val Leu Arg Thr Pro Ser Pro Val His Pro Thr Gly Thr Ser Gln
                325                330                335

Pro Gln Arg Pro Glu Asp Cys Arg Pro Arg Gly Ser Val Lys Gly Thr
                340                345                350

Gly Leu Asp Phe Ala Pro Ser Lys Pro Phe Trp Val Leu Val Val Val
                355                360                365

Gly Gly Val Leu Ala Cys Tyr Ser Leu Leu Val Thr Val Ala Phe Ile
        370                375                380

Ile Phe Trp Val Arg Ser Lys Arg Ser Arg Leu Leu His Ser Asp Tyr
385                390                395                400

Met Asn Met Thr Pro Arg Arg Pro Gly Pro Thr Arg Lys His Tyr Gln
                405                410                415

Pro Tyr Ala Pro Pro Arg Asp Phe Ala Ala Tyr Arg Ser Ala Ser Leu
                420                425                430

Arg Val Lys Phe Ser Arg Ser Ala Asp Ala Pro Ala Tyr Gln Gln Gly
                435                440                445

Gln Asn Gln Leu Tyr Asn Glu Leu Asn Leu Gly Arg Arg Glu Glu Tyr
        450                455                460

Asp Val Leu Asp Lys Arg Arg Gly Arg Asp Pro Glu Met Gly Gly Lys
465                470                475                480

Pro Gln Arg Arg Lys Asn Pro Gln Glu Gly Leu Tyr Asn Glu Leu Gln
                485                490                495

Lys Asp Lys Met Ala Glu Ala Tyr Ser Glu Ile Gly Met Lys Gly Glu
                500                505                510

Arg Arg Arg Gly Lys Gly His Asp Gly Leu Tyr Gln Gly Leu Ser Thr
                515                520                525

Ala Thr Lys Asp Thr Tyr Asp Ala Leu His Met Gln Ala Leu Pro Pro
        530                535                540

Arg Leu Glu
545
```

<210> SEQ ID NO 37
<211> LENGTH: 642
<212> TYPE: DNA
<213> ORGANISM: Artificial Sequence
<220> FEATURE:
<223> OTHER INFORMATION: DNA sequence for modular CAR vector (without
      filler/insert)

<400> SEQUENCE: 37

```
atgctcaggc tgctcttggc tctcaactta ttcccttcaa ttcaagtaac aggagggtct     60
tcgagaagac ctccttctaa gcccttttgg gtgctggtgg tggttggtgg agtcctggct    120
tgctatagct tgctagtaac agtggccttt attattttct gggtgaggag taagaggagc    180
aggctcctgc acagtgacta catgaacatg actcccaggc ggcccggacc cacccgcaag    240
cattaccagc cctatgcccc accacgcgac ttcgcagcct atcgctccgc tagcctgaga    300
gtgaagttca gcaggagcgc agacgccccc gcgtaccagc agggccagaa ccagctctat    360
aacgagctca atctaggacg aagagaggag tacgatgttt tggacaagag acgtggccgg    420
gaccctgaga tggggggaaa gccgcagaga aggaagaacc ctcaggaagg cctgtacaat    480
gaactgcaga agataagat ggcggaggcc tacagtgaga ttgggatgaa aggcgagcgc    540 cggagggggca aggggcacga tggcctttac cagggtctca gtacagccac caaggacacc    600
tacgacgccc ttcacatgca ggccctgccc cctcgcctcg ag                       642
```

-continued

```
<210> SEQ ID NO 38
<211> LENGTH: 345
<212> TYPE: DNA
<213> ORGANISM: Artificial Sequence
<220> FEATURE:
<223> OTHER INFORMATION: 5B7 Heavy chain variable region nucleotide
      sequence

<400> SEQUENCE: 38
cagatccagt tggtgcagtc tggacctgag ctgaagaagc ctggagagac agtcatgatc      60
tcctgcaagg cttctgggta ttccttcaca aactatggaa tgaactgggt gaagcaggct     120
ccagaaaagg atttaaagtg gatgggctgg ataaacacct acactggaga gtcaagatat     180
gttgatgaat tcaagggacg gtttgccttc tctttggaaa cctctgttag tattgtctat     240
ttgaagatca acaacctcaa aaatgaggac atggctacat atttctgtgc aagagggcct     300
aatttcgatg tctggggcac agggaccacg gtcaccgtct cctca                      345

<210> SEQ ID NO 39
<211> LENGTH: 336
<212> TYPE: DNA
<213> ORGANISM: Artificial Sequence
<220> FEATURE:
<223> OTHER INFORMATION: 5B7 Light chain variable region nucleotide
      sequence

<400> SEQUENCE: 39
gatgttgtga tgacccagac tccactcact ttgtcggtta ccattggaca accagcctcc      60
atctcttgca agtcaagtca gagcctctta gatagtgatg gaaagacata tttgaattgg     120
ttgttacaga ggccaggcca gtctccaaag cgcctaatct atctggtgtc taaactggac     180
tctggagtcc ctgacaggtt cactggcagt ggatcaggga cagatttcac actgaaaatc     240
agcagagtgg aggctgagga tttgggagtt tattattgct ggcaaggtac acattttcct     300
cagacgttcg gtggaggcac caagctggaa atcaaa                                336

<210> SEQ ID NO 40
<211> LENGTH: 357
<212> TYPE: DNA
<213> ORGANISM: Artificial Sequence
<220> FEATURE:
<223> OTHER INFORMATION: 3D12 Heavy chain variable region nucleotide
      sequence

<400> SEQUENCE: 40
gaggtccagc tgcaacagtc tggacctgag ctggtgaagc ctgggtcttc agtgaggata      60
tcctgcaaag cttctggata cacattcact gactacaaca tggactgggt gaagcagagc     120
catggaaaga gccttgagtg gattggaact attaatccta caatggtgg tactagctac     180 aaccagaagt tcaagggcaa ggccacattg actgttgaca gtcctccag cacagcctac     240 atggaactcc gcagcctgac atctgaggac tctgcagtct attactgtgc aagagtgaga     300
cagctcgggc tgtggtttgc ttactggggc caagggactc tggtcactgt ctctgca         357

<210> SEQ ID NO 41
<211> LENGTH: 324
<212> TYPE: DNA
<213> ORGANISM: Artificial Sequence
<220> FEATURE:
<223> OTHER INFORMATION: 3D12 Light chain variable region nucleotide
      sequence
```

-continued

```
<400> SEQUENCE: 41
gaaattgtgc tcacccagtc tccagcactc atggctgcat ctccagggga gaaggtcacc      60
atcacctgca gtgtcagctc aagtataagt tccagcaact tgcactggta ccagcagaag     120
tcagaaacct cccccaaacc ctggatttat ggcacatcca acctggcttc tggagtccct     180
gttcgcttca gtggcagtgg atctgggacc tcttattctc tcacaatcag cagcatggag     240
gctgaagatg ctgccactta ttactgtcaa cagtggagta gttacccact cacgttcggc     300
tcggggacaa agttggaaat aaaa                                            324

<210> SEQ ID NO 42
<211> LENGTH: 345
<212> TYPE: DNA
<213> ORGANISM: Artificial Sequence
<220> FEATURE:
<223> OTHER INFORMATION: 1D2 Heavy chain variable nucleotide sequence

<400> SEQUENCE: 42
gatgtgcagc ttcaggagtc aggacctgac ctggtgaaac cttctcagtc actttcactc      60
acctgcactg tcactggcta ctccatcacc agtggttata ctggcactg gatccggcag     120 tttccaggaa acaaactgga atggatgggc tacatacact acagtggtag cactaactac     180
aacccatctc tcaaaagtcg aatctctatc actcgagaca catccaagaa ccagttcttc     240
ctgcagttga ttctgtgac tactgaggac actgccacat attactgtac aagaagcccg     300
tacttcgatg tctggggcac agggaccacg gtcaccgtct cctca                      345

<210> SEQ ID NO 43
<211> LENGTH: 336
<212> TYPE: DNA
<213> ORGANISM: Artificial Sequence
<220> FEATURE:
<223> OTHER INFORMATION: 1D2 Light chain variable region nucleotide
      sequence

<400> SEQUENCE: 43
gatgttgtga tgacccaaac tccactctcc ctgcctgtca gtcttggcga tcaagcctcc      60
atctcttgca gatctagtca gagccttgtg cacagtgatg gaaacaccta tttacattgg     120
tacctgcaga agccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggagtt tatttctgct ctcaaagtac acatgttccg     300
tggacgttcg gtggaggcac caagctggaa atcaaa                               336

<210> SEQ ID NO 44
<211> LENGTH: 278
<212> TYPE: PRT
<213> ORGANISM: Artificial Sequence
<220> FEATURE:
<223> OTHER INFORMATION: 5B7 scFV

<400> SEQUENCE: 44

Gln Ile Gln Leu Val Gln Ser Gly Pro Glu Leu Lys Lys Pro Gly Glu
1               5                   10                  15

Thr Val Met Ile Ser Cys Lys Ala Ser Gly Tyr Ser Phe Thr Asn Tyr
            20                  25                  30

Gly Met Asn Trp Val Lys Gln Ala Pro Glu Lys Asp Leu Lys Trp Met
        35                  40                  45

Gly Trp Ile Asn Thr Tyr Thr Gly Glu Ser Arg Tyr Val Asp Glu Phe
```

-continued

```
            50               55                60

Lys Gly Arg Phe Ala Phe Ser Leu Glu Thr Ser Val Ser Ile Val Tyr
65                  70                75                  80

Leu Lys Ile Asn Asn Leu Lys Asn Glu Asp Met Ala Thr Tyr Phe Cys
                85                90                95

Ala Arg Gly Pro Asn Phe Asp Val Trp Gly Thr Gly Thr Thr Val Thr
                100               105               110

Val Ser Ser Ala Lys Thr Thr Ala Pro Ser Val Tyr Pro Leu Ala Pro
                115               120               125

Gly Ser Leu Gly Gly Thr Gly Gly Ser Gly Gly Gly Ser Gly
        130               135               140

Gly Gly Gly Ser Asp Val Val Met Thr Gln Thr Pro Leu Thr Leu Ser
145               150               155               160

Val Thr Ile Gly Gln Pro Ala Ser Ile Ser Cys Lys Ser Ser Gln Ser
                165               170               175

Leu Leu Asp Ser Asp Gly Lys Thr Tyr Leu Asn Trp Leu Leu Gln Arg
                180               185               190

Pro Gly Gln Ser Pro Lys Arg Leu Ile Tyr Leu Val Ser Lys Leu Asp
                195               200               205

Ser Gly Val Pro Asp Arg Phe Thr Gly Ser Gly Ser Gly Thr Asp Phe
        210               215               220

Thr Leu Lys Ile Ser Arg Val Glu Ala Glu Asp Leu Gly Val Tyr Tyr
225               230               235               240

Cys Trp Gln Gly Thr His Phe Pro Gln Thr Phe Gly Gly Gly Thr Lys
                245               250               255

Leu Glu Ile Lys Arg Ala Asp Ala Ala Pro Thr Val Ser Ile Phe Pro
                260               265               270

Pro Ser Ser Lys Leu Gly
                275

<210> SEQ ID NO 45
<211> LENGTH: 278
<212> TYPE: PRT
<213> ORGANISM: Artificial Sequence
<220> FEATURE:
<223> OTHER INFORMATION: 3D12 scFV

<400> SEQUENCE: 45

Glu Val Gln Leu Gln Gln Ser Gly Pro Glu Leu Val Lys Pro Gly Ser
1               5               10                15

Ser Val Arg Ile Ser Cys Lys Ala Ser Gly Tyr Thr Phe Thr Asp Tyr
                20                25                30

Asn Met Asp Trp Val Lys Gln Ser His Gly Lys Ser Leu Glu Trp Ile
                35                40                45

Gly Thr Ile Asn Pro Asn Asn Gly Gly Thr Ser Tyr Asn Gln Lys Phe
        50                55                60

Lys Gly Lys Ala Thr Leu Thr Val Asp Lys Ser Ser Ser Thr Ala Tyr
65                  70                75                  80

Met Glu Leu Arg Ser Leu Thr Ser Glu Asp Ser Ala Val Tyr Tyr Cys
                85                90                95

Ala Arg Val Arg Gln Leu Gly Leu Trp Phe Ala Tyr Trp Gly Gln Gly
                100               105               110

Thr Leu Val Thr Val Ser Ala Ala Lys Thr Thr Pro Pro Ser Val Tyr
                115               120               125

Pro Leu Ala Pro Gly Ser Leu Gly Gly Thr Gly Gly Gly Ser Gly Gly
```

-continued

```
              130               135               140
Gly Gly Ser Gly Gly Gly Gly Ser Glu Ile Val Leu Thr Gln Ser Pro
145               150               155               160

Ala Leu Met Ala Ala Ser Pro Gly Glu Lys Val Thr Ile Thr Cys Ser
                165               170               175

Val Ser Ser Ser Ile Ser Ser Ser Asn Leu His Trp Tyr Gln Gln Lys
            180               185               190

Ser Glu Thr Ser Pro Lys Pro Trp Ile Tyr Gly Thr Ser Asn Leu Ala
            195               200               205

Ser Gly Val Pro Val Arg Phe Ser Gly Ser Gly Ser Gly Thr Ser Tyr
        210               215               220

Ser Leu Thr Ile Ser Ser Met Glu Ala Glu Asp Ala Ala Thr Tyr Tyr
225               230               235               240

Cys Gln Gln Trp Ser Ser Tyr Pro Leu Thr Phe Gly Ser Gly Thr Lys
                245               250               255

Leu Glu Ile Lys Arg Ala Asp Ala Ala Pro Thr Val Ser Ile Phe Pro
            260               265               270

Pro Ser Ser Lys Leu Gly
            275

<210> SEQ ID NO 46
<211> LENGTH: 277
<212> TYPE: PRT
<213> ORGANISM: Artificial Sequence
<220> FEATURE:
<223> OTHER INFORMATION: 1D2 scFV

<400> SEQUENCE: 46

Asp Val Gln Leu Gln Glu Ser Gly Pro Asp Leu Val Lys Pro Ser Gln
1               5               10               15

Ser Leu Ser Leu Thr Cys Thr Val Thr Gly Tyr Ser Ile Thr Ser Gly
            20               25               30

Tyr Ser Trp His Trp Ile Arg Gln Phe Pro Gly Asn Lys Leu Glu Trp
            35               40               45

Met Gly Tyr Ile His Tyr Ser Gly Ser Thr Asn Tyr Asn Pro Ser Leu
        50               55               60

Lys Ser Arg Ile Ser Ile Thr Arg Asp Thr Ser Lys Asn Gln Phe Phe
65               70               75               80

Leu Gln Leu Ser Ser Val Thr Thr Glu Asp Thr Ala Thr Tyr Tyr Cys
            85               90               95

Thr Arg Ser Pro Tyr Phe Asp Val Trp Gly Thr Gly Thr Thr Val Thr
            100               105               110

Val Ser Ser Ala Lys Thr Thr Pro Pro Ser Val Tyr Pro Leu Ala Pro
        115               120               125

Gly Ser Leu Gly Thr Gly Gly Gly Ser Gly Gly Gly Ser Gly Gly
            130               135               140

Gly Gly Ser Asp Val Val Met Thr Gln Thr Pro Leu Ser Leu Pro Val
145               150               155               160

Ser Leu Gly Asp Gln Ala Ser Ile Ser Cys Arg Ser Ser Gln Ser Leu
                165               170               175

Val His Ser Asp Gly Asn Thr Tyr Leu His Trp Tyr Leu Gln Lys Pro
            180               185               190

Gly Gln Ser Pro Lys Leu Leu Ile Tyr Lys Val Ser Asn Arg Phe Ser
            195               200               205

Gly Val Pro Asp Arg Phe Ser Gly Ser Gly Ser Gly Thr Asp Phe Thr
```

-continued

```
        210                 215                 220
Leu Lys Ile Ser Arg Val Glu Ala Glu Asp Leu Gly Val Tyr Phe Cys
225                 230                 235                 240

Ser Gln Ser Thr His Val Pro Trp Thr Phe Gly Gly Gly Thr Lys Leu
                245                 250                 255

Glu Ile Lys Arg Ala Asp Ala Ala Pro Thr Val Ser Ile Phe Pro Pro
            260                 265                 270

Ser Ser Lys Leu Gly
        275

<210> SEQ ID NO 47
<211> LENGTH: 14
<212> TYPE: PRT
<213> ORGANISM: Artificial Sequence
<220> FEATURE:
<223> OTHER INFORMATION: Linker

<400> SEQUENCE: 47

Gly Gly Gly Ser Gly Gly Gly Gly Ser Gly Gly Gly Gly Ser
1               5                   10

<210> SEQ ID NO 48
<211> LENGTH: 23
<212> TYPE: PRT
<213> ORGANISM: Artificial Sequence
<220> FEATURE:
<223> OTHER INFORMATION: Amino acid residues 15 to 37 of EGFRvIII, with
      Ser15 to Ala mutation

<400> SEQUENCE: 48

Ala Cys Val Arg Ala Cys Gly Ala Asp Ser Tyr Glu Met Glu Glu Asp
1               5                   10                  15

Gly Val Arg Lys Cys Lys Lys
            20

<210> SEQ ID NO 49
<211> LENGTH: 23
<212> TYPE: PRT
<213> ORGANISM: Artificial Sequence
<220> FEATURE:
<223> OTHER INFORMATION: Amino acid residues 15 to 37 of EGFRvIII, with
      Cys16 to Ala mutation

<400> SEQUENCE: 49

Ser Ala Val Arg Ala Cys Gly Ala Asp Ser Tyr Glu Met Glu Glu Asp
1               5                   10                  15

Gly Val Arg Lys Cys Lys Lys
            20

<210> SEQ ID NO 50
<211> LENGTH: 23
<212> TYPE: PRT
<213> ORGANISM: Artificial Sequence
<220> FEATURE:
<223> OTHER INFORMATION: Amino acid residues 15 to 37 of EGFRvIII, with
      Val17 to Ala mutation

<400> SEQUENCE: 50

Ser Cys Ala Arg Ala Cys Gly Ala Asp Ser Tyr Glu Met Glu Glu Asp
1               5                   10                  15

Gly Val Arg Lys Cys Lys Lys
            20
```

```
<210> SEQ ID NO 51
<211> LENGTH: 23
<212> TYPE: PRT
<213> ORGANISM: Artificial Sequence
<220> FEATURE:
<223> OTHER INFORMATION: Amino acid residues 15 to 37 of EGFRvIII, with
      Arg18 to Ala mutation

<400> SEQUENCE: 51

Ser Cys Val Ala Ala Cys Gly Ala Asp Ser Tyr Glu Met Glu Glu Asp
1               5                   10                  15

Gly Val Arg Lys Cys Lys Lys
            20

<210> SEQ ID NO 52
<211> LENGTH: 23
<212> TYPE: PRT
<213> ORGANISM: Artificial Sequence
<220> FEATURE:
<223> OTHER INFORMATION: Amino acid residues 15 to 37 of EGFRvIII, with
      Cys20 to Ala mutation

<400> SEQUENCE: 52

Ser Cys Val Arg Ala Ala Gly Ala Asp Ser Tyr Glu Met Glu Glu Asp
1               5                   10                  15

Gly Val Arg Lys Cys Lys Lys
            20

<210> SEQ ID NO 53
<211> LENGTH: 23
<212> TYPE: PRT
<213> ORGANISM: Artificial Sequence
<220> FEATURE:
<223> OTHER INFORMATION: Amino acid residues 15 to 37 of EGFRvIII, with
      Gly21 to Ala mutation

<400> SEQUENCE: 53

Ser Cys Val Arg Ala Cys Ala Ala Asp Ser Tyr Glu Met Glu Glu Asp
1               5                   10                  15

Gly Val Arg Lys Cys Lys Lys
            20

<210> SEQ ID NO 54
<211> LENGTH: 23
<212> TYPE: PRT
<213> ORGANISM: Artificial Sequence
<220> FEATURE:
<223> OTHER INFORMATION: Amino acid residues 15 to 37 of EGFRvIII, with
      Asp23 to Ala mutation

<400> SEQUENCE: 54

Ser Cys Val Arg Ala Cys Gly Ala Ala Ser Tyr Glu Met Glu Glu Asp
1               5                   10                  15

Gly Val Arg Lys Cys Lys Lys
            20

<210> SEQ ID NO 55
<211> LENGTH: 23
<212> TYPE: PRT
<213> ORGANISM: Artificial Sequence
<220> FEATURE:
<223> OTHER INFORMATION: Amino acid residues 15 to 37 of EGFRvIII, with
      Ser24 to Ala mutation

<400> SEQUENCE: 55

Ser Cys Val Arg Ala Cys Gly Ala Asp Ala Tyr Glu Met Glu Glu Asp
```

-continued

```
1               5                    10                   15

Gly Val Arg Lys Cys Lys Lys
            20

<210> SEQ ID NO 56
<211> LENGTH: 23
<212> TYPE: PRT
<213> ORGANISM: Artificial Sequence
<220> FEATURE:
<223> OTHER INFORMATION: Amino acid residues 15 to 37 of EGFRvIII, with
      Tyr25 to Ala mutation

<400> SEQUENCE: 56

Ser Cys Val Arg Ala Cys Gly Ala Asp Ser Ala Glu Met Glu Glu Asp
1               5                    10                   15

Gly Val Arg Lys Cys Lys Lys
            20

<210> SEQ ID NO 57
<211> LENGTH: 23
<212> TYPE: PRT
<213> ORGANISM: Artificial Sequence
<220> FEATURE:
<223> OTHER INFORMATION: Amino acid residues 15 to 37 of EGFRvIII, with
      Glu26 to Ala mutation

<400> SEQUENCE: 57

Ser Cys Val Arg Ala Cys Gly Ala Asp Ser Tyr Ala Met Glu Glu Asp
1               5                    10                   15

Gly Val Arg Lys Cys Lys Lys
            20

<210> SEQ ID NO 58
<211> LENGTH: 23
<212> TYPE: PRT
<213> ORGANISM: Artificial Sequence
<220> FEATURE:
<223> OTHER INFORMATION: Amino acid residues 15 to 37 of EGFRvIII, with
      Met27 to Ala mutation

<400> SEQUENCE: 58

Ser Cys Val Arg Ala Cys Gly Ala Asp Ser Tyr Glu Ala Glu Glu Asp
1               5                    10                   15

Gly Val Arg Lys Cys Lys Lys
            20

<210> SEQ ID NO 59
<211> LENGTH: 23
<212> TYPE: PRT
<213> ORGANISM: Artificial Sequence
<220> FEATURE:
<223> OTHER INFORMATION: Amino acid residues 15 to 37 of EGFRvIII, with
      Glu28 to Ala mutation

<400> SEQUENCE: 59

Ser Cys Val Arg Ala Cys Gly Ala Asp Ser Tyr Glu Met Ala Glu Asp
1               5                    10                   15

Gly Val Arg Lys Cys Lys Lys
            20

<210> SEQ ID NO 60
<211> LENGTH: 23
<212> TYPE: PRT
<213> ORGANISM: Artificial Sequence
<220> FEATURE:
```

<223> OTHER INFORMATION: Amino acid residues 15 to 37 of EGFRvIII, with
     Glu29 to Ala mutation

<400> SEQUENCE: 60

Ser Cys Val Arg Ala Cys Gly Ala Asp Ser Tyr Glu Met Glu Ala Asp
1               5                   10                  15

Gly Val Arg Lys Cys Lys Lys
            20

<210> SEQ ID NO 61
<211> LENGTH: 23
<212> TYPE: PRT
<213> ORGANISM: Artificial Sequence
<220> FEATURE:
<223> OTHER INFORMATION: Amino acid residues 15 to 37 of EGFRvIII, with
     Asp30 to Ala mutation

<400> SEQUENCE: 61

Ser Cys Val Arg Ala Cys Gly Ala Asp Ser Tyr Glu Met Glu Glu Ala
1               5                   10                  15

Gly Val Arg Lys Cys Lys Lys
            20

<210> SEQ ID NO 62
<211> LENGTH: 23
<212> TYPE: PRT
<213> ORGANISM: Artificial Sequence
<220> FEATURE:
<223> OTHER INFORMATION: Amino acid residues 15 to 37 of EGFRvIII, with
     Gly31 to Ala mutation

<400> SEQUENCE: 62

Ser Cys Val Arg Ala Cys Gly Ala Asp Ser Tyr Glu Met Glu Glu Asp
1               5                   10                  15

Ala Val Arg Lys Cys Lys Lys
            20

<210> SEQ ID NO 63
<211> LENGTH: 23
<212> TYPE: PRT
<213> ORGANISM: Artificial Sequence
<220> FEATURE:
<223> OTHER INFORMATION: Amino acid residues 15 to 37 of EGFRvIII, with
     Val32 to Ala mutation

<400> SEQUENCE: 63

Ser Cys Val Arg Ala Cys Gly Ala Asp Ser Tyr Glu Met Glu Glu Asp
1               5                   10                  15

Gly Ala Arg Lys Cys Lys Lys
            20

<210> SEQ ID NO 64
<211> LENGTH: 23
<212> TYPE: PRT
<213> ORGANISM: Artificial Sequence
<220> FEATURE:
<223> OTHER INFORMATION: Amino acid residues 15 to 37 of EGFRvIII, with
     Arg33 to Ala mutation

<400> SEQUENCE: 64

Ser Cys Val Arg Ala Cys Gly Ala Asp Ser Tyr Glu Met Glu Glu Asp
1               5                   10                  15

Gly Val Ala Lys Cys Lys Lys
            20

<210> SEQ ID NO 65
<211> LENGTH: 23
<212> TYPE: PRT
<213> ORGANISM: Artificial Sequence
<220> FEATURE:
<223> OTHER INFORMATION: Amino acid residues 15 to 37 of EGFRvIII, with
      Lys34 to Ala mutation

<400> SEQUENCE: 65

Ser Cys Val Arg Ala Cys Gly Ala Asp Ser Tyr Glu Met Glu Glu Asp
1               5                   10                  15

Gly Val Arg Ala Cys Lys Lys
            20

<210> SEQ ID NO 66
<211> LENGTH: 23
<212> TYPE: PRT
<213> ORGANISM: Artificial Sequence
<220> FEATURE:
<223> OTHER INFORMATION: Amino acid residues 15 to 37 of EGFRvIII, with
      Cys35 to Ala mutation

<400> SEQUENCE: 66

Ser Cys Val Arg Ala Cys Gly Ala Asp Ser Tyr Glu Met Glu Glu Asp
1               5                   10                  15

Gly Val Arg Lys Ala Lys Lys
            20

<210> SEQ ID NO 67
<211> LENGTH: 23
<212> TYPE: PRT
<213> ORGANISM: Artificial Sequence
<220> FEATURE:
<223> OTHER INFORMATION: Amino acid residues 15 to 37 of EGFRvIII, with
      Lys36 to Ala mutation

<400> SEQUENCE: 67

Ser Cys Val Arg Ala Cys Gly Ala Asp Ser Tyr Glu Met Glu Glu Asp
1               5                   10                  15

Gly Val Arg Lys Cys Ala Lys
            20

<210> SEQ ID NO 68
<211> LENGTH: 23
<212> TYPE: PRT
<213> ORGANISM: Artificial Sequence
<220> FEATURE:
<223> OTHER INFORMATION: Amino acid residues 15 to 37 of EGFRvIII, with
      Lys37 to Ala mutation

<400> SEQUENCE: 68

Ser Cys Val Arg Ala Cys Gly Ala Asp Ser Tyr Glu Met Glu Glu Asp
1               5                   10                  15

Gly Val Arg Lys Cys Lys Ala
            20

<210> SEQ ID NO 69
<211> LENGTH: 76
<212> TYPE: PRT
<213> ORGANISM: Artificial Sequence
<220> FEATURE:
<223> OTHER INFORMATION: Amino acid residues 1 to 76 of EGFRvIII

<400> SEQUENCE: 69

Leu Glu Glu Lys Lys Gly Asn Tyr Val Val Thr Asp His Gly Ser Cys

-continued

```
1               5                    10                   15

Val Arg Ala Cys Gly Ala Asp Ser Tyr Glu Met Glu Glu Asp Gly Val
            20                   25                   30

Arg Lys Cys Lys Lys Cys Glu Gly Pro Cys Arg Lys Val Cys Asn Gly
        35                   40                   45

Ile Gly Ile Gly Glu Phe Lys Asp Ser Leu Ser Ile Asn Ala Thr Asn
    50                   55                   60

Ile Lys His Phe Lys Asn Cys Thr Ser Ile Ser Gly
65                   70                   75
```

<210> SEQ ID NO 70
<211> LENGTH: 35
<212> TYPE: PRT
<213> ORGANISM: Artificial Sequence
<220> FEATURE:
<223> OTHER INFORMATION: Amino acid residues 3 to 37 of EGFRvIII

<400> SEQUENCE: 70

```
Glu Lys Lys Gly Asn Tyr Val Val Thr Asp His Gly Ser Cys Val Arg
1               5                    10                   15

Ala Cys Gly Ala Asp Ser Tyr Glu Met Glu Glu Asp Gly Val Arg Lys
            20                   25                   30

Cys Lys Lys
        35
```

<210> SEQ ID NO 71
<211> LENGTH: 18
<212> TYPE: PRT
<213> ORGANISM: Artificial Sequence
<220> FEATURE:
<223> OTHER INFORMATION: Amino acid residues 1 to 18 of EGFRvIII

<400> SEQUENCE: 71

```
Leu Glu Glu Lys Lys Gly Asn Tyr Val Val Thr Asp His Gly Ser Cys
1               5                    10                   15

Val Arg
```

<210> SEQ ID NO 72
<211> LENGTH: 243
<212> TYPE: PRT
<213> ORGANISM: Artificial Sequence
<220> FEATURE:
<223> OTHER INFORMATION: 5B7 Shorter scFv

<400> SEQUENCE: 72

```
Gln Ile Gln Leu Val Gln Ser Gly Pro Glu Leu Lys Lys Pro Gly Glu
1               5                    10                   15

Thr Val Met Ile Ser Cys Lys Ala Ser Gly Tyr Ser Phe Thr Asn Tyr
            20                   25                   30

Gly Met Asn Trp Val Lys Gln Ala Pro Glu Lys Asp Leu Lys Trp Met
        35                   40                   45

Gly Trp Ile Asn Thr Tyr Thr Gly Glu Ser Arg Tyr Val Asp Glu Phe
    50                   55                   60

Lys Gly Arg Phe Ala Phe Ser Leu Glu Thr Ser Val Ser Ile Val Tyr
65                   70                   75                   80

Leu Lys Ile Asn Asn Leu Lys Asn Glu Asp Met Ala Thr Tyr Phe Cys
                85                   90                   95

Ala Arg Gly Pro Asn Phe Asp Val Trp Gly Thr Gly Thr Thr Val Thr
            100                  105                  110
```

-continued

Val Ser Ser Gly Thr Gly Gly Ser Gly Gly Gly Ser Gly Gly
        115             120             125

Gly Gly Ser Asp Val Val Met Thr Gln Thr Pro Leu Thr Leu Ser Val
    130             135             140

Thr Ile Gly Gln Pro Ala Ser Ile Ser Cys Lys Ser Ser Gln Ser Leu
145             150             155             160

Leu Asp Ser Asp Gly Lys Thr Tyr Leu Asn Trp Leu Leu Gln Arg Pro
            165             170             175

Gly Gln Ser Pro Lys Arg Leu Ile Tyr Leu Val Ser Lys Leu Asp Ser
            180             185             190

Gly Val Pro Asp Arg Phe Thr Gly Ser Gly Ser Gly Thr Asp Phe Thr
            195             200             205

Leu Lys Ile Ser Arg Val Glu Ala Glu Asp Leu Gly Val Tyr Tyr Cys
    210             215             220

Trp Gln Gly Thr His Phe Pro Gln Thr Phe Gly Gly Gly Thr Lys Leu
225             230             235             240

Glu Ile Lys

<210> SEQ ID NO 73
<211> LENGTH: 226
<212> TYPE: PRT
<213> ORGANISM: Artificial Sequence
<220> FEATURE:
<223> OTHER INFORMATION: 5B7 scFv consensus
<220> FEATURE:
<221> NAME/KEY: SITE
<222> LOCATION: (115)..(116)
<223> OTHER INFORMATION: Linker insertion site between residues 115 and
      116

<400> SEQUENCE: 73

Gln Ile Gln Leu Val Gln Ser Gly Pro Glu Leu Lys Lys Pro Gly Glu
1               5               10              15

Thr Val Met Ile Ser Cys Lys Ala Ser Gly Tyr Ser Phe Thr Asn Tyr
            20              25              30

Gly Met Asn Trp Val Lys Gln Ala Pro Glu Lys Asp Leu Lys Trp Met
        35              40              45

Gly Trp Ile Asn Thr Tyr Thr Gly Glu Ser Arg Tyr Val Asp Glu Phe
    50              55              60

Lys Gly Arg Phe Ala Phe Ser Leu Glu Thr Ser Val Ser Ile Val Tyr
65              70              75              80

Leu Lys Ile Asn Asn Leu Lys Asn Glu Asp Met Ala Thr Tyr Phe Cys
            85              90              95

Ala Arg Gly Pro Asn Phe Asp Val Trp Gly Thr Gly Thr Thr Val Thr
            100             105             110

Val Ser Ser Asp Val Val Met Thr Gln Thr Pro Leu Thr Leu Ser Val
            115             120             125

Thr Ile Gly Gln Pro Ala Ser Ile Ser Cys Lys Ser Ser Gln Ser Leu
    130             135             140

Leu Asp Ser Asp Gly Lys Thr Tyr Leu Asn Trp Leu Leu Gln Arg Pro
145             150             155             160

Gly Gln Ser Pro Lys Arg Leu Ile Tyr Leu Val Ser Lys Leu Asp Ser
            165             170             175

Gly Val Pro Asp Arg Phe Thr Gly Ser Gly Ser Gly Thr Asp Phe Thr
            180             185             190

Leu Lys Ile Ser Arg Val Glu Ala Glu Asp Leu Gly Val Tyr Tyr Cys
    195             200             205

-continued

```
Trp Gln Gly Thr His Phe Pro Gln Thr Phe Gly Gly Gly Thr Lys Leu
    210             215             220

Glu Ile
225
```

```
<210> SEQ ID NO 74
<211> LENGTH: 478
<212> TYPE: PRT
<213> ORGANISM: Artificial Sequence
<220> FEATURE:
<223> OTHER INFORMATION: 5B7 CAR consensus
<220> FEATURE:
<221> NAME/KEY: SITE
<222> LOCATION: (115)..(116)
<223> OTHER INFORMATION: Linker insertion site between residues 115 and
      116

<400> SEQUENCE: 74
```

```
Gln Ile Gln Leu Val Gln Ser Gly Pro Glu Leu Lys Lys Pro Gly Glu
1               5               10              15

Thr Val Met Ile Ser Cys Lys Ala Ser Gly Tyr Ser Phe Thr Asn Tyr
            20              25              30

Gly Met Asn Trp Val Lys Gln Ala Pro Glu Lys Asp Leu Lys Trp Met
        35              40              45

Gly Trp Ile Asn Thr Tyr Thr Gly Glu Ser Arg Tyr Val Asp Glu Phe
    50              55              60

Lys Gly Arg Phe Ala Phe Ser Leu Glu Thr Ser Val Ser Ile Val Tyr
65              70              75              80

Leu Lys Ile Asn Asn Leu Lys Asn Glu Asp Met Ala Thr Tyr Phe Cys
                85              90              95

Ala Arg Gly Pro Asn Phe Asp Val Trp Gly Thr Gly Thr Thr Val Thr
            100             105             110

Val Ser Ser Asp Val Val Met Thr Gln Thr Pro Leu Thr Leu Ser Val
        115             120             125

Thr Ile Gly Gln Pro Ala Ser Ile Ser Cys Lys Ser Ser Gln Ser Leu
    130             135             140

Leu Asp Ser Asp Gly Lys Thr Tyr Leu Asn Trp Leu Leu Gln Arg Pro
145             150             155             160

Gly Gln Ser Pro Lys Arg Leu Ile Tyr Leu Val Ser Lys Leu Asp Ser
            165             170             175

Gly Val Pro Asp Arg Phe Thr Gly Ser Gly Ser Gly Thr Asp Phe Thr
        180             185             190

Leu Lys Ile Ser Arg Val Glu Ala Glu Asp Leu Gly Val Tyr Tyr Cys
        195             200             205

Trp Gln Gly Thr His Phe Pro Gln Thr Phe Gly Gly Gly Thr Lys Leu
    210             215             220

Glu Ile Val Ile Ser Asn Ser Val Met Tyr Phe Ser Ser Val Val Pro
225             230             235             240

Val Leu Gln Lys Val Asn Ser Thr Thr Thr Lys Pro Val Leu Arg Thr
            245             250             255

Pro Ser Pro Val His Pro Thr Gly Thr Ser Gln Pro Gln Arg Pro Glu
            260             265             270

Asp Cys Arg Pro Arg Gly Ser Val Lys Gly Thr Gly Leu Asp Phe Ala
        275             280             285

Pro Ser Lys Pro Phe Trp Val Leu Val Val Val Gly Gly Val Leu Ala
    290             295             300
```

-continued

```
Cys Tyr Ser Leu Leu Val Thr Val Ala Phe Ile Ile Phe Trp Val Arg
305                 310                 315                 320

Ser Lys Arg Ser Arg Leu Leu His Ser Asp Tyr Met Asn Met Thr Pro
                325                 330                 335

Arg Arg Pro Gly Pro Thr Arg Lys His Tyr Gln Pro Tyr Ala Pro Pro
            340                 345                 350

Arg Asp Phe Ala Ala Tyr Arg Ser Ala Ser Leu Arg Val Lys Phe Ser
            355                 360                 365

Arg Ser Ala Asp Ala Pro Ala Tyr Gln Gln Gly Gln Asn Gln Leu Tyr
    370                 375                 380

Asn Glu Leu Asn Leu Gly Arg Arg Glu Glu Tyr Asp Val Leu Asp Lys
385                 390                 395                 400

Arg Arg Gly Arg Asp Pro Glu Met Gly Gly Lys Pro Gln Arg Arg Lys
            405                 410                 415

Asn Pro Gln Glu Gly Leu Tyr Asn Glu Leu Gln Lys Asp Lys Met Ala
            420                 425                 430

Glu Ala Tyr Ser Glu Ile Gly Met Lys Gly Glu Arg Arg Arg Gly Lys
        435                 440                 445

Gly His Asp Gly Leu Tyr Gln Gly Leu Ser Thr Ala Thr Lys Asp Thr
    450                 455                 460

Tyr Asp Ala Leu His Met Gln Ala Leu Pro Pro Arg Leu Glu
465                 470                 475
```

```
<210> SEQ ID NO 75
<211> LENGTH: 243
<212> TYPE: PRT
<213> ORGANISM: Artificial Sequence
<220> FEATURE:
<223> OTHER INFORMATION: 3D12  Shorter scFV

<400> SEQUENCE: 75
```

```
Glu Val Gln Leu Gln Gln Ser Gly Pro Glu Leu Val Lys Pro Gly Ser
1               5                   10                  15

Ser Val Arg Ile Ser Cys Lys Ala Ser Gly Tyr Thr Phe Thr Asp Tyr
                20                  25                  30

Asn Met Asp Trp Val Lys Gln Ser His Gly Lys Ser Leu Glu Trp Ile
            35                  40                  45

Gly Thr Ile Asn Pro Asn Asn Gly Gly Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Val Arg Gln Leu Gly Leu Trp Phe Ala Tyr Trp Gly Gln Gly
            100                 105                 110

Thr Leu Val Thr Val Ser Ala Gly Thr Gly Gly Gly Ser Gly Gly Gly
        115                 120                 125

Gly Ser Gly Gly Gly Gly Ser Glu Ile Val Leu Thr Gln Ser Pro Ala
    130                 135                 140

Leu Met Ala Ala Ser Pro Gly Glu Lys Val Thr Ile Thr Cys Ser Val
145                 150                 155                 160

Ser Ser Ser Ile Ser Ser Ser Asn Leu His Trp Tyr Gln Gln Lys Ser
            165                 170                 175

Glu Thr Ser Pro Lys Pro Trp Ile Tyr Gly Thr Ser Asn Leu Ala Ser
        180                 185                 190
```

```
Gly Val Pro Val Arg Phe Ser Gly Ser Gly Ser Gly Thr Ser Tyr Ser
        195             200             205
```

```
Leu Thr Ile Ser Ser Met Glu Ala Glu Asp Ala Ala Thr Tyr Tyr Cys
        210             215             220
```

```
Gln Gln Trp Ser Ser Tyr Pro Leu Thr Phe Gly Ser Gly Thr Lys Leu
225             230             235             240
```

```
Glu Ile Lys
```

```
<210> SEQ ID NO 76
<211> LENGTH: 227
<212> TYPE: PRT
<213> ORGANISM: Artificial Sequence
<220> FEATURE:
<223> OTHER INFORMATION: 3D12  scFV consensus
<220> FEATURE:
<221> NAME/KEY: SITE
<222> LOCATION: (119)..(120)
<223> OTHER INFORMATION: Linker insertion site between residues 119 and
      120
```

```
<400> SEQUENCE: 76
```

```
Glu Val Gln Leu Gln Gln Ser Gly Pro Glu Leu Val Lys Pro Gly Ser
1               5               10              15
```

```
Ser Val Arg Ile Ser Cys Lys Ala Ser Gly Tyr Thr Phe Thr Asp Tyr
        20              25              30
```

```
Asn Met Asp Trp Val Lys Gln Ser His Gly Lys Ser Leu Glu Trp Ile
        35              40              45
```

```
Gly Thr Ile Asn Pro Asn Asn Gly Gly Thr Ser Tyr Asn Gln Lys Phe
        50              55              60
```

```
Lys Gly Lys Ala Thr Leu Thr Val Asp Lys Ser Ser Ser Thr Ala Tyr
65              70              75              80
```

```
Met Glu Leu Arg Ser Leu Thr Ser Glu Asp Ser Ala Val Tyr Tyr Cys
                85              90              95
```

```
Ala Arg Val Arg Gln Leu Gly Leu Trp Phe Ala Tyr Trp Gly Gln Gly
        100             105             110
```

```
Thr Leu Val Thr Val Ser Ala Glu Ile Val Leu Thr Gln Ser Pro Ala
        115             120             125
```

```
Leu Met Ala Ala Ser Pro Gly Glu Lys Val Thr Ile Thr Cys Ser Val
        130             135             140
```

```
Ser Ser Ser Ile Ser Ser Ser Asn Leu His Trp Tyr Gln Gln Lys Ser
145             150             155             160
```

```
Glu Thr Ser Pro Lys Pro Trp Ile Tyr Gly Thr Ser Asn Leu Ala Ser
                165             170             175
```

```
Gly Val Pro Val Arg Phe Ser Gly Ser Gly Ser Gly Thr Ser Tyr Ser
        180             185             190
```

```
Leu Thr Ile Ser Ser Met Glu Ala Glu Asp Ala Ala Thr Tyr Tyr Cys
        195             200             205
```

```
Gln Gln Trp Ser Ser Tyr Pro Leu Thr Phe Gly Ser Gly Thr Lys Leu
        210             215             220
```

```
Glu Ile Lys
225
```

```
<210> SEQ ID NO 77
<211> LENGTH: 479
<212> TYPE: PRT
<213> ORGANISM: Artificial Sequence
<220> FEATURE:
<223> OTHER INFORMATION: 3D12 CAR consensus
<220> FEATURE:
```

<221> NAME/KEY: SITE
<222> LOCATION: (119)..(120)
<223> OTHER INFORMATION: Linker insertion site between residues 119 and
      120

<400> SEQUENCE: 77

```
Glu Val Gln Leu Gln Gln Ser Gly Pro Glu Leu Val Lys Pro Gly Ser
1               5                   10                  15

Ser Val Arg Ile Ser Cys Lys Ala Ser Gly Tyr Thr Phe Thr Asp Tyr
            20                  25                  30

Asn Met Asp Trp Val Lys Gln Ser His Gly Lys Ser Leu Glu Trp Ile
        35                  40                  45

Gly Thr Ile Asn Pro Asn Asn Gly Gly Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Val Arg Gln Leu Gly Leu Trp Phe Ala Tyr Trp Gly Gln Gly
            100                 105                 110

Thr Leu Val Thr Val Ser Ala Glu Ile Val Leu Thr Gln Ser Pro Ala
            115                 120                 125

Leu Met Ala Ala Ser Pro Gly Glu Lys Val Thr Ile Thr Cys Ser Val
    130                 135                 140

Ser Ser Ser Ile Ser Ser Ser Asn Leu His Trp Tyr Gln Gln Lys Ser
145                 150                 155                 160

Glu Thr Ser Pro Lys Pro Trp Ile Tyr Gly Thr Ser Asn Leu Ala Ser
                165                 170                 175

Gly Val Pro Val Arg Phe Ser Gly Ser Gly Ser Gly Thr Ser Tyr Ser
            180                 185                 190

Leu Thr Ile Ser Ser Met Glu Ala Glu Asp Ala Ala Thr Tyr Tyr Cys
            195                 200                 205

Gln Gln Trp Ser Ser Tyr Pro Leu Thr Phe Gly Ser Gly Thr Lys Leu
    210                 215                 220

Glu Ile Lys Val Ile Ser Asn Ser Val Met Tyr Phe Ser Ser Val Val
225                 230                 235                 240

Pro Val Leu Gln Lys Val Asn Ser Thr Thr Thr Lys Pro Val Leu Arg
                245                 250                 255

Thr Pro Ser Pro Val His Pro Thr Gly Thr Ser Gln Pro Gln Arg Pro
                260                 265                 270

Glu Asp Cys Arg Pro Arg Gly Ser Val Lys Gly Thr Gly Leu Asp Phe
            275                 280                 285

Ala Pro Ser Lys Pro Phe Trp Val Leu Val Val Val Gly Gly Val Leu
    290                 295                 300

Ala Cys Tyr Ser Leu Leu Val Thr Val Ala Phe Ile Ile Phe Trp Val
305                 310                 315                 320

Arg Ser Lys Arg Ser Arg Leu Leu His Ser Asp Tyr Met Asn Met Thr
                325                 330                 335

Pro Arg Arg Pro Gly Pro Thr Arg Lys His Tyr Gln Pro Tyr Ala Pro
            340                 345                 350

Pro Arg Asp Phe Ala Ala Tyr Arg Ser Ala Ser Leu Arg Val Lys Phe
            355                 360                 365

Ser Arg Ser Ala Asp Ala Pro Ala Tyr Gln Gln Gly Gln Asn Gln Leu
    370                 375                 380
```

-continued

```
Tyr Asn Glu Leu Asn Leu Gly Arg Arg Glu Glu Tyr Asp Val Leu Asp
385                 390                 395                 400

Lys Arg Arg Gly Arg Asp Pro Glu Met Gly Gly Lys Pro Gln Arg Arg
                405                 410                 415

Lys Asn Pro Gln Glu Gly Leu Tyr Asn Glu Leu Gln Lys Asp Lys Met
                420                 425                 430

Ala Glu Ala Tyr Ser Glu Ile Gly Met Lys Gly Glu Arg Arg Arg Gly
                435                 440                 445

Lys Gly His Asp Gly Leu Tyr Gln Gly Leu Ser Thr Ala Thr Lys Asp
    450                 455                 460

Thr Tyr Asp Ala Leu His Met Gln Ala Leu Pro Pro Arg Leu Glu
465                 470                 475
```

<210> SEQ ID NO 78
<211> LENGTH: 244
<212> TYPE: PRT
<213> ORGANISM: Artificial Sequence
<220> FEATURE:
<223> OTHER INFORMATION: 1D2 Shorter scFV

<400> SEQUENCE: 78

```
Asp Val Gln Leu Gln Glu Ser Gly Pro Asp Leu Val Lys Pro Ser Gln
1                   5                   10                  15

Ser Leu Ser Leu Thr Cys Thr Val Thr Gly Tyr Ser Ile Thr Ser Gly
                20                  25                  30

Tyr Ser Trp His Trp Ile Arg Gln Phe Pro Gly Asn Lys Leu Glu Trp
                35                  40                  45

Met Gly Tyr Ile His Tyr Ser Gly Ser Thr Asn Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Ser Ser Val Thr Thr Glu Asp Thr Ala Thr Tyr Tyr Cys
                85                  90                  95

Thr Arg Ser Pro Tyr Phe Asp Val Trp Gly Thr Gly Thr Thr Val Thr
                100                 105                 110

Val Ser Ser Ala Gly Thr Gly Gly Gly Ser Gly Gly Gly Gly Ser Gly
                115                 120                 125

Gly Gly Gly Ser Asp Val Val Met Thr Gln Thr Pro Leu Ser Leu Pro
    130                 135                 140

Val Ser Leu Gly Asp Gln Ala Ser Ile Ser Cys Arg Ser Ser Gln Ser
145                 150                 155                 160

Leu Val His Ser Asp Gly Asn Thr Tyr Leu His Trp Tyr Leu Gln Lys
                165                 170                 175

Pro Gly Gln Ser Pro Lys Leu Leu Ile Tyr Lys Val Ser Asn Arg Phe
                180                 185                 190

Ser Gly Val Pro Asp Arg Phe Ser Gly Ser Gly Ser Gly Thr Asp Phe
                195                 200                 205

Thr Leu Lys Ile Ser Arg Val Glu Ala Glu Asp Leu Gly Val Tyr Phe
    210                 215                 220

Cys Ser Gln Ser Thr His Val Pro Trp Thr Phe Gly Gly Gly Thr Lys
225                 230                 235                 240

Leu Glu Ile Lys
```

<210> SEQ ID NO 79
<211> LENGTH: 228
<212> TYPE: PRT

<213> ORGANISM: Artificial Sequence
<220> FEATURE:
<223> OTHER INFORMATION: 1D2 Consensus
<220> FEATURE:
<221> NAME/KEY: SITE
<222> LOCATION: (116)..(117)
<223> OTHER INFORMATION: Linker insertion site between residues 116 and
      117

<400> SEQUENCE: 79

```
Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Tyr Ser Trp His Trp Ile Arg Gln Phe Pro Gly Asn Lys Leu Glu Trp
        35                  40                  45

Met Gly Tyr Ile His Tyr Ser Gly Ser Thr Asn Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Ser Ser Val Thr Thr Glu Asp Thr Ala Thr Tyr Tyr Cys
            85                  90                  95

Thr Arg Ser Pro Tyr Phe Asp Val Trp Gly Thr Gly Thr Thr Val Thr
            100                 105                 110

Val Ser Ser Ala Asp Val Val Met Thr Gln Thr Pro Leu Ser Leu Pro
        115                 120                 125

Val Ser Leu Gly Asp Gln Ala Ser Ile Ser Cys Arg Ser Ser Gln Ser
    130                 135                 140

Leu Val His Ser Asp Gly Asn Thr Tyr Leu His Trp Tyr Leu Gln Lys
145                 150                 155                 160

Pro Gly Gln Ser Pro Lys Leu Leu Ile Tyr Lys Val Ser Asn Arg Phe
            165                 170                 175

Ser Gly Val Pro Asp Arg Phe Ser Gly Ser Gly Ser Gly Thr Asp Phe
            180                 185                 190

Thr Leu Lys Ile Ser Arg Val Glu Ala Glu Asp Leu Gly Val Tyr Phe
            195                 200                 205

Cys Ser Gln Ser Thr His Val Pro Trp Thr Phe Gly Gly Gly Thr Lys
    210                 215                 220

Leu Glu Ile Lys
225
```

<210> SEQ ID NO 80
<211> LENGTH: 480
<212> TYPE: PRT
<213> ORGANISM: Artificial Sequence
<220> FEATURE:
<223> OTHER INFORMATION: 1D2  CAR Consensus
<220> FEATURE:
<221> NAME/KEY: SITE
<222> LOCATION: (116)..(117)
<223> OTHER INFORMATION: Linker insertion site between residues 116 and
      117

<400> SEQUENCE: 80

```
Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Tyr Ser Trp His Trp Ile Arg Gln Phe Pro Gly Asn Lys Leu Glu Trp
        35                  40                  45
```

```
Met Gly Tyr Ile His Tyr Ser Gly Ser Thr Asn Tyr Asn Pro Ser Leu
    50              55              60

Lys Ser Arg Ile Ser Ile Thr Arg Asp Thr Ser Lys Asn Gln Phe Phe
65              70              75              80

Leu Gln Leu Ser Ser Val Thr Thr Glu Asp Thr Ala Thr Tyr Tyr Cys
                85              90              95

Thr Arg Ser Pro Tyr Phe Asp Val Trp Gly Thr Gly Thr Thr Val Thr
            100             105             110

Val Ser Ser Ala Asp Val Val Met Thr Gln Thr Pro Leu Ser Leu Pro
        115             120             125

Val Ser Leu Gly Asp Gln Ala Ser Ile Ser Cys Arg Ser Ser Gln Ser
    130             135             140

Leu Val His Ser Asp Gly Asn Thr Tyr Leu His Trp Tyr Leu Gln Lys
145             150             155             160

Pro Gly Gln Ser Pro Lys Leu Leu Ile Tyr Lys Val Ser Asn Arg Phe
            165             170             175

Ser Gly Val Pro Asp Arg Phe Ser Gly Ser Gly Ser Gly Thr Asp Phe
            180             185             190

Thr Leu Lys Ile Ser Arg Val Glu Ala Glu Asp Leu Gly Val Tyr Phe
            195             200             205

Cys Ser Gln Ser Thr His Val Pro Trp Thr Phe Gly Gly Gly Thr Lys
    210             215             220

Leu Glu Ile Lys Val Ile Ser Asn Ser Val Met Tyr Phe Ser Ser Val
225             230             235             240

Val Pro Val Leu Gln Lys Val Asn Ser Thr Thr Thr Lys Pro Val Leu
            245             250             255

Arg Thr Pro Ser Pro Val His Pro Thr Gly Thr Ser Gln Pro Gln Arg
            260             265             270

Pro Glu Asp Cys Arg Pro Arg Gly Ser Val Lys Gly Thr Gly Leu Asp
        275             280             285

Phe Ala Pro Ser Lys Pro Phe Trp Val Leu Val Val Val Gly Gly Val
    290             295             300

Leu Ala Cys Tyr Ser Leu Leu Val Thr Val Ala Phe Ile Ile Phe Trp
305             310             315             320

Val Arg Ser Lys Arg Ser Arg Leu Leu His Ser Asp Tyr Met Asn Met
            325             330             335

Thr Pro Arg Arg Pro Gly Pro Thr Arg Lys His Tyr Gln Pro Tyr Ala
            340             345             350

Pro Pro Arg Asp Phe Ala Ala Tyr Arg Ser Ala Ser Leu Arg Val Lys
        355             360             365

Phe Ser Arg Ser Ala Asp Ala Pro Ala Tyr Gln Gln Gly Gln Asn Gln
    370             375             380

Leu Tyr Asn Glu Leu Asn Leu Gly Arg Arg Glu Glu Tyr Asp Val Leu
385             390             395             400

Asp Lys Arg Arg Gly Arg Asp Pro Glu Met Gly Gly Lys Pro Gln Arg
            405             410             415

Arg Lys Asn Pro Gln Glu Gly Leu Tyr Asn Glu Leu Gln Lys Asp Lys
            420             425             430

Met Ala Glu Ala Tyr Ser Glu Ile Gly Met Lys Gly Glu Arg Arg Arg
        435             440             445

Gly Lys Gly His Asp Gly Leu Tyr Gln Gly Leu Ser Thr Ala Thr Lys
    450             455             460
```

-continued

```
Asp Thr Tyr Asp Ala Leu His Met Gln Ala Leu Pro Pro Arg Leu Glu
465                 470                 475                 480

<210> SEQ ID NO 81
<211> LENGTH: 60
<212> TYPE: PRT
<213> ORGANISM: Artificial Sequence
<220> FEATURE:
<223> OTHER INFORMATION: 3GGGGS-flexible linker and human CD8 hinge

<400> SEQUENCE: 81

Gly Gly Gly Gly Ser Gly Gly Gly Gly Ser Gly Gly Gly Gly Ser Thr
1               5                   10                  15

Thr Thr Pro Ala Pro Arg Pro Pro Thr Pro Ala Pro Thr Ile Ala Ser
            20                  25                  30

Gln Pro Leu Ser Leu Arg Pro Glu Ala Cys Arg Pro Ala Ala Gly Gly
        35                  40                  45

Ala Val His Thr Arg Gly Leu Asp Phe Ala Cys Asp
    50                  55                  60

<210> SEQ ID NO 82
<211> LENGTH: 531
<212> TYPE: PRT
<213> ORGANISM: Artificial Sequence
<220> FEATURE:
<223> OTHER INFORMATION: 3D12 bi-specific T cell engager

<400> SEQUENCE: 82

Glu Val Gln Leu Gln Gln Ser Gly Pro Glu Leu Val Lys Pro Gly Ser
1               5                   10                  15

Ser Val Arg Ile Ser Cys Lys Ala Ser Gly Tyr Thr Phe Thr Asp Tyr
            20                  25                  30

Asn Met Asp Trp Val Lys Gln Ser His Gly Lys Ser Leu Glu Trp Ile
            35                  40                  45

Gly Thr Ile Asn Pro Asn Asn Gly Gly Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Val Arg Gln Leu Gly Leu Trp Phe Ala Tyr Trp Gly Gln Gly
            100                 105                 110

Thr Leu Val Thr Val Ser Ala Ala Lys Thr Thr Pro Pro Ser Val Tyr
            115                 120                 125

Pro Leu Ala Pro Gly Ser Leu Gly Gly Thr Gly Gly Gly Ser Gly Gly
        130                 135                 140

Gly Gly Ser Gly Gly Gly Gly Ser Glu Ile Val Leu Thr Gln Ser Pro
145                 150                 155                 160

Ala Leu Met Ala Ala Ser Pro Gly Glu Lys Val Thr Ile Thr Cys Ser
                165                 170                 175

Val Ser Ser Ser Ile Ser Ser Ser Asn Leu His Trp Tyr Gln Gln Lys
            180                 185                 190

Ser Glu Thr Ser Pro Lys Pro Trp Ile Tyr Gly Thr Ser Asn Leu Ala
        195                 200                 205

Ser Gly Val Pro Val Arg Phe Ser Gly Ser Gly Ser Gly Thr Ser Tyr
    210                 215                 220

Ser Leu Thr Ile Ser Ser Met Glu Ala Glu Asp Ala Ala Thr Tyr Tyr
225                 230                 235                 240
```

```
Cys Gln Gln Trp Ser Ser Tyr Pro Leu Thr Phe Gly Ser Gly Thr Lys
                245                 250                 255

Leu Glu Ile Lys Arg Ala Asp Ala Ala Pro Thr Val Ser Ile Phe Pro
            260                 265                 270

Pro Ser Ser Lys Leu Gly Asp Leu Gly Gly Gly Ser Arg Asp Asp
            275                 280                 285

Asp Ile Lys Leu Gln Gln Ser Gly Ala Glu Leu Ala Arg Pro Gly Ala
    290                 295                 300

Ser Val Lys Met Ser Cys Lys Thr Ser Gly Tyr Thr Phe Thr Arg Tyr
305                 310                 315                 320

Thr Met His Trp Val Lys Gln Arg Pro Gly Gln Gly Leu Glu Trp Ile
            325                 330                 335

Gly Tyr Ile Asn Pro Ser Arg Gly Tyr Thr Asn Tyr Asn Gln Lys Phe
            340                 345                 350

Lys Asp Lys Ala Thr Leu Thr Thr Asp Lys Ser Ser Ser Thr Ala Tyr
            355                 360                 365

Met Gln Leu Ser Ser Leu Thr Ser Glu Asp Ser Ala Val Tyr Tyr Cys
    370                 375                 380

Ala Arg Tyr Tyr Asp Asp His Tyr Cys Leu Asp Tyr Trp Gly Gln Gly
385                 390                 395                 400

Thr Thr Leu Thr Val Ser Ser Val Glu Gly Gly Ser Gly Gly Ser Gly
            405                 410                 415

Gly Ser Gly Gly Ser Gly Gly Val Asp Asp Ile Gln Leu Thr Gln Ser
            420                 425                 430

Pro Ala Ile Met Ser Ala Ser Pro Gly Glu Lys Val Thr Met Thr Cys
            435                 440                 445

Arg Ala Ser Ser Ser Val Ser Tyr Met Asn Trp Tyr Gln Gln Lys Ser
    450                 455                 460

Gly Thr Ser Pro Lys Arg Trp Ile Tyr Asp Thr Ser Lys Val Ala Ser
465                 470                 475                 480

Gly Val Pro Tyr Arg Phe Ser Gly Ser Gly Ser Gly Thr Ser Tyr Ser
            485                 490                 495

Leu Thr Ile Ser Ser Met Glu Ala Glu Asp Ala Ala Thr Tyr Tyr Cys
            500                 505                 510

Gln Gln Trp Ser Ser Asn Pro Leu Thr Phe Gly Ala Gly Thr Lys Leu
            515                 520                 525

Glu Leu Lys
    530
```

```
<210> SEQ ID NO 83
<211> LENGTH: 64
<212> TYPE: PRT
<213> ORGANISM: Artificial Sequence
<220> FEATURE:
<223> OTHER INFORMATION: Linker of the L17-CD8 construct

<400> SEQUENCE: 83

Pro Leu Gly Gly Gly Gly Ser Gly Gly Gly Gly Ser Gly Gly Gly Gly
1               5                   10                  15

Ser Gly Gly Thr Thr Thr Pro Ala Pro Arg Pro Pro Thr Pro Ala Pro
            20                  25                  30

Thr Ile Ala Ser Gln Pro Leu Ser Leu Arg Pro Glu Ala Cys Arg Pro
        35                  40                  45

Ala Ala Gly Gly Ala Val His Thr Arg Gly Leu Asp Phe Ala Cys Asp
    50                  55                  60
```

-continued

<210> SEQ ID NO 84
<211> LENGTH: 47
<212> TYPE: PRT
<213> ORGANISM: Artificial Sequence
<220> FEATURE:
<223> OTHER INFORMATION: Linker of the 45CD8h construct

<400> SEQUENCE: 84

Pro Leu Thr Thr Thr Pro Ala Pro Arg Pro Pro Thr Pro Ala Pro Thr
1               5                   10                  15

Ile Ala Ser Gln Pro Leu Ser Leu Arg Pro Glu Ala Cys Arg Pro Ala
            20                  25                  30

Ala Gly Gly Ala Val His Thr Arg Gly Leu Asp Phe Ala Cys Asp
        35                  40                  45

<210> SEQ ID NO 85
<211> LENGTH: 37
<212> TYPE: PRT
<213> ORGANISM: Artificial Sequence
<220> FEATURE:
<223> OTHER INFORMATION: Linker of the 35CD8h construct

<400> SEQUENCE: 85

Pro Leu Pro Ala Pro Thr Ile Ala Ser Gln Pro Leu Ser Leu Arg Pro
1               5                   10                  15

Glu Ala Cys Arg Pro Ala Ala Gly Gly Ala Val His Thr Arg Gly Leu
            20                  25                  30

Asp Phe Ala Cys Asp
        35

<210> SEQ ID NO 86
<211> LENGTH: 17
<212> TYPE: PRT
<213> ORGANISM: Artificial Sequence
<220> FEATURE:
<223> OTHER INFORMATION: Linker of the 15CD8h construct

<400> SEQUENCE: 86

Pro Leu Ala Gly Gly Ala Val His Thr Arg Gly Leu Asp Phe Ala Cys
1               5                   10                  15

Asp

<210> SEQ ID NO 87
<211> LENGTH: 18
<212> TYPE: PRT
<213> ORGANISM: Artificial Sequence
<220> FEATURE:
<223> OTHER INFORMATION: 18-mer Linker

<400> SEQUENCE: 87

Gly Gly Ser Ser Arg Ser Ser Ser Ser Gly Gly Gly Gly Ser Gly Gly
1               5                   10                  15

Gly Gly

<210> SEQ ID NO 88
<211> LENGTH: 5
<212> TYPE: PRT
<213> ORGANISM: Artificial Sequence
<220> FEATURE:
<223> OTHER INFORMATION: G4S linker (5-mer)

<400> SEQUENCE: 88

```
Gly Gly Gly Gly Ser
1               5
```

```
<210> SEQ ID NO 89
<211> LENGTH: 15
<212> TYPE: PRT
<213> ORGANISM: Artificial Sequence
<220> FEATURE:
<223> OTHER INFORMATION: (G4S)3 linker (15-mer)

<400> SEQUENCE: 89

Gly Gly Gly Gly Ser Gly Gly Gly Gly Ser Gly Gly Gly Gly Ser
1               5                   10                  15
```

```
<210> SEQ ID NO 90
<211> LENGTH: 20
<212> TYPE: PRT
<213> ORGANISM: Artificial Sequence
<220> FEATURE:
<223> OTHER INFORMATION: (G4S)4 linker (20-mer)

<400> SEQUENCE: 90

Gly Gly Gly Gly Ser Gly Gly Gly Gly Ser Gly Gly Gly Gly Ser Gly
1               5                   10                  15

Gly Gly Gly Ser
            20
```

```
<210> SEQ ID NO 91
<211> LENGTH: 354
<212> TYPE: PRT
<213> ORGANISM: Homo sapiens

<400> SEQUENCE: 91

Leu Glu Glu Lys Lys Gly Asn Tyr Val Val Thr Asp His Gly Ser Cys
1               5                   10                  15

Val Arg Ala Cys Gly Ala Asp Ser Tyr Glu Met Glu Glu Asp Gly Val
            20                  25                  30

Arg Lys Cys Lys Lys Cys Glu Gly Pro Cys Arg Lys Val Cys Asn Gly
        35                  40                  45

Ile Gly Ile Gly Glu Phe Lys Asp Ser Leu Ser Ile Asn Ala Thr Asn
    50                  55                  60

Ile Lys His Phe Lys Asn Cys Thr Ser Ile Ser Gly Asp Leu His Ile
65                  70                  75                  80

Leu Pro Val Ala Phe Arg Gly Asp Ser Phe Thr His Thr Pro Pro Leu
                85                  90                  95

Asp Pro Gln Glu Leu Asp Ile Leu Lys Thr Val Lys Glu Ile Thr Gly
            100                 105                 110

Phe Leu Leu Ile Gln Ala Trp Pro Glu Asn Arg Thr Asp Leu His Ala
        115                 120                 125

Phe Glu Asn Leu Glu Ile Ile Arg Gly Arg Thr Lys Gln His Gly Gln
    130                 135                 140

Phe Ser Leu Ala Val Val Ser Leu Asn Ile Thr Ser Leu Gly Leu Arg
145                 150                 155                 160

Ser Leu Lys Glu Ile Ser Asp Gly Asp Val Ile Ile Ser Gly Asn Lys
                165                 170                 175

Asn Leu Cys Tyr Ala Asn Thr Ile Asn Trp Lys Lys Leu Phe Gly Thr
            180                 185                 190

Ser Gly Gln Lys Thr Lys Ile Ile Ser Asn Arg Gly Glu Asn Ser Cys
        195                 200                 205
```

-continued

```
Lys Ala Thr Gly Gln Val Cys His Ala Leu Cys Ser Pro Glu Gly Cys
    210             215             220

Trp Gly Pro Glu Pro Arg Asp Cys Val Ser Cys Arg Asn Val Ser Arg
225             230             235             240

Gly Arg Glu Cys Val Asp Lys Cys Asn Leu Leu Glu Gly Glu Pro Arg
            245             250             255

Glu Phe Val Glu Asn Ser Glu Cys Ile Gln Cys His Pro Glu Cys Leu
            260             265             270

Pro Gln Ala Met Asn Ile Thr Cys Thr Gly Arg Gly Pro Asp Asn Cys
        275             280             285

Ile Gln Cys Ala His Tyr Ile Asp Gly Pro His Cys Val Lys Thr Cys
    290             295             300

Pro Ala Gly Val Met Gly Glu Asn Asn Thr Leu Val Trp Lys Tyr Ala
305             310             315             320

Asp Ala Gly His Val Cys His Leu Cys His Pro Asn Cys Thr Tyr Gly
            325             330             335

Cys Thr Gly Pro Gly Leu Glu Gly Cys Pro Thr Asn Gly Pro Lys Ile
            340             345             350

Pro Ser

<210> SEQ ID NO 92
<211> LENGTH: 17
<212> TYPE: PRT
<213> ORGANISM: Artificial Sequence
<220> FEATURE:
<223> OTHER INFORMATION: 17AA poly-glycine linker

<400> SEQUENCE: 92

Gly Gly Gly Gly Ser Gly Gly Gly Gly Ser Gly Gly Gly Gly Ser Gly
1               5                   10                  15

Gly
```